(12) United States Patent
Li et al.

(10) Patent No.: US 9,957,564 B2
(45) Date of Patent: *May 1, 2018

(54) APPLICATION OF A PCR SEQUENCING METHOD, BASED ON DNA BARCODING TECHNIQUE AND DNA INCOMPLETE SHEARING STRATEGY, IN HLA GENOTYPING

(75) Inventors: Jian Li, Guangdong (CN); Shiping Chen, Guangdong (CN); Xiandong Zhang, Guangdong (CN); Ying Liu, Guangdong (CN); Caifen Zhang, Guangdong (CN); Tao Liu, Guangdong (CN); Meiru Zhao, Guangdong (CN)

(73) Assignee: BGI Genomics Co., Ltd., Shenzhen (CN)

(*) Notice: Subject to any disclaimer, the term of this patent is extended or adjusted under 35 U.S.C. 154(b) by 355 days.

This patent is subject to a terminal disclaimer.

(21) Appl. No.: 13/807,660

(22) PCT Filed: Jun. 30, 2011

(86) PCT No.: PCT/CN2011/076688
§ 371 (c)(1),
(2), (4) Date: Apr. 8, 2013

(87) PCT Pub. No.: WO2012/000445
PCT Pub. Date: Jan. 5, 2012

(65) Prior Publication Data
US 2013/0237432 A1  Sep. 12, 2013

(30) Foreign Application Priority Data

Jun. 30, 2010  (CN) .......................... 2010 1 0213717
Jun. 30, 2010  (CN) .......................... 2010 1 0213719
Jun. 30, 2010  (CN) .......................... 2010 1 0213721
Dec. 24, 2010  (WO) ............... PCT/CN2010/002149
Dec. 24, 2010  (WO) ............... PCT/CN2010/002150

(51) Int. Cl.
*C12Q 1/68* (2018.01)

(52) U.S. Cl.
CPC ......... *C12Q 1/6881* (2013.01); *C12Q 1/6844* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 5,580,730 A | 12/1996 | Okamoto | |
| 5,683,872 A | 11/1997 | Rudert et al. | |
| 7,300,755 B1 | 11/2007 | Petersdorf et al. | |
| 2004/0185484 A1 | 9/2004 | Costa et al. | |
| 2008/0194418 A1* | 8/2008 | Johnson | C12Q 1/683 506/9 |
| 2009/0170713 A1 | 7/2009 | van Eijk et al. | |
| 2009/0208943 A1 | 8/2009 | van Eijk et al. | |
| 2009/0317798 A1* | 12/2009 | Heid | B01L 3/5027 435/6.12 |
| 2010/0086914 A1* | 4/2010 | Bentley et al. | 435/6 |
| 2010/0099081 A1* | 4/2010 | de Canck et al. | 435/6 |
| 2012/0309633 A1 | 12/2012 | van Eijk et al. | |

FOREIGN PATENT DOCUMENTS

| | | |
|---|---|---|
| CN | 101313078 A | 11/2008 |
| CN | 101921840 A | 12/2010 |
| CN | 101921841 A | 12/2010 |
| CN | 101921842 A | 12/2010 |
| WO | WO-98/35059 A1 | 8/1998 |
| WO | WO-2005/042764 A2 | 5/2005 |
| WO | WO-2007/037678 A2 | 4/2007 |
| WO | WO 2007073165 A1 * | 6/2007 |
| WO | WO-2007/140540 A2 | 12/2007 |
| WO | WO-2009/049889 A1 | 4/2009 |

OTHER PUBLICATIONS

Kozarewa. I, et al. Amplification-free Illumina sequencing-library preparation facilitates improved mapping and assembly of (G+C)-biased genomes. Nature Methods, vol. 6, No. 4, p. 291-295, 2009.*
Meyer. E, et al. Sequencing and de novo analysis of a coral larval transcriptome using 454 GSFIx. BMC Genomics, vol. 10, 219, p. 1-18, 2009.*
Yu, J., et al., "Analysis of Children with Type 1 Diabetes in Korea: High Prevalence of Specific Anti-Islet Autoantibodies, Immunogenetic Similarities to Western Populations with "Unique" Haplotypes, and Lack of Discrimination by Aspartic Acid at Position 57 of DQB", Clinical Immunology, 2004, vol. 113, No. 3, pp. 318-325.
Linnarsson, S., "Recent Advances in DNA Sequencing Methods—General Principles of Sample Preparation", Experimental Cell Research, 2010, vol. 316, No. 8, pp. 1339-1343.
Bentley, G., et al., High-Resolution, High-Throughput HLA Genotyping by Next-Generation Sequencing, Tissue Antigens, 2009, vol. 74, No. 5, pp. 393-403.

(Continued)

*Primary Examiner* — Suryaprabha Chunduru
(74) *Attorney, Agent, or Firm* — Drinker Biddle & Reath LLP

(57) ABSTRACT

The invention provides a PCR sequencing method, wherein the combination of primer indexes, DNA incomplete shearing strategy and the second generation sequencing technique (Paired-End sequencing technique) can make the length of PCR products that can be sequenced by a sequencer longer than the maximum sequencing length of the sequencer while making full use of the characteristics of the second generation sequencing technique such as high throughput and low cost, thereby greatly broadening its applicable scope. In addition, the present invention also provides primer indexes for the PCR sequencing method and the use of the method in genotyping, particularly in HLA analysis, and also provides the PCR primers used, particularly the PCR primers for HLA-A, B, HLA-C and HLA-DQB1 gene.

20 Claims, 12 Drawing Sheets

(56) References Cited

OTHER PUBLICATIONS

International Search Report for PCT/CN2011/076688 dated Oct. 13, 2011 with English Translation Attached.
International Preliminary Report on Patentability for PCT/CN2011/076688 dated Jan. 8, 2013 with English Translation Attached.
Office Action for Canadian Patent Application No. 2,803,940 dated May 29, 2017.

\* cited by examiner

APPLICATION OF A PCR SEQUENCING METHOD, BASED ON DNA BARCODING TECHNIQUE AND DNA INCOMPLETE SHEARING STRATEGY, IN HLA GENOTYPING

CROSS-REFERENCE TO RELATED APPLICATIONS

This application is a national stage application (under 35 U.S.C. § 371) of PCT/CN2011/076688, filed Jun. 30, 2011, claiming the priority of Chinese Patent Application No. 201010213721.2, filed Jun. 30, 2010; Chinese Patent Application No. 201010213719.5, filed Jun. 30, 2010; Chinese Patent Application No. 201010213717.6, filed Jun. 30, 2010; PCT/CN2010/002150, filed Dec. 24, 2010; and PCT/CN2010/002149, filed Dec. 24, 2010, the contents of which are incorporated herein by reference in their entirety.

RELEVANT APPLICATIONS

The present application claims the priority right of the Chinese Patent Application Nos. 201010213717.6, 201010213719.5, and 201010213721.2 as filed on Jun. 30, 2010 and the priority right of the International Application Nos. PCT/CN2010/002150 and PCT/CN2010/002149 as filed on Dec. 24, 2010, the contents of which are incorporated herein by reference in their entirety.

SUBMISSION OF SEQUENCE LISTING

The Sequence Listing associated with this application is filed in electronic format via EFS-Web and hereby incorporated by reference into the specification in its entirety. The name of the text file containing the Sequence Listing is 13807660seqlistST25. The size of the text file is 56.0 KB, and the text file was created on Nov. 3, 2015.

TECHNICAL FIELD

The present invention relates to the technical field of nucleic acid sequencing, in particular, the technical field of PCR sequencing. In addition, the present invention also relates to DNA barcoding technique and DNA incomplete shearing strategy. The method of the present invention is particularly applicable to the second generation sequencing technique, especially to the Paired-end sequencing technique of the second generation sequencing technique, and is also applicable to HLA genotyping. In particular, the present invention provides a method for HLA genotyping, in particular, a method for HLA-A, HLA-B, HLA-C and HLA-DQB1 genotyping, and also provides the primer pairs for PCR amplification used in the method.

BACKGROUND

A PCR sequencing method refers to a technique wherein DNA fragments of a gene of interest are obtained by a PCR method, and the obtained DNA fragments of the gene of interest are subjected to DNA sequencing to obtain the DNA sequence information of the gene of interest. PCR sequencing methods are widely applied to the fields such as detection of gene mutation and genotyping for a long time.

DNA sequencing technique is mainly classified into the first generation DNA sequencing technique represented by Sanger sequencing method and the second generation DNA sequencing technique represented by Illumina GA, Roche 454, ABI Solid, and the like. Sanger DNA sequencing technique is characterized by simple experimental operations, visual and accurate results, and short experimental period, and thus is wildly applied in fields such as clinical gene mutation detection and genotyping, wherein a fast turnaround time is highly required as to detection results. However, due to the characteristics such as low throughput and high cost, its application in fields where genotyping is performed in a large scale, is limited.

As compared with the first generation DNA sequencing technique, the second generation DNA sequencing technique has the characteristics such as high sequencing throughput, low cost, high level of automation, and single-molecule sequencing. Taken Illumina GA single-molecule sequencing as an example, a single sequencing run generates data of 50 G (about 50 billion) bases, 5 billion bases data per day in average, and the average sequencing cost for a base is less than 1/1000 of the sequencing cost in Sanger method. Moreover, the analysis of results can be directly carried out by a computer. Thus, the second generation DNA sequencing technique is a technique quite suitable for large-scale sequencing projects. However, the contiguous sequencing length is generally short in the second generation DNA sequencing technique. Currently, the maximum bidirectional sequencing length is 200 bp for Illumina GA; although the maximum sequencing length can be up to about 500 bp for Roche 454 GS-FLX, the sequencing cost is high and the throughput is low. When a PCR amplicon is of a length greater than the maximum sequencing length in a sequencer, the thorough sequencing of the whole amplicon cannot be accomplished by sequencing directly, and the whole DNA sequence information of the amplicon cannot be obtained. Due to short maximum sequencing length, the application of the second generation sequencing technique in PCR sequencing method is limited. In addition to gradual improvement of sequencing technique to obtain a longer maximum sequencing length, it is urgent need to develop a new technique to overcome the deficiency of the current maximum sequencing length of the second generation DNA sequencer in the PCR sequencing application field.

Human leukocyte antigen (HLA) is one of the gene systems found so far to be of the highest polymorphism. It is a primary gene system for modulating specific immune response in human bodies and determining individual difference in susceptibility to diseases, and is closely associated with allogeneic organ transplant rejection. It is found in studies that the higher the matching degree of genes, such as HLA-A, B, C, DRB1 and DQB1, as well as the resolution are in a donor and a receptor, the longer a transplant survives. It is already a regular testing item to subject a potential donor and a receptor to high-resolution HLA genotyping before hematopoietic stem cell transplantation.

The current international standard HLA high-resolution genotyping technique is a Sanger sequencing technique-based PCR sequencing method, which comprises PCR amplifying the corresponding HLA gene regions, sequencing the amplified product, subjecting the sequencing result to genotyping with a professional genotyping software, and finally obtaining the HLA genotype information of the sample. It is characterized by visual results, high resolution and capability of detecting new allele. However, due to the characteristics of Sanger sequencing, such as high cost and low throughput, its application in institutes like hematopoietic stem cell volunteer registration database (Bone Marrow Bank), in which large-scale HLA genotyping detection is required, is limited.

It was reported that a Roche 454 GS-FLX-based PCR sequencing method was used in HLA genotyping. However, since its cost for sequencing was relatively high, it was not significantly superior over the Sanger sequencing-based HLA genotyping technique in terms of sequencing throughput and sequencing cost. As compared with Roche 454 GS-FLX, Illumina GA has a shorter maximum sequencing length, but has obvious advantages in terms of sequencing throughput and sequencing cost. If the defect of the short maximum sequencing length of Illumina GA can be overcome, its application in HLA genotyping will make up for the shortage of the current HLA genotyping method.

CONTENTS OF THE INVENTION

When conducting sequencing analysis simultaneously to sequences associated with a specific gene in a large number of samples by the second generation sequencing technique, PCR sequencing strategy is generally employed, wherein the combination of primer index and the second generation sequencing technique is employed directly. When the maximum sequencing length of the sequencer can cover the length of the whole PCR product, the above strategy meets the requirements. When the maximum sequencing length of the sequencer cannot cover the length of the whole PCR product, Illumina GA needs to be replaced with the second generation sequencer having a longer maximum sequencing length (such as Roche 454 GS-FLX). If the maximum sequencing length still cannot meet the requirements, a first generation sequencer has to be employed with the scarification of cost and throughput.

The actual situation is that Illumina GA has a super high sequencing throughput, but its maximum sequencing length is 200 bp only; although the maximum sequencing length of Roche 454 GS-FLX can reach about 500 bp, the cost for sequencing is relative high and the throughput is relative low; although the maximum sequencing length of the first generation sequencer can reach above 1000 bp, its throughput and cost are not comparable to those of the second generation sequencer.

Is there a technique capable of enhancing the length of PCR products that can be sequenced thoroughly by a sequencer without the scarification of cost and throughput? The combination of primer indexes, DNA incomplete shearing strategy, and the second generation sequencing technique in the present application can make the length of PCR products that can be sequenced by a sequencer longer than the maximum sequencing length of the sequencer whilst making full use of the characteristics of the second generation sequencing technique such as high throughput and low cost, thereby greatly broadening its applicable scope. The second generation sequencing technique employed in the present invention includes, among second generation sequencing techniques, a Paired-end sequencing technique, and a PCR sequencing technique which has a DNA reference sequence for the PCR template.

The present invention provides methods for PCR sequencing, by which the limitation resulted from short maximum sequencing length is alleviated and the application of the second generation DNA sequencing technique in the PCR sequencing application field is broadened. For example, when performing sequencing with the second generation sequencing technique, index primers having a primer index added to the 5' end are used, the amplified PCR products are sheared, the sheared products are terminally repaired and have deoxyadenosine (A) ligated to their 3' ends, and then are ligated to different PCR-free adapters.

A PCR sequencing method, based on DNA barcoding technique and DNA incomplete shearing strategy, can greatly increase the number of samples labeled specifically without increasing the number of primer indexes (FIG. 5). In the present invention, the actually sequenced length of PCR products exceeds the maximum sequencing length of the sequencer by adding primer indexes to the forward and reverse PCR primers, in combination with using DNA incomplete shearing strategy, and applying the second generation sequencing technique.

The addition of an index sequence to the front end of an amplification primer is aimed to realize simultaneous sequencing of a plurality of samples. Concretely speaking, a unique primer index is added to each sample during PCR by using PCR-index/barcode technique in combination with synthesizing an index primer by adding a primer index to the 5' end of a PCR primer. As such, during the sequencing by the second generation sequencing technique, samples have to be processed one by one only in PCR step, and may be mixed together and processed simultaneously in the rest experimental steps, and the final result for each sample can be traced by virtue of its unique primer index.

"Adapter" or "library adapter" index technique refers to a library indexing technique comprising adding different library adapters to multiple sequencing libraries (different library adapters consist of different sequences, and the different portion among the sequences is called adapter index), constructing indexed sequencing libraries, then accomplishing sequencing of multiple different indexed sequencing libraries in a pool, wherein the final sequencing result for each indexed sequencing library is distinguishable. The term "PCR-Free library adapter" refers to a designed segment of bases, whose main role lies in auxiliary fixation of DNA molecule onto the sequencing chip and lies in providing the binding sites for universal sequencing primers, wherein PCR-Free library adapter may be directly ligated to the two termini of the DNA fragments in the sequencing library. Since no PCR is involved in the introduction of the adapter, the adapter is called PCR-Free library adapter. For example, PCR-FREE library adapters used in the Examples of the present invention are from ILLUMIA.

A method of constructing PCR-FREE library, wherein a library adapter index technique is used, refers to direct ligation of library adapter to the two termini of the DNA fragment of the sequencing library. Since no PCR is involved in the introduction of the library adapter, it is called PCR-Free library construction. A DNA ligase may be used for ligation in the introduction process. Since no PCR is involved in the process of library construction, inaccuracy of the final results resulted from PCR bias is avoided during the construction of a library comprising PCR products of high sequence similarity.

DNA amplification methods, DNA extraction methods, DNA purification methods and DNA sequence alignment methods as involved in the present invention may be any methods available in the art. Said methods can be selected by a person skilled in the art according to practical situations. As to DNA sequencing methods, a person skilled in the art can carry out them according to conventional methods or following the instruction of the sequencer.

The design of primer indexes varies depending on the applied experimental platform. In view of the characteristics of Illumina GA sequencing platform, the following factors are primarily considered when designing the primer indexes in the present invention: 1: a mononucleotide repeat sequence comprising 3 or more base is avoided in primer index sequences, 2: the total amount of base A and base C at the same site of all the primer indexes accounts for 30%-70% of the amount of all the bases, 3: the GC content of the primer index sequence itself is between 40 and 60%, 4: primer indexes differ from one another by at least 4 bases, 5: sequences having a high sequence similarity to the Illumina GA sequencing primers are avoided in primer index sequences, and 6: the circumstance where the addition of primer index sequences to PCR primers results in serious hairpin and dimer, are reduced.

In the present invention, two primer indexes (which are either identical or different) are added to two termini of a PCR product, respectively, so that the primer index at either terminal of the PCR product can specifically label the sample information of the PCR product. The resultant PCR product is subjected to incomplete shearing. The so-called "incomplete shearing" refers to the circumstance where the products comprise intact un-sheared PCR products and partially sheared PCR products. The shearing methods include, but are not limited to, chemical shearing methods (such as enzymatic digestion) and physical shearing methods. The physical shearing methods include ultrasonic shearing methods or mechanical shearing methods. The sheared DNA is subjected to 2% agarose electrophoresis, and all DNA bands between the maximum sequencing length and the maximum applicable DNA length of the sequencer are purified and recovered by slicing the gel (the longest DNA applicable to Illumina GA sequencer is 700 bp, and the length refers to the original DNA length, which does not comprise the length of the library adapter sequence). Methods for purification and recovery include, but are not limited to, recovery by electrophoresis and gel slicing, and recovery by magnetic beads. The recovered DNA fragments are subjected to the construction of sequencing libraries according to the procedures for constructing the sequencing libraries for the second generation sequencer, and then are subjected to sequencing. Preferably, the sequencing libraries are constructed according to the PCR-FREE procedures for constructing sequencing libraries, and Paired-End method is used as the sequencing method. PCR-Free construction of sequencing libraries is carried out according to methods known by a person skilled in the art. In the sequencing data obtained, the sequence information for all the test samples can be obtained by virtue of the primer index sequences. The sequence reads are aligned to the corresponding DNA reference sequences of the PCR products by BMA, and the complete sequence is assembled by the overlapping and linkage relationship between the sequence reads (FIG. 1). The linkage here refers to the paired-end linkage relationship due to paired-End sequencing characteristics.

In Illumina GA sequencing (Genome Analyzer Sequencer from Illumina Inc., cited as Illumina GA for brief), DNA sequence analysis is carried out based on the principle of sequencing by synthesis. It may be applied to phase haplotype, and the finally obtained data refers to a series of base sequences and may be directly applied to the alignment with the reference sequences in HLA database. Since it does not have the defect of misjudgment of peaks present in the traditional typing software, it is advantageous for automation of software typing. Illumina GA has a high sequencing throughput. Currently, one single sequencing run generates 50 G (50 billion) base data, 5 billion base data per day in average. Due to the high data throughput, a high sequencing depth can be obtained for each sequence, thereby ensuring the reliability of the sequencing results.

There are no studies on applying Illumina GA to HLA typing field yet. The present invention applies Illumina GA sequencing to HLA typing field for the first time, and accomplishes HLA typing with low cost, high throughput, high accuracy and high resolution by using a PCR sequencing technique, based on DNA barcoding technique, DNA incomplete shearing and PCR-FREE library preparation.

In the present invention, by using a PCR sequencing technique which is based on DNA barcoding technique, DNA incomplete shearing and PCR-FREE library preparation, samples to be analyzed are grouped; the samples of each group are subjected to the amplification of a fragment of interest of HLA genes with primers labeled by bidirectional primer indexes (the maximum length of PCR products depends on the maximum length of the DNA that can be applied in a sequencer; the maximum applicable DNA length is 700 bp in the current Illumina GA, and the length is the original DNA length, which does not comprise the length of the library adapter sequence); the PCR products are pooled together with the same amount, then subjected to incomplete shearing and indexed PCR-Free DNA sequencing library preparation. Different indexed sequencing libraries, as obtained from various groups of samples, are mixed in an equal mole, all the DNA fragments of a length longer than the maximum sequencing length of the sequencer are selectively recovered and are sequenced by Illumina GA sequencer. The DNA sequence reads for each sample can be obtained by screening the sequence information of adapter indexes, primer indexes and PCR primers in the total sequencing data. The resultant DNA sequences after assembly are aligned with the corresponding data in IMGT HLA professional database, thereby determining the HLA genotype of the sample finally.

In the methods described above, after shearing said DNA, DNA from samples of different groups is ligated to a different library adapter during indexed PCR-Free library preparation, and therefore in the following typing steps, the resultant sequencing data can be traced to the samples one by one based on the primer indexes and adapter indexes used in each sample. Sequences of each sample are aligned to the known DNA reference sequence corresponding to the PCR product by software. Based on the sequence overlapping and linkage relationship, an intact sequence for the PCR product is assembled from the sequences of the sheared DNA.

The present invention provides Illumina GA sequencing technique-based high-resolution HLA genotyping methods, thereby accomplishing haplotype sequencing and software typing automation, enhancing HLA genotyping throughput, and reducing cost.

Due to the requirement on the length of DNA template in the current sequencing techniques and the short read length in the current sequencing techniques, the original PCR primers for HLA-SBT methods are not applicable to new sequencing technique-based high-resolution HLA typing methods any more. The present invention designs new PCR primers with good specificity and conservation, which amplify Exons 2, 3, 4 of HLA-A, B gene independently, and whose PCR products have a length no more than 700 bp and are particularly applicable to Illumina GA (the maximum DNA length applicable to the current Illumina GA is 700 bp). A set of PCR primers as provided in the present invention is applicable to HLA genotyping for subjects (in particular human) with a large scale, a high throughput and a low cost.

In the technical solutions employed in the present invention, all the latest HLA-A/B gene sequences are downloaded from IMGT/HLA internet website, and then are saved in the local disk as HLA-A data set; meanwhile, all the latest HLA-I gene sequences other than HLA-A sequences are downloaded as the comparison data set. Said two data sets are compared to look for conservative and specific sequences for each gene site at the two termini and internal portion of Exons 2, 3, 4, and the designed PCR primer sequence is compared with the whole human genome sequence for homology. Since HLA-A/B gene is highly similar to other genes belonging to HLA-I molecules in terms of sequence, when designing PCR primers, the 3' terminal of the primer should be specific as far as possible so as to ensure the specificity of amplifying HLA-A/B gene with the primers. Meanwhile, the length of the PCR products is less than 700 bp, and the annealing temperature of forward and reverse primers are substantially the same.

Multiple pairs of candidate HLA-A/B primers meeting the design requirements are used to amplify template DNAs of common HLA-A/B serotypes. Among them, two sets of PCR primers of HLA-A/B (6 pairs for each set) with the best conservatism and specificity, for amplification of Exons 2, 3 and 4, respectively, are screened out.

The two sets of PCR primers (6 pairs for each set) are used as the basic primers, on the basis of which, 95 sets of index primers which are used for amplification of 95 and 950 DNA templates of common serotypes of HLA-A/B (the serotypes of these templates include all the common serotypes of HLA-A/B), respectively, are designed. All the PCR products are sequenced with Illumina GA Pair-End 100 after mixing in an equal amount, and the sequencing results after assembly are compared with the original typing results to confirm the conservatism and specificity of the PCR primers.

HLA-A, B primers as designed in the present invention, i.e. two sets of PCR primers of HLA-A/B (6 pairs for each set) for amplification of Exons 2, 3 and 4, respectively, are shown in Table 1 and 2.

TABLE 1

PCR primers of HLA-A, B

| SEQ ID NO: | primer No. | primer sequence | the use of primer | length of products |
|---|---|---|---|---|
| 1 | A-F2 | CCTCTGYGGGGAGAAGCAA | Amplifying Exon 2 of HLA-A gene | 480 bp |
| 2 | A-R2 | ATCTCGGACCCGGAGACTG | | |
| 3 | A-F3 | CGGGGCCAGGTTCTCACAC | Amplifying Exon 3 of HLA-A gene | 410 bp |
| 4 | A-R3 | GGYGATATTCTAGTGTTGG TCCCAA | | |
| 5 | A-F4 | GTGTCCCATGACAGATGCAA AA | Amplifying Exon 4 of HLA-A gene | 430 bp |
| 6 | A-R4 | GGCCCTGACCCTGCTAAAGG | | |
| 7 | B-F2 | AGGAGCGAGGGGACCGCA | Amplifying Exon 2 of HLA-B gene | 400 bp |
| 8 | B-R2 | CGGGCCGGGGTCACTCAC | | |
| 9 | B-F3 | CGGGGCCAGGGTCTCACA | Amplifying Exon 3 of HLA-B gene | 370 bp |
| 10 | B-R3 | GAGGCCATCCCCGGCGAC | | |
| 11 | B-F4 | GCTGGTCACATGGGTGGTCC TA | Amplifying Exon 4 of HLA-B gene | 380 bp |
| 12 | B-R4 | CTCCTTACCCCATCTCAGGG TG | | |

TABLE 2

PCR primers of HLA-A, B

| SEQ ID NO: | primer No. | primer sequence | the use of primer | length of products |
|---|---|---|---|---|
| 13 | A-F2s | CCTCTGYGGGGAGAAGCAA | Amplifying Exon 2 of HLA-A gene | 481 bp |
| 14 | A-R2s | GGATCTCGGACCCGGAGACT GT | | |
| 15 | A-F3s | TGGGCTGACCGYGGGGTC | Amplifying Exon 3 of HLA-A gene | 403 bp |
| 16 | A-R3s | GGYGATATTCTAGTGTTGGT CCCAA | | |
| 17 | A-F4s | GTGTCCCATKACAGATGCAA AA | Amplifying Exon 4 of HLA-A gene | 405 bp |
| 18 | A-R4s | GGCCCTGACCCTGCTAAAGG | | |
| 19 | B-F2s | AGGAGCGAGGGGACCGCA | Amplifying Exon 2 of HLA-B gene | 400 bp |
| 20 | B-R2s | CGGGCCGGGGTCACTCAC | | |
| 21 | B-F3s | CCAAAATCCCCGCGGGTT | Amplifying Exon 3 of HLA-B gene | 405 bp |
| 22 | B-R3s | GAGGCCATCCCCGGCGAC | | |
| 23 | B-F4s | GCTGGTCACATGGGTGGTCC TA | Amplifying Exon 4 of HLA-B gene | 374 bp |
| 24 | B-R4s | TGACCCCTCATCCCCCTCCT | | |

Degenerate primers refer to a mixture of all possible different sequences representing all different bases encoding a single amino acid. In order to increase specificity, degeneracy may be reduced according to bias of base usage in different organisms by referring to codon table, wherein R=A/G, Y=C/T, M=A/C, K=G/T, S=C/G, W=A/T, H=A/C/T, B=C/G/T, V=A/C/G, D=A/G/T, N=A/C/G/T.

The present invention designs 2 set of PCR primers (three pairs for each set) for amplification of Exons 2, 3 and 4 of HLA-C by using the method of designing PCR primers for amplification of Exons 2, 3 and 4 of HLA-A/B gene.

In the following Examples, 95 and 950 blood samples with known HLA genotypes are subjected to PCR amplification for HLA-C by using the selected 2 set of PCR primers (3 pairs for each set), respectively. The amplified products are sequenced by Sanger method and the second generation sequencing method. The sequencing results are applied to HLA-C typing, and are compared with the original typing results to confirm the conservatism and specificity of the PCR primers.

The present invention provides 2 set of PCR primers (three pairs for each set) for amplification of Exons 2, 3 and 4 of HLA-C gene, which are SEQ ID NOs: 25 and 26, 27 and 28, and 29 and 30 as shown in Table 3, and SEQ ID NOs: 31 and 32, 33 and 34, and 35 and 36 as shown in Table 4. Said 6 pairs of PCR primers have good conservatism and specificity, and can cover the full-length sequences of Exons 2, 3 and 4 of HLA-C, wherein the length of all the PCR products is less than 700 bp, which meets the requirement of normal Illumina Solexa sequencing. In addition, the primers of the present invention are also applicable for Sanger sequencing.

TABLE 3

PCR primers of Exons 2, 3 and 4 of HLA-C gene

| SEQ ID NO: | No. | primer sequence | HLA-C Exons | length of products |
|---|---|---|---|---|
| 25 | C-F2 | GACCCGGGGAGCCGCGCA | 2 | 455 bp |
| 26 | C-R2 | TCGAGGGTCTGGGCGGGTT | | |
| 27 | C-F3 | CCTTTACCCGGTTTCATTTTCRGTTT | 3 | 417 bp |
| 28 | C-R3 | CTACGGGAGATGGGGAAGGCT | | |
| 29 | C-F4 | GTGTCGCAAGAGAGATRCAAAGTGT | 4 | 451 bp |
| 30 | C-R4 | GCTCTGGGAAAGGAGGRGAAGG | | |

TABLE 4

PCR primers of Exons 2, 3 and 4 of HLA-C gene

| SEQ ID NO: | No. | primer sequence | HLA-C Exons | length of products |
|---|---|---|---|---|
| 31 | C-F2s | GACCCGGGGAGCCGCGCA | 2 | 455 bp |
| 32 | C-R2s | TCGAGGGTCTGGGCGGGTT | | |
| 33 | C-F3s | GCCCAGACCCTCGRCCGGA | 3 | 443 bp |
| 34 | C-R3s | AGATRGGGAAGGCTCCCCACT | | |
| 35 | C-F4s | TCTCAGGATRGTCACATGGGC | 4 | 481 bp |
| 36 | C-R4s | GCTCTGGGAAARGAGGRGAAGG | | |

According to the methods as described above, in order to apply the second generation sequencing technique to HLA-DQB1 genotyping, the present invention provides the PCR primers for amplification of Exons 2 and/or 3 of HLA-DQB1, which are SEQ ID NOs: 37-40 as shown in Table 5. The PCR primers have good conservatism and specificity, and can cover the full-length sequences of Exons 2, 3 of HLA-DQB1, wherein the length of all the PCR products is less than 700 bp, which meets the requirement of normal Illumina Solexa sequencing. In addition, the primers of the present invention are also applicable to Sanger sequencing.

TABLE 5

PCR primers for amplification of the corresponding Exons of HLA-DQB1

| SEQ ID NO: | Primer No. | primer sequence | amplification target | length of amplificated products |
|---|---|---|---|---|
| 37 | Q-F2 | GATTCCYCGCAGAGGATTTCG | Exon 2 of HLA-DQB1 | 311 bp |
| 38 | Q-R2 | AGGGGCRACSACGCTCACCTC | | |
| 39 | Q-F3 | CCTGTCTGTTACTGCCCTCAGT | Exon 3 of HLA-DQB1 | 339 bp |
| 40 | Q-R3 | GGCCCATAGTAACAGAAACTCAATA | | |

Genotyping may be carried out on the basis of amplification of Exons 2 and/or 3 of HLA-DQB1 by using the primer pairs for amplification and the genotyping methods as provided in the present invention. In relative to the prior art, the genotyping methods use Illumina Solexa sequencing technique, which is characterized by the capability of obtaining a high resolution HLA typing results with high throughput and low cost.

SPECIFIC MODE FOR CARRYING OUT THE INVENTION

A Method for Nucleic Acid Sequencing

In one aspect, the present invention provides a method for determining the nucleotide sequence of a nucleic acid of interest in a sample, comprising:

1) providing n samples, wherein n is an integer of ≥1, the samples are preferably from mammalian, more preferably human, particularly are human blood sample; optionally, the n samples to be analyzed are divided into m groups, m is an integer and n≥m≥1;

2) amplifying: a pair or multiple pairs of index primers are used for each sample, when there are templates from the sample, PCR amplification is performed under conditions suitable for amplifying the nucleic acid of interest, wherein each pair of index primers consist of a forward index primer and a reverse index primer (both of which may be degenerate primers) comprising primer indexes, wherein the primer indexes comprised in the forward index primer and reverse index primer may be identical or different: the primer indexes in the pairs of index primers used for different samples are different;

3) pooling: when n>1, pooling PCR products from each of the samples together:

4) shearing: subjecting the amplified products to incomplete shearing, and purifying and recovering;

5) sequencing: subjecting the recovered DNA mixture to sequencing by using the second generation sequencing technique, preferably, Paired-End technique (for example, Illumina GA, Illumina Hiseq 2000), to obtain sequences of the sheared DNA; and 6) assembling: corresponding the obtained sequencing data to samples one by one based on the unique primer index for each sample, aligning each sequence read to the DNA reference sequence corresponding to the PCR products by using alignment program (such as Blast, BWA program), assembling a complete sequence of the nucleic acid of interest from the sequences of the sheared DNA by virtue of sequence overlapping and linkage relationship.

In one aspect of the present invention, each pair of primer indexes and a pair of PCR primers form a pair of index primers, forward and reverse PCR primers have a forward primer index and a reverse primer index at 5' end (or optionally linked by a linker sequence), respectively.

In one embodiment of the present invention, said PCR primers are PCR primers for amplification of HLA gene, particularly PCR primers for amplification of HLA-A/B gene, preferably PCR primers for amplification of Exons 2, 3 and 4 of HLA-A/B and Exon 2 of HLA-DRB1, preferably PCR primers for amplification of Exons 2, 3 and 4 of HLA-A/B as shown in Table 1 or Table 2, or preferably PCR primers for amplification of Exon 2 of HLA-DRB1 as shown in Table 7.

In one embodiment of the present invention, said PCR primers are PCR primers for amplification of HLA gene, particularly PCR primers for amplification of HLA-C gene, preferably PCR primers for amplification of Exons 2, 3 and/or 4 of HLA-C; preferably, said PCR primers are shown in Table 3 or Table 4.

In one embodiment of the present invention, said PCR primers are PCR primers for amplification of HLA gene, preferably PCR primers for amplification of Exon 2 and/3 of HLA-DQB1 gene; preferably, said PCR primers are shown in Table 5.

In one aspect of the present invention, said primer indexes are designed for PCR primers, preferably for PCR primers for amplification of specific gene of HLA, more preferably for PCR primers for amplification of Exons 2, 3 and 4 of HLA-A/B and Exon 2 for HLA-DRB1, particularly for PCR primers as shown in Table 1, Table 2 or Table 7; said primer indexes particularly comprise at least 10, or at least 20, or at least 30, or at least 40, or at least 50, or at least 60, or at least 70, or at least 80, or at least 90, or 95 pairs of 95 pairs of primer indexes as shown in Table 6 (or the set of primer indexes consisting of 10-95 pairs (for example, 10-95 pairs, 20-95 pairs, 30-95 pairs, 40-95 pairs, 50-95 pairs, 60-95 pairs, 70-95 pairs, 80-95 pairs, 90-95 pairs, or 95 pairs) of the 95 pairs of primer indexes as shown in Table 6); and the set of index primers preferably comprises at least PI-1 to PI-10, or PI-11 to PI-20, or PI-21 to PI-30, or PI-31 to PI-40, or PI-41 to PI-50, or PI-51 to PI-60, or PI-61 to PI-70, or PI-71 to PI-80, or PI-81 to PI-90, or PI-91 to PI-95 of 95 pairs of primer indexes as shown in Table 6, or combinations of any two or more of them.

In one embodiment of the present invention, said DNA shearing includes chemical shearing methods and physical shearing methods, wherein the chemical shearing methods include enzymatic digestion, and the physical shearing methods include ultrasonic shearing methods or mechanical shearing methods.

In one embodiment of the present invention, after said DNA shearing, all the DNA bands between the maximum read length of the sequencer and the applicable maximum DNA length of the sequencer are purified and recovered, wherein said purification and recovery methods include, but are not limited to, recovery by electrophoresis and gel slicing, and recovery by magnetic beads.

In another embodiment of the present invention, a method for sequencing the nucleotide sequence of a nucleic acid of interest in a test sample, comprising steps 1) to 4) of claim 1, and the following steps:

5) constructing a library: constructing a PCR-free sequencing library by using the library of the sheared PCR products, wherein different library adapters may be added to distinguish different PCR-Free sequencing libraries, all the DNA bands between the maximum read length of the sequencer and the applicable maximum DNA length of the sequencer, preferably DNA fragments of 450 to 750 bp, are purified and recovered;

6) sequencing: subjecting the recovered DNA mixture to sequencing by using the second generation sequencing technique, preferably Paired-End technique (for example, Illumina GA, Illumina Hiseq 2000), obtaining the sequences of the sheared DNAs;

7) assembling: corresponding the obtained sequencing data to the samples one by one based on different library adapter sequences of the libraries and the unique primer index for each sample, aligning each sequence read to the DNA reference sequence corresponding to the PCR products by using alignment program (such as Blast, BWA program), assembling a complete sequence of the nucleic acid of interest from the sequences of the sheared DNA based on sequence overlapping and linkage relationship.

In one aspect, the present invention further provides the use of the above-mentioned method in HLA typing, characterized by comprising: sequencing a sample (particularly blood sample) from a patient by said method, and aligning the sequencing results with sequence data of Exons of HLA, preferably, Exons 2, 3, 4 of HLA-A/B, Exons 2, 3 and/or 4 of HLA-C, Exon 2 and/or 3 of HLA-DQB1 gene and/or Exon 2 of HLA-DRB1 in HLA database (such as IMGT HLA professional database); wherein if the result of sequence alignment shows 100% match, the HLA genotype of the corresponding sample is determined.

A Set of Primer Indexes

In another aspect, the present invention provides a set of primer indexes, comprising at least 10, or at least 20, or at least 30, or at least 40, or at least 50, or at least 60, or at least 70, or at least 80, or at least 90, or 95 pairs of the 95 pairs of primer indexes as shown in Table 6 (or said set of primer indexes consisting of 10-95 pairs (for example, 10-95 pairs, 20-95 pairs, 30-95 pairs, 40-95 pairs, 50-95 pairs, 60-95 pairs, 70-95 pairs, 80-95 pairs, 90-95 pairs, or 95 pairs) of the 95 pairs of primer indexes as shown in Table 6), and said set of index primers preferably comprises at least PI-1 to PI-10, or PI-11 to PI-20, or PI-21 to PI-30, or PI-31 to PI-40, or PI-41 to PI-50, or PI-51 to PI-60, or PI-61 to PI-70, or PI-71 to PI-80, or PI-81 to PI-90, or PI-91 to PI-95 of 95 pairs of primer indexes as shown in Table 6, or combinations of any two or more of them.

The present invention further provides the use of said set of primer indexes in PCR sequencing methods, wherein in particular, each pair of primer indexes and a pair of PCR primers for amplification of a sequence of interest to be tested form a pair of index primers, wherein forward and reverse PCR primers have a forward primer index and a reverse primer index at 5' end (or optionally linked by a linker sequence), respectively.

In one aspect of the present invention, said PCR primers are PCR primers for amplification of a specific gene of HLA, preferably PCR primers for amplification of Exons 2, 3, 4 of HLA-A/B gene and Exon 2 of HLA-DRB1, preferably PCR primers for amplification of Exons 2, 3 and 4 of HLA-A/B as shown in Table 1 or Table 2, or preferably PCR primers for amplification of Exon 2 of HLA-DRB1 as shown in Table 7; or preferably PCR primers for amplification of Exons 2, 3 and/or 4 of HLA-C, preferably said PCR primers are shown in Table 3 or Table 4; or preferably PCR primers for amplification of Exon 2 and/or 3 of HLA-DQB1, preferably said PCR primers are shown in Table 5.

In another aspect, the present invention provides a set of index primers comprising said set of primer indexes and a pair of PCR primers for amplification of a sequence of interest to be tested, wherein a pair of index primers comprises a pair of primer indexes and a pair of PCR primers, the forward and reverse PCR primer have a forward and a reverse primer index at 5' end (or optionally linked by a linker sequence), respectively.

In one embodiment of the present invention, said PCR primers are PCR primers for amplification of a specific gene of HLA, preferably PCR primers for amplification of Exons 2, 3, 4 of HLA-A/B gene and Exon 2 of HLA-DRB1, preferably PCR primers for amplification of Exons 2, 3 and 4 of HLA-A/B as shown in Table 1 or Table 2, or preferably PCR primers for amplification of Exon 2 of HLA-DRB1 as shown in Table 7; preferably PCR primers for amplification of Exons 2, 3 and/or 4 of HLA-C, preferably said PCR primers are shown in Table 3 or Table 4; or preferably PCR primers for amplification of Exon 2 and/or 3 of HLA-DQB1, preferably said PCR primers are shown in Table 5.

In another aspect, the present invention further provides the use of said index primers in PCR sequencing methods.

A HLA Typing Method

In one aspect, the present invention provides a HLA typing method, comprising:

1) providing n samples, wherein n is an integer of ≥1, the sample is preferably from mammalian, more preferably human, particularly human blood sample;

2) dividing n samples to be analyzed into m groups, m is an integer and n≥m≥1;

3) amplifying: a pair of index primers is used for each sample, when there are templates from the sample, PCR amplification is performed under conditions suitable for amplifying the nucleic acid of interest, wherein each pair of index primers consists of a forward index primer and a reverse index primer (both of which may be degenerate primers) comprising primer indexes, wherein the primer indexes comprised in the forward index primer and reverse index primer may be identical or different: the primer indexes in the pairs of index primers used for different samples are different;

4) pooling: pooling PCR amplified products from each of the samples together to obtain PCR product libraries;

5) shearing: subjecting the resultant PCR product libraries to incomplete shearing;

6) constructing libraries: constructing PCR-free sequencing libraries from the library of the sheared PCR products with library adapter index technique, wherein different library adapters may be added to distinguish different PCR-Free sequencing libraries, all the DNA bands between the maximum read length of the sequencer and the applicable maximum DNA length of the sequencer, particularly DNA fragments of 450 to 750 bp, are recovered;

7) sequencing: subjecting the recovered DNA mixture to sequencing by using the second generation sequencing technique, preferably Paired-End technique (for example, Illumina GA, Illumina Hiseq 2000), obtaining the sequences of the sheared DNAs;

8) assembling: corresponding the obtained sequencing results to the samples one by one based on different library adapter sequences of the libraries and the unique primer index for each sample, aligning each sequence read to the DNA reference sequence corresponding to the PCR products by using alignment program (such as Blast, BWA program), assembling a complete sequence of the nucleic acid of interest from the sequences of the sheared DNA based on sequence overlapping and linkage relationship; and 9) typing: aligning the sequencing results with sequence data of Exons of HLA, preferably, Exons 2, 3, 4 of HLA-A/B, Exons 2, 3 and/or 4 of HLA-C, Exon 2 and/or 3 of HLA-DQB1 gene and/or Exon 2 of HLA-DRB1 in HLA database (such as IMGT HLA professional database), wherein if the result of sequence alignment shows 100% match, the HLA genotype of the corresponding sample is determined.

In the HLA typing method of the present invention, a pair of index primers comprises a pair of primer indexes and a pair of PCR primers, the forward and reverse PCR primer have a forward and a reverse primer index at 5' end (or optionally linked by a linker sequence), respectively.

In one embodiment of the present invention, said PCR primers are PCR primers for amplification of a specific gene of HLA, preferably PCR primers for amplification of Exons 2, 3, 4 of HLA-A/B gene and Exon 2 of HLA-DRB1, preferably PCR primers for amplification of Exons 2, 3 and 4 of HLA-A/B as shown in Table 1 or Table 2, or preferably PCR primers for amplification of Exon 2 of HLA-DRB1 as shown in Table 7; preferably PCR primers for amplification of Exons 2, 3 and/or 4 of HLA-C, preferably said PCR primers are shown in Table 3 or Table 4; or preferably PCR primers for amplification of Exon 2 and/or 3 of HLA-DQB1, preferably said PCR primers are shown in Table 5.

In one embodiment of the present invention, said primer indexes are a set of primer indexes as described above.

In one embodiment of the HLA typing method of the present invention, said DNA shearing includes chemical shearing methods and physical shearing methods, wherein the chemical shearing methods include enzymatic digestion, and the physical shearing methods include ultrasonic shearing methods or mechanical shearing methods.

In one embodiment of the HLA typing method of the present invention, said purification and recovery methods include, but are not limited to, recovery by electrophoresis and gel slicing, and recovery by magnetic beads.

In one embodiment of the HLA typing method of the present invention, the construction of PCR-free sequencing libraries from the libraries of the sheared PCR products with library adapter indexing technique comprises, adding m library adapters to the m PCR product libraries obtained in 2), wherein each PCR product library uses a different library adapter, thereby constructing m adapter indexed sequencing libraries; m adapter indexed sequencing libraries are pooled together at equal mole to construct a mixture of adapter indexed sequencing libraries, wherein the method for linking library adapters refers to direct linkage using DNA ligase without a PCR procedure.

PCR Primers for HLA Genotyping

In one aspect, the present invention provides PCR primers for HLA genotyping, characterized by that said PCR primers are PCR primers for amplification of Exons 2, 3, 4 of HLA-A/B gene and Exon 2 of HLA-DRB1, preferably PCR primers for amplification of Exons 2, 3 and 4 of HLA-A/B as shown in Table 1 or Table 2, or preferably PCR primers for amplification of Exon 2 of HLA-DRB1 as shown in Table 7; preferably PCR primers for amplification of Exons 2, 3 and/or 4 of HLA-C, preferably said PCR primers are shown in Table 3 or Table 4; or preferably PCR primers for amplification of Exons 2 and/or 3 of HLA-DQB1, preferably said PCR primers are shown in Table 5.

The present invention further provides a sequencing method using said PCR primers, comprising providing a sample, particularly a blood sample, said blood sample is preferably from mammalian, particularly human;

amplifying: amplifying DNA from the blood sample with the PCR primers to obtain PCR products, and purifying the PCR products;

sequencing: subjecting the PCR products to sequencing, the sequencing method may be Sanger sequencing method, or the second generation sequencing method (such as Hiseq 2000, Illumina GA and Roche454).

In another aspect, the present invention further provides the use of said PCR primers in HLA genotyping, characterized by using said PCR primers, carrying out assembly and alignment analysis on the results obtained by the above sequencing method, and comparing the sequencing results with the standard sequences in the database to obtain the HLA genotyping results.

In another aspect, the present invention further provides a kit for HLA genotyping, comprising said PCR primers.

PCR Primers for HLA-A, B Genotyping

In one aspect, the present invention provides a set of PCR primers for HLA-A,B genotyping, characterized by that said PCR primers are as shown in Table 1 or Table 2.

In another aspect, the present invention provides a sequencing method using PCR primers for HLA-A,B genotyping, comprising:

providing a sample, particularly a blood sample, said blood sample is preferably from mammalian, particularly human;

amplifying: amplifying DNA from the blood sample with the PCR primers to obtain PCR products, and purifying the PCR products;

sequencing: subjecting the PCR products to sequencing, the sequencing method may be Sanger sequencing method, or the second generation sequencing method (such as Hiseq 2000, Illumina GA and Roche454).

In another aspect, the present invention further provides the use of said PCR primers in HLA genotyping, characterized by using said PCR primers, carrying out assembly and alignment analysis on the results obtained by the above sequencing method, and comparing the sequencing results with the standard sequences in the database to obtain the HLA genotyping results.

In another aspect, the present invention further provides a kit for HLA genotyping, comprising the PCR primers for HLA-A,B genotyping of the present invention.

PCR Primers for HLA-C Genotyping

The present invention further provides a new method for amplifying Exons 2, 3 and 4 of HLA-C gene, characterized by carrying out PCR amplification using the amplification primer pairs of the present invention, the sequences of the amplification primer pairs are as shown in Table 3 or Table 4.

Since Exons 2, 3 and 4 of HLA-C can be amplified by a PCR reaction, the method of the present invention is particularly suitable for HLA-C genotyping. As compared with the prior HLA-C genotyping methods, since the products obtained by using the method and the amplification primers of the present invention are controlled within 700 bp, Illumina Solexa sequencing technique-based HLA-SBT may be used during further genotyping.

The present invention further provides a method for sequencing Exons 2, 3 and 4 of HLA-C gene in samples, comprising the followings steps of:

1) providing a sample and extracting DNA of the sample;

2) amplifying the DNA with the PCR primer pair for HLA-C genotyping of the present invention to obtain PCR products, preferably purifying the PCR products, said PCR primer pair is preferably selected from the group consisting of the primer pair of SEQ ID NO: 25 and SEQ ID NO: 26, SEQ ID NO: 27 and SEQ ID NO: 28, SEQ ID NO: 29 and SEQ ID NO: 30, or SEQ ID NO: 31 and SEQ ID NO: 32, SEQ ID NO: 33 and SEQ ID NO: 34, SEQ ID NO: 35 and SEQ ID NO: 36;

3) subjecting the PCR products to sequencing, preferably by the second generation sequencing method, such as Illumina Solexa or Roche454.

The present invention further provides a HLA-C genotyping method, comprising:

1) PCR amplifying Exons 2, 3 and/or 4 of HLA-C gene of the sample to be tested with the PCR primer pair for HLA-C genotyping of the present invention, said PCR primer pair is preferably selected from the group consisting of the primer pair of SEQ ID NO: 25 and SEQ ID NO: 26, SEQ ID NO: 27 and SEQ ID NO: 28, SEQ ID NO: 29 and SEQ ID NO: 30, or SEQ ID NO: 31 and SEQ ID NO: 32, SEQ ID NO: 33 and SEQ ID NO: 34, SEQ ID NO: 35 and SEQ ID NO: 36;

2) subjecting the amplified exons to sequencing, comparing the sequencing results with the standard sequences in the database so as to determine the genotyping results, wherein the sequencing is carried out by Sanger sequencing method, or the second generation sequencing method, such as Illumina Solexa or Roche454.

In another aspect, the present invention further provides a kit for HLA-C genotyping, comprising the PCR primer pair for HLA-C genotyping of the present invention, preferably selected from the group consisting of the primer pair of SEQ ID NO: 25 and SEQ ID NO: 26, SEQ ID NO: 27 and SEQ ID NO: 28, SEQ ID NO: 29 and SEQ ID NO: 30, or SEQ ID NO: 31 and SEQ ID NO: 32, SEQ ID NO: 33 and SEQ ID NO: 34, SEQ ID NO: 35 and SEQ ID NO: 36. In one embodiment, said kit further comprises additional agents, for example, agents for DNA amplification, DNA purification, and/or DNA sequencing.

Genotyping may be performed on the basis of amplification of Exons 2, 3 and 4 of HLA-C, by using the amplification primer pair and the genotyping method as provided in the present invention. Hence, as compared with the prior art, the genotyping utilizes Illumina Solexa sequencing technique, enhances the throughput, simplifies the procedure, and meanwhile save time and cost.

PCR Primers for HLA-DQB1 Genotyping

The present invention further provides a new method for amplifying Exon 2 and/or 3 of HLA-DQB1, characterized by carrying out PCR amplification with the amplification primer pairs of the present invention, said amplification primer pairs are as shown in Table 5.

Since Exons 2 and/or 3 of HLA-DQB1 can be amplified by a PCR reaction, the method of the present invention is particularly suitable for HLA-DQB1 genotyping. As compared with the prior HLA-DQB1 genotyping methods, since the products obtained by using the method and the amplification primers of the present invention are controlled within 300-400 bp, Illumina Solexa sequencing technique-based HLA-SBT may be used during further typing.

The present invention further provides a method for sequencing Exon 2 and/or 3 of HLA-DQB1 in samples, comprising the following steps of:

1) providing a sample and extracting DNA of the sample;

2) amplifying the DNA with the PCR primer pair for HLA-DQB1 genotyping of the present invention, preferably PCR primer pairs shown in Table 5, to obtain PCR products, preferably purifying the PCR products;

3) subjecting the PCR products to sequencing, preferably by the second generation sequencing method, such as Illumina Solexa or Roche454.

In another aspect of the present invention, the present invention provides an improved method for HLA-DQB1 genotyping, comprising:

1) amplifying Exon 2 and/or 3 of HLA-DQB1 to be tested with the PCR primer pair for HLA-DQB1 genotyping of the present invention, preferably the PCR primer pairs as shown in Table 5;

2) subjecting the amplified exons to sequencing, comparing the sequencing results with the standard sequences in the database so as to determine the genotyping results, wherein the sequencing method may be Sanger sequencing method or the second generation sequencing method, such as Illumina Solexa or Roche454.

In another aspect, the present invention further provides a kit for HLA-DQB1 genotyping, comprising the PCR primer pair for HLA-DQB1 genotyping of the present invention, preferably, the PCR amplification primer pairs as shown in Table 5. In one embodiment, said kit further comprises additional agents, for example, agents for DNA amplification, DNA purification, and/or DNA sequencing.

DESCRIPTION OF DRAWINGS

FIG. 2: A drawing illustrating the results of electrophoresis of PCR products of the corresponding Exons of HLA-A/B/DRB1 in Sample No. 1 of Example 2. It can be seen from electrophoretogram that PCR products are a series of single bands of 300 bp-500 bp, wherein Lane M is a marker of molecular weight (DL 2000, Takara Co.), Lanes 1-7 are the PCR products of the exons (A2, A3, A4, B2, B3, B4, DRB1-2) of HLA-A/B/DRB1 of Sample No. 1, and there is no amplification band in negative control (N). The results of other samples are similar.

FIG. 16 shows the electrophoretic results of PCR products from the corresponding Exons of HLA-A/B/C/DQB1 in Sample No. 1 in Example 12. It can be seen from electrophoretogram that PCR products are a series of single bands of 300 bp-500 bp, wherein Lane M is a marker of molecular weights (DL 2000, Takara Co.); Lanes 1-10 are the PCR amplified products of the Exons (A2, A3, A4, B2, B3, B4, C2, C3, C4, DQB1) of HLA-A/B/C/DQB1 of Sample No. 1; no amplification band is present in negative control (N). The results of other samples are similar.

EXAMPLES

Figure 1:
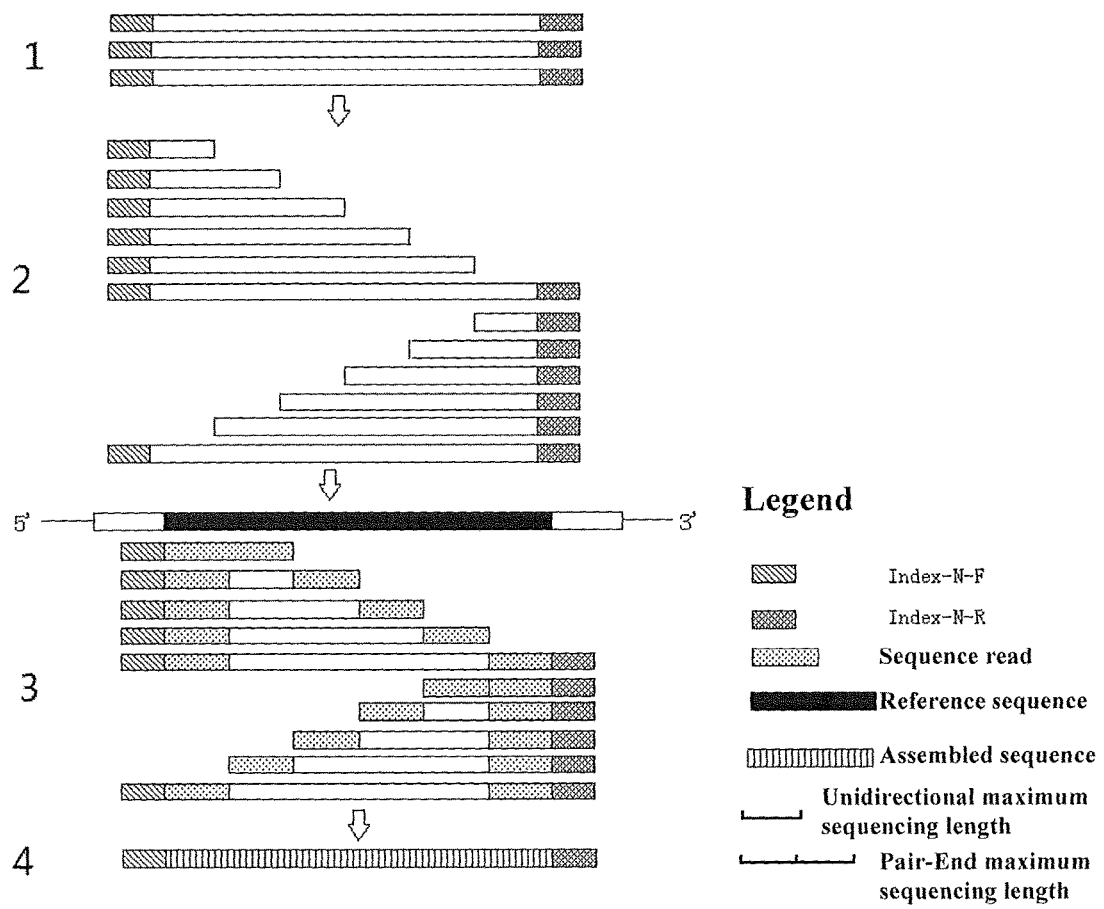
FIG. 1: A drawing illustrating the sequence assembling after labeling with primer indexes, DNA shearing and DNA sequencing. The forward and reverse primer index sequences Index-N-F/R (1) are introduced to the two termini of the PCR products of the sample No. N. The PCR products after shearing by a physical shearing method, comprises products carrying primer index sequences at one end, products carrying no primer index sequence at two termini, and completely unsheared products. All the DNA bands between the maximum read length of the sequencer and the applicable maximum DNA length of the sequencer are purified and recovered by gel slicing, and used for sequencing (2). The sequencing data of the PCR products belonging to the sample No. N are traced using Index-N-F/R. The known reference sequences of the PCR products are used to localize the relative positions of the sequence reads, and the sequencing results of the complete PCR products are assembled based on the overlapping and linkage relationship between the sequence reads (3, 4).

The embodiments of the present invention are described in detail in the following examples. However, a person skilled in the art would understand that the following examples are used to illustrate the present invention rather than restricting the scope of the present invention.

In Examples 1-6 of the present invention, Exons 2, 3, 4 of HLA-A/B and Exon 2 of HLA-DRB1 in 95 samples were genotyped by using the combination of primer indexes+DNA incomplete shearing strategy+Illumia GA sequencer Paired-End 100 sequencing technique (PCR products have a length ranging from 290 bp to 500 bp), demonstrating that the method of the invention could accomplish the typing of gene fragments of a length exceeding the maximum read length of sequencer whilst sufficiently utilizing the characteristics of the second generation sequencer, such as high throughput and low cost.

Principle: for the sample to be analyzed, primer indexes were introduced to the two termini of the PCR products of Exons 2, 3, 4 of HLA-A/B and Exon 2 of HLA-DRB1 by PCR reaction so as to specifically label the sample information of the PCR products. The products of PCR amplification of three sites (HLA-A/B/DRB1) in each group of samples were pooled together to obtain a library of PCR products; after incomplete ultrasonic shearing of the library of PCR products, a PCR-free sequencing library was constructed. The sequencing library was subjected to 2% low melting point agarose gel electrophoresis, and all the DNA bands of a length ranging from 450 bp to 750 bp were purified and recovered by gel slicing (during the construction of the PCR-Free sequencing library, since library adapters were added to the two termini of the DNA fragments, the length of the DNA band as shown in the electrophoretogram was about 250 bp longer than the actual length of the DNA fragments; therefore, the fragments of a length ranging from 450 bp to 700 bp as recovered here actually correspond to DNA fragments of an original length ranging from 200 bp to 500 bp). The recovered DNA was sequenced by Illumina GA PE-100. The sequence information of all the tested samples can be traced by primer index sequences, and the sequence of the whole PCR product can be assembled on the basis of the known reference sequences and the overlapping and linkage relationship between the sequences of DNA fragments, The complete sequence of the original PCR product can be assembled with the standard database of the corresponding exons of HLA-A/B/DRB1, thereby accomplishing HLA-A/B/DRB1 genotyping.

Example 1

Sample Extraction

DNAs were extracted from 95 blood samples with known HLA-SBT typing results (China Marrow Donor Program cited hereafter as (CMDP)) by using KingFisher Automatic Extraction Instrument (US Thermo Co.). The main steps were as followed: as directed in the handbook, a certain amount of self-contained agents was added to six deep-well plates and one shallow-well plate equipped by the King-Fisher Automatic Extraction Instrument, and all the plates, to which the agents were added, were placed in the corresponding positions as required. The program "Bioeasy_200 ul Blood DNA_KF.msz" was selected, and was implemented to extract nucleic acids by pressing "star". Approximately 100 μl eluted products (i.e. the extracted DNA) were collected from plate Elution after the program was finished.

Example 2

PCR Amplification

Different PCR index primers were made by synthesizing PCR primers having different primer indexes at 5' end, and such different PCR index primers may be applied to different samples, wherein the PCR primers were PCR primers for Exons 2, 3, 4 of HLA-A/B and Exon 2 of HLA-DRB1. Thereafter, primer indexes were introduced to the two termini of the PCR products by PCR reaction, thereby specifically labeling the PCR products from different samples.

95 sets of PCR index primers were used to amplify 95 DNA samples, respectively, wherein each set of PCR index primers consisted of a pair of bidirectional primer indexes (Table 6) and PCR primers for amplification of Exons 2, 3, 4 of HLA-A/B (Table 1) and of Exon 2 of HLA-DRB1 (Table 7), each forward PCR primer has the forward primer index in the pair of primer indexes linked at the 5' end, and the reverse PCR primer has the reverse primer index in the pair of primer indexes linked at the 5' end. During the synthesis of primers, the primer indexes were directly added to the 5' end of the PCR primers.

The 95 DNAs obtained from the sample extraction step of Example 1 were designated as No. 1-95. PCR reaction took place in 96-well plates, 7 plates in total, designated as HLA-P-A2, HLA-P-A3, HLA-P-A4, HLA-P-B2, HLA-P-B3, HLA-P-B4 and HLA-P-DRB1-2 (A2/A3/A4, B2/B3/B4, DRB1-2 represent the amplified sites), wherein a negative control without adding any template was set in each plate, and the primers used in the negative control were the same as those for Template 1. During experimentation, the numbering information of the samples corresponding to each pair of primer indexes was recorded.

TABLE 6

Relevant information of primer indexes

| Primer index No. | Forward primer index | Reverse primer index | Corresponding position in 96-well plate | Corresponding template (Group 1) |
|---|---|---|---|---|
| PI-1 | TCGCAGACATCA (SEQ ID NO: 41) | TGACACGATGCT (SEQ ID NO: 42) | A1 | 1 |
| PI-2 | TACATCGCACTA (SEQ ID NO: 43) | TACAGATGCTGA (SEQ ID NO: 44) | A2 | 2 |
| PI-3 | CTCGATGAGTAC (SEQ ID NO: 45) | ACGTCTAGACAC (SEQ ID NO: 46) | A3 | 3 |
| PI-4 | TCTGTATACTCA (SEQ ID NO: 47) | TGCTGTAGTGAC (SEQ ID NO: 48) | A4 | 4 |
| PI-5 | TATCTGCTCATA (SEQ ID NO: 49) | AGATATCGAGCT (SEQ ID NO: 50) | A5 | 5 |
| PI-6 | TACATGCTGAGC (SEQ ID NO: 51) | ACGTGTCTATCA (SEQ ID NO: 52) | A6 | 6 |
| PI-7 | TCATATCGCGAT (SEQ ID NO: 53) | AGATCGTATAGC (SEQ ID NO: 54) | A7 | 7 |
| PI-8 | ACAGATGCACGC (SEQ ID NO: 55) | ATCTCGTGACAG (SEQ ID NO: 56) | A8 | 8 |

TABLE 6-continued

Relevant information of primer indexes

| Primer index No. | Forward primer index | Reverse primer index | Corresponding position in 96-well plate | Corresponding template (Group 1) |
|---|---|---|---|---|
| PI-9 | TAGATCGTACAT (SEQ ID NO: 57) | ACTAGTACACGC (SEQ ID NO: 58) | A9 | 9 |
| PI-10 | ACTACACGTCTC (SEQ ID NO: 59) | ATAGTCACGCGT (SEQ ID NO: 60) | A10 | 10 |
| PI-11 | AGACTCGCGTAT (SEQ ID NO: 61) | TACTAGCTGACG (SEQ ID NO: 62) | A11 | 11 |
| PI-12 | ATACTAGTGCTC (SEQ ID NO: 63) | TGTATCGTGCTC (SEQ ID NO: 64) | A12 | 12 |
| PI-13 | CACGATGACATC (SEQ ID NO: 65) | TAGTGAGCGCAC (SEQ ID NO: 66) | B1 | 13 |
| PI-14 | TGCTGTCTCGAG (SEQ ID NO: 67) | CATAGCAGTGTC (SEQ ID NO: 68) | B2 | 14 |
| PI-15 | TGTGCTCGAGTC (SEQ ID NO: 69) | TCTGATCGAGCA (SEQ ID NO: 70) | B3 | 15 |
| PI-16 | CACTCGTACATC (SEQ ID NO: 71) | AGCGATGCTCAT (SEQ ID NO: 72) | B4 | 16 |
| PI-17 | CGACGTGCTCGC (SEQ ID NO: 73) | CGCGTACTGCAG (SEQ ID NO: 74) | B5 | 17 |
| PI-18 | ACGCATCTATAC (SEQ ID NO: 75) | CTAGTATCGCAG (SEQ ID NO: 76) | B6 | 18 |
| PI-19 | CGAGATGACTCT (SEQ ID NO: 77) | TGTATACACGAT (SEQ ID NO: 78) | B7 | 19 |
| PI-20 | ACTGTCTCGAGC (SEQ ID NO: 79) | ACGTAGCGCACA (SEQ ID NO: 80) | B8 | 20 |
| PI-21 | CATCTGCTATAG (SEQ ID NO: 81) | TCTAGCTCATGA (SEQ ID NO: 82) | B9 | 21 |
| PI-22 | ACGCACTCTAGA (SEQ ID NO: 83) | CTATGCACTGAT (SEQ ID NO: 84) | B10 | 22 |
| PI-23 | TGAGATACAGTA (SEQ ID NO: 85) | ATCTGCTATGAC (SEQ ID NO: 86) | B11 | 23 |
| PI-24 | ACTCATCGTGCT (SEQ ID NO: 87) | TAGAGCTGTCAC (SEQ ID NO: 88) | B12 | 24 |
| PI-25 | TACACTGTCTAT (SEQ ID NO: 89) | CAGCACATAGAT (SEQ ID NO: 90) | C1 | 25 |
| PI-26 | CACAGTACTCGC (SEQ ID NO: 91) | CTGCTAGTGTAT (SEQ ID NO: 92) | C2 | 26 |
| P1-27 | TGTACTATCATA (SEQ ID NO: 93) | TGTGATAGACAC (SEQ ID NO: 94) | C3 | 27 |
| PI-28 | CTAGTACTGACG (SEQ ID NO: 95) | AGCGAGTCTACT (SEQ ID NO: 96) | C4 | 28 |
| PI-29 | TAGACTGAGCTA (SEQ ID NO: 97) | ACATACTGAGAC (SEQ ID NO: 98) | C5 | 29 |
| PI-30 | CAGACGCGTGAG (SEQ ID NO: 99) | TACATCTCGTAT (SEQ ID NO: 100) | C6 | 30 |
| PI-31 | CGCGACATCACG (SEQ ID NO: 101) | TAGCGATGAGAC (SEQ ID NO: 102) | C7 | 31 |
| PI-32 | ACACTCATAGAT (SEQ ID NO: 103) | CTATCATGACAC (SEQ ID NO: 104) | C8 | 32 |

TABLE 6-continued

Relevant information of primer indexes

| Primer index No. | Forward primer index | Reverse primer index | Corresponding position in 96-well plate | Corresponding template (Group 1) |
|---|---|---|---|---|
| PI-33 | AGCGTATACTAG (SEQ ID NO: 105) | CATACTCACGTA (SEQ ID NO: 106) | C9 | 33 |
| PI-34 | TGTCGTGCTATC (SEQ ID NO: 107) | ACATGACTCACG (SEQ ID NO: 108) | C10 | 34 |
| PI-35 | CGCTAGACTGTA (SEQ ID NO: 109) | TACTATAGTCGA (SEQ ID NO: 110) | C11 | 35 |
| P1-36 | ACAGTGTAGCGC (SEQ ID NO: 111) | TGATATGCTACA (SEQ ID NO: 112) | C12 | 36 |
| PI-37 | CACTCTATCGAC (SEQ ID NO: 113) | TCACGCGATGAG (SEQ ID NO: 114) | D1 | 37 |
| PI-38 | ACACTCTAGTCA (SEQ ID NO: 115) | ACGTAGATCTAT (SEQ ID NO: 116) | D2 | 38 |
| PI-39 | CATATGAGATCG (SEQ ID NO: 117) | AGCAGAGTGCTC (SEQ ID NO: 118) | D3 | 39 |
| PI-40 | CAGCTATCATAC (SEQ ID NO: 119) | CACTGCAGACGA (SEQ ID NO: 120) | D4 | 40 |
| PI-41 | TATACTCTAGAT (SEQ ID NO: 121) | TGCATAGAGCGC (SEQ ID NO: 122) | D5 | 41 |
| PI-42 | TGTATGCTCGTC (SEQ ID NO: 123) | TCGTGACAGATC (SEQ ID NO: 124) | D6 | 42 |
| PI-43 | TAGTGATGCTCT (SEQ ID NO: 125) | ACGAGCTGATAT (SEQ ID NO: 126) | D7 | 43 |
| PI-44 | AGACTCTGAGTC (SEQ ID NO: 127) | CTGATAGTATCA (SEQ ID NO: 128) | D8 | 44 |
| PI-45 | CTCATAGACTAC (SEQ ID NO: 129) | ATCGCGAGTGAC (SEQ ID NO: 130) | D9 | 45 |
| PI-46 | TCGCTCACTACA (SEQ ID NO: 131) | TGTCTCGACATC (SEQ ID NO: 132) | D10 | 46 |
| PI-47 | ATAGAGTCTCAT (SEQ ID NO: 133) | CGCATAGCGTAT (SEQ ID NO: 134) | D11 | 47 |
| PI-48 | CGAGACACTCGC (SEQ ID NO: 135) | TCGTAGTCTACA (SEQ ID NO: 136) | D12 | 48 |
| PI-49 | CAGCATACTATC (SEQ ID NO: 137) | TCGTGATACAGA (SEQ ID NO: 138) | E1 | 49 |
| PI-50 | CAGCTATAGTCT (SEQ ID NO: 139) | ATGCAGATATCT (SEQ ID NO: 140) | E2 | 50 |
| PI-51 | TCTATCGATGCA (SEQ ID NO: 141) | ACACGCAGATCG (SEQ ID NO: 142) | E3 | 51 |
| PI-52 | CATGAGTATAGC (SEQ ID NO: 143) | CTAGCTGACGTA (SEQ ID NO: 144) | E4 | 52 |
| PI-53 | TAGCATATCGAG (SEQ ID NO: 145) | TACACGTATGAG (SEQ ID NO: 146) | E5 | 53 |
| PI-54 | ACGACTCGCTAC (SEQ ID NO: 147) | TCATGACTAGTA (SEQ ID NO: 148) | E6 | 54 |
| PI-55 | TAGCATACACGC (SEQ ID NO: 149) | TGACGCGTATAC (SEQ ID NO: 150) | E7 | 55 |
| PI-56 | CGTCATATGCAG (SEQ ID NO: 151) | TATAGCGATGAC (SEQ ID NO: 152) | E8 | 56 |

TABLE 6-continued

Relevant information of primer indexes

| Primer index No. | Forward primer index | Reverse primer index | Corresponding position in 96-well plate | Corresponding template (Group 1) |
|---|---|---|---|---|
| PI-57 | TGCAGCGAGTAC (SEQ ID NO: 153) | TCGACGCTAGCG (SEQ ID NO: 154) | E9 | 57 |
| PI-58 | CGTGTCGACAGA (SEQ ID NO: 155) | CAGTCGTGAGCA (SEQ ID NO: 156) | E10 | 58 |
| PI-59 | ACTCGACGTGAG (SEQ ID NO: 157) | ACGCGAGTGATA (SEQ ID NO: 158) | E11 | 59 |
| PI-60 | ACTCGTCTGACG (SEQ ID NO: 159) | TGCTATCACTGA (SEQ ID NO: 160) | E12 | 60 |
| PI-61 | CATACTGTATCT (SEQ ID NO: 161) | TACATAGATGTC (SEQ ID NO: 162) | F1 | 61 |
| PI-62 | TCTACTCGTGAC (SEQ ID NO: 163) | CACGTATAGTGA (SEQ ID NO: 164) | F2 | 62 |
| PI-63 | CTGCACTAGACA (SEQ ID NO: 165) | ACTCATATCGCA (SEQ ID NO: 166) | F3 | 63 |
| PI-64 | ACACGAGCTCAT (SEQ ID NO: 167) | CACTCATATCGA (SEQ ID NO: 168) | F4 | 64 |
| PI-65 | TACAGATAGTCT (SEQ ID NO: 169) | TCGTCTGTGATA (SEQ ID NO: 170) | F5 | 65 |
| PI-66 | TACACTCGTGCT (SEQ ID NO: 171) | TGACGCTCATCT (SEQ ID NO: 172) | F6 | 66 |
| PI-67 | TACATGTGACGA (SEQ ID NO: 173) | TCGTACATGCTC (SEQ ID NO: 174) | F7 | 67 |
| PI-68 | TGTATGATCTCG (SEQ ID NO: 175) | CACTGTGCTCAT (SEQ ID NO: 176) | F8 | 68 |
| PI-69 | CAGTACACTCTA (SEQ ID NO: 177) | ACTGCATGATCG (SEQ ID NO: 178) | F9 | 69 |
| PI-70 | CATACTATCACG (SEQ ID NO: 179) | TCGTGTCACTAC (SEQ ID NO: 180) | F10 | 70 |
| PI-71 | CACTATACAGAT (SEQ ID NO: 181) | CGACACGTACTA (SEQ ID NO: 182) | F11 | 71 |
| PI-72 | ATATCGTAGCAT (SEQ ID NO: 183) | TCGTGATCACTA (SEQ ID NO: 184) | F12 | 72 |
| PI-73 | TAGTCTATACAT (SEQ ID NO: 185) | AGACGCTGTCGA (SEQ ID NO: 186) | G1 | 73 |
| PI-74 | TGTCACAGTGAC (SEQ ID NO: 187) | TCATATGATCGA (SEQ ID NO: 188) | G2 | 74 |
| PI-75 | ATCGACTATGCT (SEQ ID NO: 189) | CGATCATATGAG (SEQ ID NO: 190) | G3 | 75 |
| PI-76 | ATACTAGCATCA (SEQ ID NO: 191) | TCATGCTGACGA (SEQ ID NO: 192) | G4 | 76 |
| PI-77 | CACTGACGCTCA (SEQ ID NO: 193) | CACTACATCGCT (SEQ ID NO: 194) | G5 | 77 |
| PI-78 | TCGCTCATCTAT (SEQ ID NO: 195) | TAGTACAGAGCT (SEQ ID NO: 196) | G6 | 78 |
| PI-79 | TGTATCACGAGC (SEQ ID NO: 197) | ATGATCGTATAC (SEQ ID NO: 198) | G7 | 79 |
| PI-80 | TACTGCTATCTC (SEQ ID NO: 199) | CGCTGCATAGCG (SEQ ID NO: 200) | G8 | 80 |

TABLE 6-continued

Relevant information of primer indexes

| Primer index No. | Forward primer index | Reverse primer index | Corresponding position in 96-well plate | Corresponding template (Group 1) |
|---|---|---|---|---|
| PI-81 | CGCGAGCTCGTC (SEQ ID NO: 201) | ACTCGATGAGCT (SEQ ID NO: 202) | G9 | 81 |
| PI-82 | TAGAGTCTGTAT (SEQ ID NO: 203) | TGTCTATCACAT (SEQ ID NO: 204) | G10 | 82 |
| PI-83 | TACTATCGCTCT (SEQ ID NO: 205) | TATGTGACATAC (SEQ ID NO: 206) | G11 | 83 |
| PI-84 | TAGATGACGCTC (SEQ ID NO: 207) | TACTCGTAGCGC (SEQ ID NO: 208) | G12 | 84 |
| P1-85 | TCGCGTGACATC (SEQ ID NO: 209) | ATCTACTGACGT (SEQ ID NO: 210) | H1 | 85 |
| PI-86 | ACACGCTCTACT (SEQ ID NO: 211) | ACAGTAGCGCAC (SEQ ID NO: 212) | H2 | 86 |
| PI-87 | TACATAGTCTCG (SEQ ID NO: 213) | CTAGTATCATGA (SEQ ID NO: 214) | H3 | 87 |
| PI-88 | TGAGTAGCACGC (SEQ ID NO: 215) | TCGATCATGCAG (SEQ ID NO: 216) | H4 | 88 |
| PI-89 | TAGATGCTATAC (SEQ ID NO: 217) | TACATGCACTCA (SEQ ID NO: 218) | H5 | 89 |
| PI-90 | ATCGATGTCACG (SEQ ID NO: 219) | CAGCTCGACTAC (SEQ ID NO: 220) | H6 | 90 |
| PI-91 | ATCATATGTAGC (SEQ ID NO: 221) | CTCTACAGTCAC (SEQ ID NO: 222) | H7 | 91 |
| PI-92 | TAGCATCGATAT (SEQ ID NO: 223) | AGATAGCACATC (SEQ ID NO: 224) | H8 | 92 |
| PI-93 | TGATCGACGCTC (SEQ ID NO: 225) | CTAGATATCGTC (SEQ ID NO: 226) | H9 | 93 |
| PI-94 | TGCAGCTCATAG (SEQ ID NO: 227) | TACAGACTGCAC (SEQ ID NO: 228) | H10 | 94 |
| PI-95 | CGACGTAGAGTC (SEQ ID NO: 229) | CAGTAGCACTAC (SEQ ID NO: 230) | H11 | 95 |

TABLE 7

PCR primers for amplification of the corresponding exons of DRB1 and without primer indexes

| primer No. | primer sequence | use of primer | length of products |
|---|---|---|---|
| D2-F1 | CACGTTTCTTGGAGTACTCTA (SEQ ID NO: 231) | For amplification of Exon 2 of HLA-DRB1 gene | 300 bp |
| D2-F2 | GTTTCTTGTGGCAgCTTAAgTT (SEQ ID NO: 232) | | |
| D2-F3 | CCTGTGGCAGGGTAAGTATA (SEQ ID NO: 233) | | |
| D2-F4 | GTTTCTTGAAGCAGGATAAGTT (SEQ ID NO: 234) | | |
| D2-F5 | GCACGTTTCTTGGAGGAGG (SEQ ID NO: 235) | | |
| D2-F6 | TTTCCTGTGGCAGCCTAAGA (SEQ ID NO: 236) | | |
| D2-F7 | GTTTCTTGGAGCAGGTTAAAC (SEQ ID NO: 237) | | |
| D2-R | CCTCACCTCGCCGCTGCAC (SEQ ID NO: 238) | | |

D2-F1, D2-F2, D2-F3, D2-F4, D2-F5, D2-F6, D2-F7 were forward primers for amplification of Exon 2 of HLA-DRB1, D2-R was a reverse primer for amplification of Exon 2 of HLA-DRB1.

PCR procedure for HLA-A/B/DRB1 was as followed:

96° 2 min

95° 30 s→60° 30 s→72° 20 s (32 cycles)

15° ∞

PCR reaction system for HLA-A/B was as followed, wherein all the agents were purchased from Promega (Beijing) Bio-Tech Co.

| | |
|---|---|
| Promega 5x buffer I (Mg2+ plus) | 5.0 ul |
| dNTP Mixture (2.5 mM/μl each) | 2.0 ul |
| $PI_{nf}$-A/B-$F_{2/3/4}$ (2 pmol/ul) | 1.0 ul |
| $PI_{nf}$-A/B-$R_{2/3/4}$ (2 pmol/ul) | 1.0 ul |
| Promega Taq (5U/ul) | 0.2 ul |
| DNA (about 20 ng/ul) | 5.0 ul |
| dd$H_2$O | 10.8 ul |
| Total | 25.0 ul |

The PCR reaction system for HLA-DRB1 was as followed:

| | |
|---|---|
| Promega 5x buffer I (Mg2+ plus) | 5.0 ul |
| dNTP Mixture (2.5 mM/μl each) | 2.0 ul |
| $PI_{nf}$-D2-F1 (2 pmol/ul) | 1.0 ul |
| $PI_{nf}$-D2-F2 (2 pmol/ul) | 1.0 ul |
| $PI_{nf}$-D2-F3 (2 pmol/ul) | 1.0 ul |
| $PI_{nf}$-D2-F4 (2 pmol/ul) | 1.0 ul |
| $PI_{nf}$-D2-F5 (2 pmol/ul) | 1.0 ul |
| $PI_{nf}$-D2-F6 (2 pmol/ul) | 1.0 ul |
| $PI_{nf}$-D2-F7 (2 pmol/ul) | 1.0 ul |
| $PI_{nr}$-D2-R (2 pmol/ul) | 1.0 ul |
| Promega Taq (5U/ul) | 0.2 ul |
| DNA (about 20 ng/ul) | 5.0 ul |
| dd$H_2$O | 4.8 ul |
| Total | 25.0 ul |

Wherein $PI_{nf}$-A/B/D2-$F_{1/2/3/4/5/6/7}$ represents the F primer of HLA-A/B/DRB1 having the forward primer index sequence No. n (Table 6) at 5' end, $PI_{nr}$-A/B/D2-$R_{2/3/4}$ represents the R primer of HLA-A/B/DRB1 having the reverse primer index sequence No. n at 5' end (here n≤95), and the rest may be deduced similarly. Moreover, each sample corresponds to a specific set of PCR primers ($PI_{nf}$-A/B/D2-$F_{1/2/3/4/5/6/7}$, $PI_{nr}$-A/B/D2-$R_{2/3/4}$).

Figure 2:
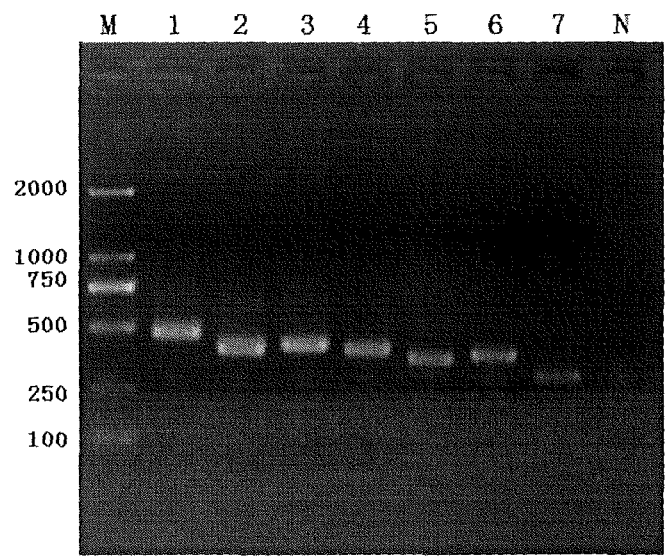

PCR reaction was carried out in PTC-200 PCR apparatus from Bio-Rad Co. After PCR reaction, 2 ul PCR products were subjected to 1% agarose gel electrophoresis. FIG. 2 showed the electrophoretic result of the PCR products of the corresponding exons of HLA-A/B/DRB1 of Sample No. 1, and the marker for DNA molecular weights was DL 2000 (Takara Co.). There were a series of single bands of a length ranging from 300 bp to 500 bp in the electrophorogram, indicating successful PCR amplification of the exons (A2, A3, A4, B2, B3, B4, DRB1-2) of HLA-A/B/DRB1 of Sample No. 1. There was no amplification band in the negative control (N). The results of other samples were similar.

Example 3

Pooling and Purification of PCR Products

20 μl of the rest PCR products was taken from each well of the 96-well plate HLA-P-A2 (except for the negative control), and was mixed homogeneously under shaking in a 3 ml EP tube (designated as HLA-A2-Mix). The same operation was applied to the other 6 96-well plates, designated as HLA-A3-Mix, HLA-A4-Mix, HLA-B2-Mix, HLA-B3-Mix, HLA-B4-Mix and HLA-D2-Mix. 200 ul was taken from each of HLA-A2-Mix, HLA-A3-Mix, HLA-A4-Mix, HLA-B2-Mix, HLA-B3-Mix, HLA-B4-Mix and HLA-D2-Mix, and was mixed in a 3 ml EP tube, designated as HLA-Mix. 500 ul DNA mixture from HLA-Mix was subjected to column purification with Qiagen DNA Purification kit (QIAGEN Co.) (For the specific purification steps, please refer to the manufacturer's instruction). It was determined by Nanodrop 8000 (Thermo Fisher Scientific Co.) that the 200 ul DNA obtained by purification has a HLA-Mix DNA concentration of 48 ng/ul.

Example 4

Shearing of PCR Products, and Construction of Illumina GA PCR-Free Sequencing Libraries 1. DNA Shearing A total amount of 5 ug DNA, taken from the purified HLA-Mix, was contained in a Covaris microtube with an AFA fiber and Snap-Cap and was subjected to the shearing in Covaris S2DNA Shearer (Covaris Co.). The shearing conditions were as followed:

Frequency Sweeping

| | |
|---|---|
| Duty Cycle | 10% |
| Intensity | 5 |
| Cycles/Burst | 200 |
| Time (second) | 300 |

2. Purification after Shearing

All the sheared products of HLA-Mix were recovered and purified by QIAquick PCR Purification Kit, and were dissolved in 37.5 ul EB (QIAGEN Elution Buffer), respectively.

3. Terminal Repairing Reaction

The purified HLA-Mix after the shearing was subject to DNA terminal repairing reaction, and the reaction system was as followed (all the agents were purchased from Enzymatics Co.):

| | |
|---|---|
| DNA | 37.5 μL |
| $H_2$O | 37.5 μL |
| 10x Polynucleotide Kinase Buffer (B904) | 10 μL |
| dNTP mixture (Solution Set (10 mM each)) | 4 μL |
| T4 DNA Polymerase | 5 μL |
| Klenow Fragment | 1 μL |
| T4 Polynucleotide Kinase | 5 μL |
| Total volume | 100 μL |

Reaction conditions: incubating at 20° for 30 min in a Thermomixer (Thermomixer, Eppendorf Co.).

The reaction products were recovered and purified by the QIAquick PCR Purification Kit, and were dissolved in 34 μl EB (QIAGEN Elution Buffer).

4. Addition of A at 3' End

A was added to 3' end of the DNA recovered in the last step, and the reaction system was as followed (all the agents were purchased from Enzymatics Co.):

| | |
|---|---|
| DNA obtained in the last step | 32 μL |
| 10x blue buffer | 5 μL |
| dATP (1 mM, GE Co.) | 10 μL |
| Klenow (3'-5' exo-) | 3 μL |
| Total volume | 50 μL |

Reaction conditions: incubating at 37° for 30 min in a Thermomixer (Thermomixer, Eppendorf Co.).

The reaction products were recovered and purified by MiniElute PCR Purification Kit (QIAGEN Co.), and were dissolved in 13 μl EB (QIAGEN Elution Buffer).

5. Ligation of Illumina GA PCR-Free Library Adapter

The term "PCR-Free library adapter" refers to a segment of designed bases, whose main role lies in auxiliary fixation of DNA molecule onto the sequencing chip to and lies in providing the binding sites for universal sequencing primers, wherein PCR-Free library adapter may be directly ligated to the two termini of the DNA fragments in the sequencing library; since no PCR was involved in the introduction of the library adapter, the library adapter was called PCR-Free library adapter.

The products having A added were ligated to the Illumina GA PCR-Free library adapters, and the reaction system was as followed (all the agents were purchased from Illumina Co.):

| | |
|---|---|
| DNA obtained in the last step | 11 μL |
| 2x Rapid ligation buffer | 15 μL |
| PCR-free adapter oligo mix (30 mM) | 1 μL |
| T4 DNA Ligase (Rapid, L603-HC-L) | 3 μL |
| Total volume | 30 μL |

Reaction conditions: incubating at 20° for 15 min in a Thermomixer (Thermomixer, Eppendorf Co.).

The reaction products were purified by Ampure Beads (Beckman Coulter Genomics), and were dissolved in 50 ul deionized water, and the DNA concentration determined by Fluorescence quantitative PCR (QPCR) was as followed:

| | result determined by qPCR (nM) |
|---|---|
| HLA-Mix | 78.90 |

6. Recovery by Gel Slicing

Figure 3:
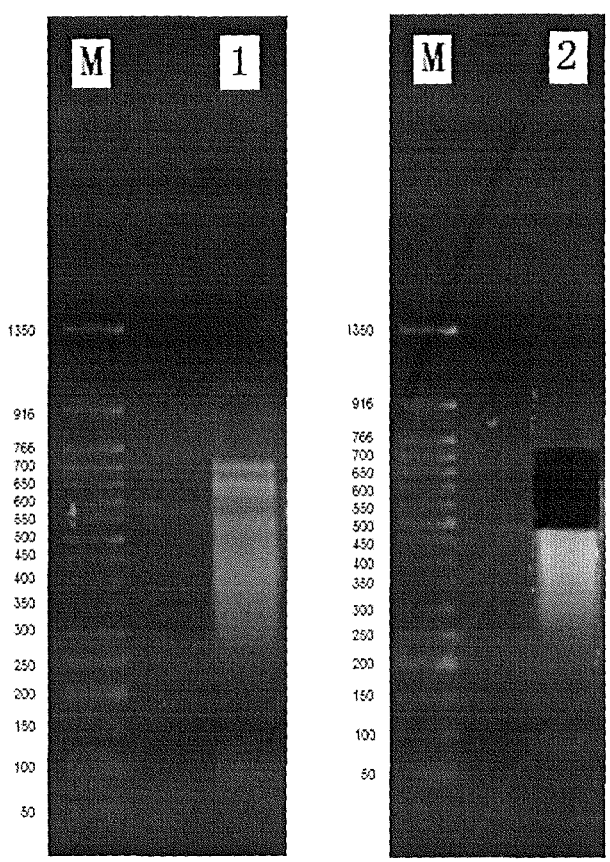
FIG. 3: A drawing illustrating results of DNA electrophoresis after shearing HLA-Mix in Example 4 (before and after gel slicing), wherein the gel-slicing area is the area of 450-750 bp. Lane M is a marker of molecular weight (NEB-50 bp DNA Ladder), and Lane 1 shows the electrophoretic result of HLA-Mix before gel slicing, and Lane 2 is a drawing showing the gel of HLA-Mix after slicing.

30 μL HLA-Mix was subjected to 2% low melting point agarose gel electrophoresis. The electrophoretic condition was 100V, 100 min. DNA marker was the 50 bp DNA marker from NEB Co. The gel containing the DNA fragments ranging from 450 to 750 bp was sliced (FIG. 3). The products in the sliced gel were recovered and purified by QIAquick PCR Purification Kit (QIAGEN Co.), the volume after purification was 32 ul, and the DNA concentration measured by Fluorescence quantitative PCR (QPCR) was 10.16 nM.

Example 5

Illumina GA Sequencing

According to the results of QPCR, 10 pmol DNA was taken and subjected to the sequencing by Illumina GA PE-100 program. For the specific operation procedure, please refer to the Illumina GA operation instruction (Illumina GA IIx).

Example 6

Analysis of the Results

Figures 4, 5:
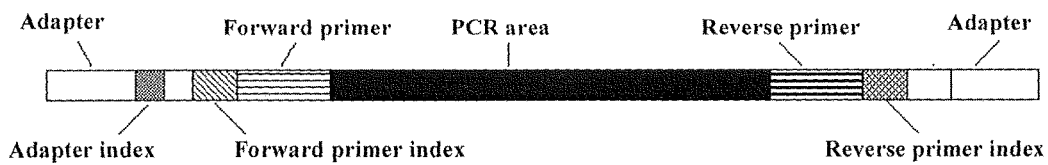
FIG. 4: A screen-capture of the program for construction of consensus sequence of Sample No. 1 in Example 6, illustrating assembling the complete sequence of the PCR products based on primer indexes and the overlapping relationship between DNA fragments. One could find the results of all the coding sequence of A*02:03:01 A*11:01:01 in the result output column on the left, wherein the sequence of Exon 2 is identical to the original known result of Template 1. The Reference sequence A*01:01:01:01 is identified as SEQ ID NO: 245. The upper Assembled Sequence A*02:03:01 is SEQ ID NO: 246. The lower Assembled Sequence A*11:01:01 is SEQ ID NO: 247.
FIG. 5: A drawing illustrating the PCR product after labeling with primer indexes and an adapter index. During experimentation, primer indexes are introduced to the two termini of the PCR product of each sample by PCR simultaneously; multiple PCR products carrying different primer indexes are pooled together to construct a sequencing library. During construction of sequencing libraries, when multiple sequencing libraries have to be constructed, the sequencing libraries may be labeled with the library adapters carrying different adapter indexes. After finishing the construction of libraries, multiple sequencing libraries labeled with different adapter indexes are pooled together and are sequenced by Illumina GA simultaneously (the primer indexes may be identical among sequencing libraries labeled with different adapter indexes). After getting the sequencing results, DNA sequence information for each sample may be obtained by screening the sequence information of the adapter indexes and the primer indexes in the sequencing results.

The sequencing results from Illumina GA were a series of DNA sequences, and by searching the forward and reverse primer index sequences and primer sequences in the sequencing results, databases comprising the sequencing results of the PCR products of various exons of HLA-A/B/DRB 1 for each sample corresponding to respective primer index were constructed. The sequencing results of each exon were aligned to the reference sequence of the corresponding exon by BWA (Burrows-Wheeler Aligner), and meanwhile, the consensus sequences of each database were constructed, and the DNA sequences in the database were selected and corrected. The corrected DNA sequences were assembled into the corresponding sequences of exons of HLA-A/B/DRB 1 on the basis of sequence overlapping and linkage (Paired-End linkage) relationship. The resultant DNA sequence was aligned with the sequence database of the corresponding exon of HLA-A/B/DRB1 in IMGT HLA professional database. If the result of sequence alignment shows 100% match, the HLA-A/B/DRB 1 genotype of the corresponding sample was determined. Please refer to the screen-capture of the program for construction of consensus sequence of Exon 2 of HLA-A site in Sample No. 1 as illustrated in FIG. 4.

For all 95 samples, the typing results obtained by the above method were completely consistent with the known typing results, wherein the results of Samples No. 1-32 were as followed:

| Sample No. | Original known HLA-A/B/DRB1 type | | | | | |
|---|---|---|---|---|---|---|
| 1 | A*02: 03 | A*11: 01 | B*38: 02 | B*48: 01 | DRB1*14: 54 | DRB1*15: 01 |
| 2 | A*01: 01 | A*30: 01 | B*08: 01 | B*13: 02 | DRB1*03: 01 | DRB1*07: 01 |
| 3 | A*01: 01 | A*02: 01 | B*15: 11 | B*47: 01 | DRB1*13: 02 | DRB1*15: 01 |
| 4 | A*24: 08 | A*26: 01 | B*40: 01 | B*51: 01 | DRB1*04: 04 | DRB1*09: 01 |
| 5 | A*01: 01 | A*24: 02 | B*54: 01 | B*55: 02 | DRB1*04: 05 | DRB1*09: 01 |
| 6 | A*01: 01 | A*03: 02 | B*15: 11 | B*37: 01 | DRB1*10: 01 | DRB1*14: 54 |
| 7 | A*11: 01 | A*30: 01 | B*13: 02 | B*15: 18 | DRB1*04: 04 | DRB1*07: 01 |
| 8 | A*01: 01 | A*02: 01 | B*35: 03 | B*81: 01 | DRB1*11: 01 | DRB1*15: 01 |
| 9 | A*02: 06 | A*31: 01 | B*27: 07 | B*40: 02 | DRB1*03: 01 | DRB1*13: 02 |
| 10 | A*01: 01 | A*66: 01 | B*37: 01 | B*49: 01 | DRB1*10: 01 | DRB1*13: 02 |
| 11 | A*01: 01 | A*03: 01 | B*35: 01 | B*52: 01 | DRB1*01: 01 | DRB1*15: 02 |
| 12 | A*11: 01 | A*11: 01 | B*15: 01 | B*15: 05 | DRB1*04: 06 | DRB1*15: 01 |
| 13 | A*01: 01 | A*11: 02 | B*07: 02 | B*15: 02 | DRB1*09: 01 | DRB1*15: 01 |
| 14 | A*01: 01 | A*02: 01 | B*52: 01 | B*67: 01 | DRB1*15: 02 | DRB1*16: 02 |
| 15 | A*01: 01 | A*02: 05 | B*15: 17 | B*50: 01 | DRB1*07: 01 | DRB1*15: 01 |
| 16 | A*01: 01 | A*11: 01 | B*37: 01 | B*40: 02 | DRB1*10: 01 | DRB1*12: 02 |
| 17 | A*24: 07 | A*32: 01 | B*35: 05 | B*40: 01 | DRB1*03: 01 | DRB1*04: 05 |
| 18 | A*11: 01 | A*24: 02 | B*13: 01 | B*35: 01 | DRB1*16: 02 | DRB1*16: 02 |
| 19 | A*11: 01 | A*11: 01 | B*40: 02 | B*55: 12 | DRB1*04: 05 | DRB1*15: 01 |
| 20 | A*02: 11 | A*24: 02 | B*40: 01 | B*40: 06 | DRB1*11: 01 | DRB1*15: 01 |
| 21 | A*01: 01 | A*02: 06 | B*51: 01 | B*57: 01 | DRB1*07: 01 | DRB1*12: 01 |
| 22 | A*01: 01 | A*29: 01 | B*07: 05 | B*15: 01 | DRB1*04: 05 | DRB1*07: 01 |
| 23 | A*01: 01 | A*02: 07 | B*37: 01 | B*46: 01 | DRB1*04: 03 | DRB1*10: 01 |
| 24 | A*24: 85 | A*30: 01 | B*13: 02 | B*55: 02 | DRB1*07: 01 | DRB1*15: 01 |
| 25 | A*11: 01 | A*31: 01 | B*07: 06 | B*51: 01 | DRB1*12: 02 | DRB1*14: 05 |
| 26 | A*01: 01 | A*11: 01 | B*46: 01 | B*57: 01 | DRB1*07: 01 | DRB1*08: 03 |
| 27 | A*01: 01 | A*02: 01 | B*15: 18 | B*37: 01 | DRB1*04: 01 | DRB1*15: 01 |
| 28 | A*01: 01 | A*24: 02 | B*37: 01 | B*46: 01 | DRB1*09: 01 | DRB1*10: 01 |

-continued

| Sample No. | Original known HLA-A/B/DRB1 type | | | | | |
|---|---|---|---|---|---|---|
| 29 | A*26: 01 | A*66: 01 | B*40: 40 | B*41: 02 | DRB1*12: 01 | DRB1*15: 01 |
| 30 | A*02: 01 | A*29: 02 | B*13: 02 | B*45: 01 | DRB1*03: 01 | DRB1*12: 02 |
| 31 | A*01: 01 | A*11: 03 | B*15: 01 | B*57: 01 | DRB1*07: 01 | DRB1*15: 01 |
| 32 | A*11: 01 | A*26: 01 | B*35: 03 | B*38: 01 | DRB1*11: 03 | DRB1*14: 04 |

| Sample No. | The determined HLA-A/B/DRB1 type | | | | | |
|---|---|---|---|---|---|---|
| 1 | A*02: 03 | A*11: 01 | B*38: 02 | B*48: 01 | DRB1*14: 54 | DRB1*15: 01 |
| 2 | A*01: 01 | A*30: 01 | B*08: 01 | B*13: 02 | DRB1*03: 01 | DRB1*07: 01 |
| 3 | A*01: 01 | A*02: 01 | B*15: 11 | B*47: 01 | DRB1*13: 02 | DRB1*15: 01 |
| 4 | A*24: 08 | A*26: 01 | B*40: 01 | B*51: 01 | DRB1*04: 04 | DRB1*09: 01 |
| 5 | A*01: 01 | A*24: 02 | B*54: 01 | B*55: 02 | DRB1*04: 05 | DRB1*09: 01 |
| 6 | A*01: 01 | A*03: 02 | B*15: 11 | B*37: 01 | DRB1*10: 01 | DRB1*14: 54 |
| 7 | A*11: 01 | A*30: 01 | B*13: 02 | B*15: 18 | DRB1*04: 04 | DRB1*07: 01 |
| 8 | A*01: 01 | A*02: 01 | B*35: 03 | B*81: 01 | DRB1*11: 01 | DRB1*15: 01 |
| 9 | A*02: 06 | A*31: 01 | B*27: 07 | B*40: 02 | DRB1*03: 01 | DRB1*13: 02 |
| 10 | A*01: 01 | A*66: 01 | B*37: 01 | B*49: 01 | DRB1*10: 01 | DRB1*13: 02 |
| 11 | A*01: 01 | A*03: 01 | B*35: 01 | B*52: 01 | DRB1*01: 01 | DRB1*15: 02 |
| 12 | A*11: 01 | A*11: 01 | B*15: 01 | B*15: 05 | DRB1*04: 06 | DRB1*15: 01 |
| 13 | A*01: 01 | A*11: 02 | B*07: 02 | B*15: 02 | DRB1*09: 01 | DRB1*15: 01 |
| 14 | A*01: 01 | A*02: 01 | B*52: 01 | B*67: 01 | DRB1*15: 02 | DRB1*16: 02 |
| 15 | A*01: 01 | A*02: 05 | B*15: 17 | B*50: 01 | DRB1*07: 01 | DRB1*15: 01 |
| 16 | A*01: 01 | A*11: 01 | B*37: 01 | B*40: 02 | DRB1*10: 01 | DRB1*12: 02 |
| 17 | A*24: 07 | A*32: 01 | B*35: 05 | B*40: 01 | DRB1*03: 01 | DRB1*04: 05 |
| 18 | A*11: 01 | A*24: 02 | B*13: 01 | B*35: 01 | DRB1*16: 02 | DRB1*16: 02 |
| 19 | A*11: 01 | A*11: 01 | B*40: 02 | B*55: 12 | DRB1*04: 05 | DRB1*15: 01 |
| 20 | A*02: 11 | A*24: 02 | B*40: 01 | B*40: 06 | DRB1*11: 01 | DRB1*15: 01 |
| 21 | A*01: 01 | A*02: 06 | B*51: 01 | B*57: 01 | DRB1*07: 01 | DRB1*12: 01 |
| 22 | A*01: 01 | A*29: 01 | B*07: 05 | B*15: 01 | DRB1*04: 05 | DRB1*07: 01 |
| 23 | A*01: 01 | A*02: 07 | B*37: 01 | B*46: 01 | DRB1*04: 03 | DRB1*10: 01 |
| 24 | A*24: 85 | A*30: 01 | B*13: 02 | B*55: 02 | DRB1*07: 01 | DRB1*15: 01 |
| 25 | A*11: 01 | A*31: 01 | B*07: 06 | B*51: 01 | DRB1*12: 02 | DRB1*14: 05 |
| 26 | A*01: 01 | A*11: 01 | B*46: 01 | B*57: 01 | DRB1*07: 01 | DRB1*08: 03 |
| 27 | A*01: 01 | A*02: 01 | B*15: 18 | B*37: 01 | DRB1*04: 01 | DRB1*15: 01 |
| 28 | A*01: 01 | A*24: 02 | B*37: 01 | B*46: 01 | DRB1*09: 01 | DRB1*10: 01 |
| 29 | A*26: 01 | A*66: 01 | B*40: 40 | B*41: 02 | DRB1*12: 01 | DRB1*15: 01 |
| 30 | A*02: 01 | A*29: 02 | B*13: 02 | B*45: 01 | DRB1*03: 01 | DRB1*12: 02 |
| 31 | A*01: 01 | A*11: 03 | B*15: 01 | B*57: 01 | DRB1*07: 01 | DRB1*15: 01 |
| 32 | A*11: 01 | A*26: 01 | B*35: 03 | B*38: 01 | DRB1*11: 03 | DRB1*14: 04 |

Note:
among HLA-DRB1 types, DRB1*1201 does not exclude the possibility of DRB1*1206/1210/1217, and DRB1*1454 does not exclude the possibility of DRB1*1401, because said alleles were completely identical in the sequence of Exon 2 of HLA-DRB1.

Example 7

HLA-A,B and DRB1 genotyping by using the second generation sequencing technique (Illumina GA)

Sample Extraction

DNAs were extracted from 950 blood samples with known HLA-SBT typing results (China Marrow Donor Program cited hereafter as (CMDP)) by using KingFisher Automatic Extraction Instrument (US Thermo Co.). The method was as described in Example 1.

PCR Amplification

The 950 DNAs obtained from the sample extraction step were designated as No. 1-950, and were divided into 10 groups (95 DNAs for each), which were designated as HLA-1, HLA-2, HLA-3, HLA-4, HLA-5, HLA-6, HLA-7, HLA-8, HLA-9, HLA-10. For each group of samples, 95 DNA samples were amplified by 95 sets of PCR primers (Table 1) carrying bidirectional primer indexes (Table 6) for amplification of Exons 2, 3, 4 of HLA-A/B and PCR primers (Table 7) carrying bidirectional primer indexes (Table 6) for amplification of Exon 2 of HLA-DRB1. PCR reaction took place in 96-well plates, using 70 plates in total, designated as HLA-X-P-A2, HLA-X-P-A3, HLA-X-P-A4, HLA-X-P-B2, HLA-X-P-B3, HLA-X-P-B4 and HLA-X-P-DRB1-2 ("X" represents the information of the group number 1/2/3/4/5/6/7/8/9/10, "A2/3/4", "B2/3/4", "DRB1-2" represent the amplification sites), wherein a negative control without adding any template was set in each plate, and the primers used for the negative control were primers labeled by PI-1 (Table 6). During experimentation, the information of each sample on the group number and primer indexes was recorded. The method was as described in Example 2.

Pooling and Purification of PCR Products

For samples of Group X ("X" is 1/2/3/4/5/6/7/8/9/10), 20 μl of rest PCR products was taken from each well of the 96-well plate HLA-X-P-A2 (except for the negative control), and was mixed homogeneously under shaking in a 3 ml EP tube (designated as HLA-X-A2-Mix). The same operation was applied to the other 6 96-well plates of the samples of Group X, designated as HLA-X-A3-Mix, HLA-X-A4-Mix, HLA-X-B2-Mix, HLA-X-B3-Mix, HLA-X-B4-Mix and HLA-X-D2-Mix. 200 ul was taken from each of HLA-X-A2-Mix, HLA-X-A3-Mix, HLA-X-A4-Mix, HLA-X-B2-Mix, HLA-X-B3-Mix, HLA-X-B4-Mix and HLA-X-D2-Mix, and was mixed in a 3 ml EP tube, designated as HLA-X-Mix. 500 ul DNA mixture from HLA-X-Mix was subjected to column purification with Qiagen DNA Purification kit (QIAGEN Co.) (For the specific purification steps, please refer to the manufacturer's instruction) to obtain 200 ul DNA, and its DNA concentration was determined by Nanodrop 8000 (Thermo Fisher Scientific Co.). The same operation was also applied to other groups. The finally determined DNA concentrations were as followed.

|  | HLA-1-Mix | HLA-2-Mix | HLA-3-Mix | HLA-4-Mix | HLA-5-Mix | HLA-6-Mix | HLA-7-Mix | HLA-8-Mix | HLA-9-Mix | HLA-10-Mix |
|---|---|---|---|---|---|---|---|---|---|---|
| concentration (ng/ul) | 48.0 | 52.1 | 49.3 | 50.2 | 47.6 | 48.5 | 49.1 | 48.6 | 51.3 | 50.8 |

The method was as described in Example 3.

The construction of Illumina GA Sequencing libraries was performed by the method of Example 4. The corresponding relationships between the sample groups and the library adapters were as followed.

| | Sample group No. | | | | | | | | | |
|---|---|---|---|---|---|---|---|---|---|---|
| | HLA-1 | HLA-2 | HLA-3 | HLA-4 | HLA-5 | HLA-6 | HLA-7 | HLA-8 | HLA-9 | HLA-10 |
| Library adapter No. | 1 | 2 | 3 | 4 | 5 | 6 | 7 | 8 | 9 | 10 |

The reaction products were purified by Ampure Beads (Beckman Coulter Genomics), and were dissolved in 50 ul deionized water, and the DNA molar concentrations determined by Fluorescence quantitative PCR (QPCR) were as followed:

|  | HLA-1-Mix | HLA-2-Mix | HLA-3-Mix | HLA-4-Mix | HLA-5-Mix | HLA-6-Mix | HLA-7-Mix | HLA-8-Mix | HLA-9-Mix | HLA-10-Mix |
|---|---|---|---|---|---|---|---|---|---|---|
| Conc. (nM) | 78.90 | 72.13 | 79.33 | 80.21 | 77.68 | 78.50 | 89.12 | 78.60 | 81.32 | 80.82 |

Recovery by Gel Slicing

HLA-1-Mix, HLA-2-Mix, HLA-3-Mix, HLA-4-Mix, HLA-5-Mix, HLA-6-Mix, HLA-7-Mix, HLA-8-Mix, HLA-9-Mix and HLA-10-Mix were mixed at an equal mole (final concentration was 72.13 nM/ul), designated as HLA-Mix-10. 30 μL HLA-Mix-10 was subjected to 2% low melting point agarose gel electrophoresis. The electrophoretic condition was 100V, 100 min. DNA marker was the 50 bp DNA marker from NEB Co. The gel containing the DNA fragments ranging from 450 to 750 bp was sliced. The products in the sliced gel were recovered and purified by QIAquick PCR Purification Kit (QIAGEN Co.), the volume after purification was 32 ul, and the DNA concentration measured by Fluorescence quantitative PCR (QPCR) was 9.96 nM.

The sequencing and result analysis were performed as described in Examples 5 and 6. For all 950 samples, the typing results obtained by the above method were completely consistent with the known typing results.

Example 8

HLA-C Genotyping by Using the Second Generation Sequencing Technique (Illumina GA)
1. DNA Sample Extraction
The steps were as described in Example 1.
2. PCR Amplification
The steps were as described in Example 2, except that the PCR primers used were PCR primers for Exons 2, 3 and 4 of HLA-C, as shown in Table 3.

95 sets of PCR index primers were used to amplify 95 DNA samples, respectively, wherein each set of PCR index primers consisted of PCR primers for amplification of Exons 2, 3, 4 of HLA-C (Table 3) and a pair of bidirectional primer indexes (as described below), each forward PCR primer has the forward primer index of a pair of primer indexes linked at the 5' end, and the reverse PCR primer has the reverse primer index of a pair of primer indexes linked at the 5' end, During the synthesis of primers, the primer indexes were directly added to the 5' end of the PCR primers.

The 95 DNAs obtained from the sample extraction step were designated as No. 1-95. PCR reaction took place in 96-well plates, 3 plates in total, designated as HLA-P-C2, HLA-P-C3, HLA-P-A4 (C2/3/4 represent the amplification sites), wherein a negative control without adding any template was set in each plate, and the primers used in the negative control were the same as the primer PI-96. During experimentation, the numbering information of the sample corresponding to each pair of primer indexes was recorded.

The primer indexes used were the primer indexes PI-1 to PI-95 as listed in Table 6, and the following negative control primer index PI-96 (Table 8)

TABLE 8

Relevant information of the primer index used for the negative control

| PI-96 | CACTGTATAGCT | CGACTAGTACTA | H12 | Negative control |
|---|---|---|---|---|

The DNAs, extracted by using KingFisher Automatic Extraction Instrument in step 1, were used as the templates, and PCR amplification was carried out in single tubes by using primers for exons of HLA-C, wherein the primers have indexes at 5' end. PCR procedure was as followed:

C2: 96° 2 min
95° 30 s→62° 30 s→72° 20 s (35 cycles)
15° ∞
C3: 96° 2 min
95° 30 s→56° 30 s→72° 20 s (35 cycles)
15° ∞
C4: 96° 2 min
95° 30 s→60° 30 s→72° 20 s (35 cycles)
15° ∞

PCR reaction system of HLA-C was as followed:

| | |
|---|---|
| Promega 5x buffer I (Mg2+ plus) | 5.0 μL |
| dNTP mixture (2.5 mM each) | 2.0 μL |
| PInr-C-F2/3/4 (50 ng/ul) | 1.5 μL |
| PInf-C-R2/3/4 (50 ng/ul) | 1.5 μL |
| Promega Taq (5 U/ul) | 0.2 μL |
| DNA (about 20 ng/ul) | 2.0 μL |
| ddH$_2$O | 12.8 μL |
| Total | 25.0 μL |

Wherein, $PI_{nf}$-C-$F_{2/3/4}$ represents the F primer of HLA-C having the forward primer index sequence No. n (Table 2) at 5' end, $PI_{nr}$-C-$R_{2/3/4}$ represents the R primer of HLA-C having the reverse primer index sequence No. n at 5' end (here n≤96), and the rest may be deduced similarly. Moreover, each sample corresponds to a specific set of PCR primers.

Figure 6:
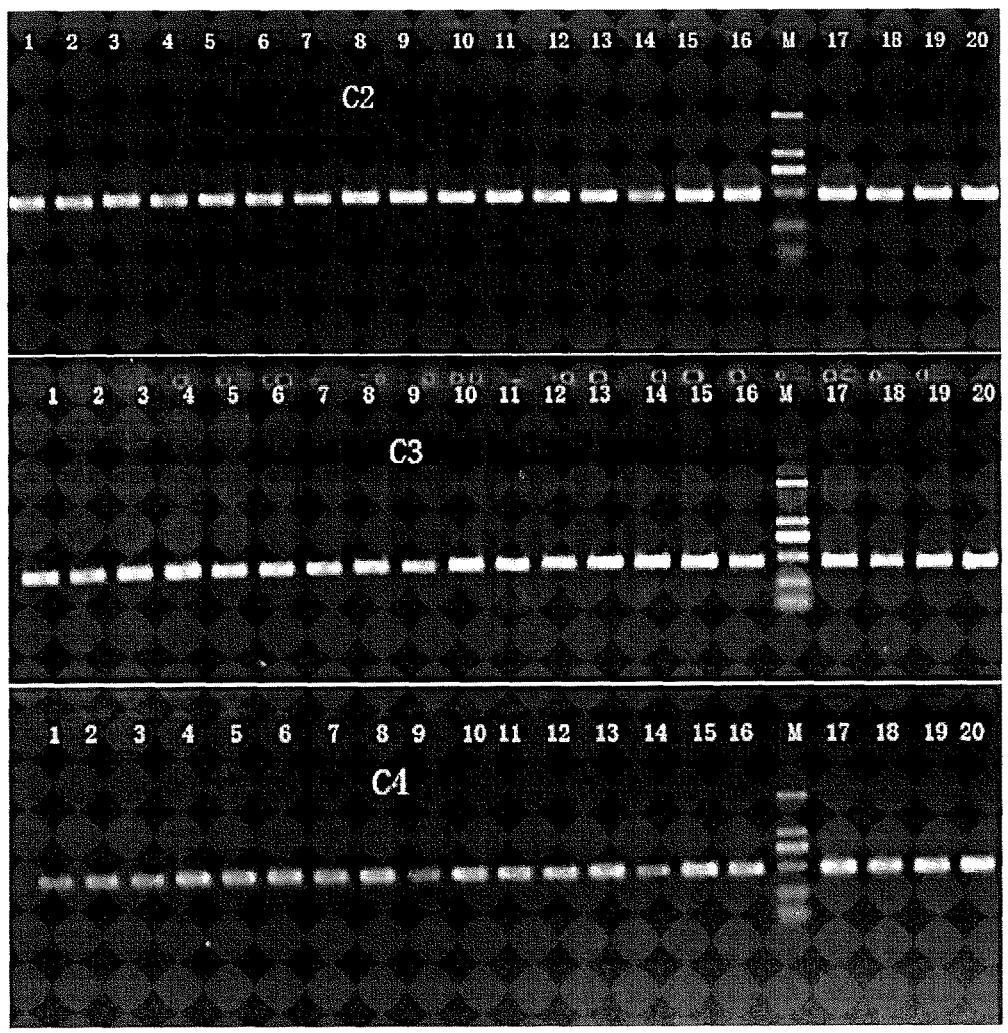
FIG. 6: A drawing illustrating the electrophoretic result of the PCR products of Exons 2, 3, 4 of HLA-C of some samples in Example 8. It can be seen from electrophoretogram that PCR products are a series of single bands of 400 bp-500 bp, wherein Lane M is reference for standard DNA molecular weights (DL 2000, Takara Co.).

PCR reaction was carried out in PTC-200 PCR apparatus from Bio-Rad Co. After PCR reaction, 2 ul PCR products were subjected to 1.5% agarose gel electrophoresis. FIG. 6 showed the electrophoretic result of the PCR products of the corresponding exons of HLA-C of the first 20 samples, and the DNA molecular marker was DL 2000 (Takara Co.). There were a series of single bands of a length ranging from 400 bp to 500 bp in the electrophorogram, indicating successful PCR amplification of exons (C2, C3, C4) of HLA-C of the samples. The results of other samples were similar.

Pooling and Purification of PCR Products

20 μl of the rest PCR products was taken from each well of the 96-well plate HLA-P-C2 (except for the negative control), and was pooled homogeneously under shaking in a 3 ml EP tube (designated as HLA-C2-Mix). The same operation was applied to the other 2 96-well plates, designated as HLA-C3-Mix and HLA-C4-Mix. 200 ul was taken from each of HLA-C2-Mix, HLA-C3-Mix and HLA-C4-Mix, and was mixed in a 1.5 ml EP tube, designated as HLA-Mix. 500 ul DNA mixture from HLA-Mix was subjected to column purification with Qiagen DNA Purification kit (QIAGEN Co.) (For the specific purification steps, please refer to the manufacturer's instruction). It was determined by Nanodrop 8000 (Thermo Fisher Scientific Co.) that the 200 ul DNA obtained by purification has a HLA-Mix DNA concentration of 50 ng/ul.

4. Construction of Illumina GA PCR-Free Sequencing Libraries 4.1 Shearing of PCR Products A total amount of 5 μg DNA, taken from the purified HLA-Mix, was contained in a Covaris microtube with AFA fiber and Snap-Cap and was subjected to the shearing in Covaris S2 (Covaris Co.). The shearing conditions were as followed:

Frequency Sweeping

| | |
|---|---|
| Duty Cycle | 10% |
| Intensity | 3 |
| Cycles/Burst | 200 |
| Time (s) | 180 |

4.2 Purification of the Sheared PCR Products

All the sheared products of HLA-Mix were recovered and purified by QIAquick PCR Purification Kit, and were dissolved in 37.5 ul EB (QIAGEN Elution Buffer), respectively.

4.3 Terminal Repairing Reaction

The purified products were subject to DNA terminal repairing reaction, the reaction system was as followed (all the agents were purchased from Enzymatics Co.):

| | |
|---|---|
| Products purified in the last step | 37.5 μL |
| 10x Polynucleotide Kinase Buffer (B904) | 5 μL |
| dNTP mixture (Solution Set (10 mM each)) | 2 μL |
| T4 DNA Polymerase | 2.5 μL |
| Klenow Fragment | 0.5 μL |
| T4 Polynucleotide Kinase | 2.5 μL |
| Total volume | 50 μL |

Reaction conditions: incubating at 20° for 30 min in a Thermomixer (Thermomixer, Eppendorf Co.).

The reaction products were recovered and purified by the QIAquick PCR Purification Kit, and were dissolved in 32 μl EB (QIAGEN Elution Buffer).

4.4 Addition of A at 3' End

A was added to 3' end of the DNA recovered in the last step, and the reaction system was as followed (all the agents were purchased from Enzymatics Co.):

| | |
|---|---|
| DNA obtained in the last step | 32 μL |
| 10x blue buffer | 5 μL |
| dATP (1 mM, GE Co.) | 10 μL |
| Klenow (3'-5' exo-) | 3 μL |
| Total volume | 50 μL |

Reaction conditions: incubating at 37° for 30 min in a Thermomixer (Thermomixer, Eppendorf Co.).

The reaction products were recovered and purified by MiniElute PCR Purification Kit (QIAGEN Co.), and were dissolved in 38 μl EB (QIAGEN Elution Buffer).

4.5 Ligation of Illumina GA PCR-Free Library Adapter

The products having A added were ligated to the Illumina GA PCR-Free library adapters, and the reaction system was as followed (all the agents were purchased from Illumina Co.):

| | |
|---|---|
| DNA obtained in the last step | 38 μL |
| 10x Ligation buffer | 5 μL |
| PCR-free adapter oligo mix (30 mM) | 2 μL |
| T4 DNA Ligase (Rapid, L603-HC-L) | 5 μL |
| Total volume | 50 μL |

Reaction conditions: incubating at 16° overnight in a Thermomixer (Thermomixer, Eppendorf Co.).

The reaction products were purified by Ampure Beads (Beckman Coulter Genomics), and were dissolved in 50 ul deionized water, and the DNA concentration determined by Fluorescence quantitative PCR (QPCR) was as followed:

| | result determined by qPCR (nM) |
|---|---|
| HLA-Mix | 122.71 |

4.6 Recovery by Gel Slicing

Figure 7:
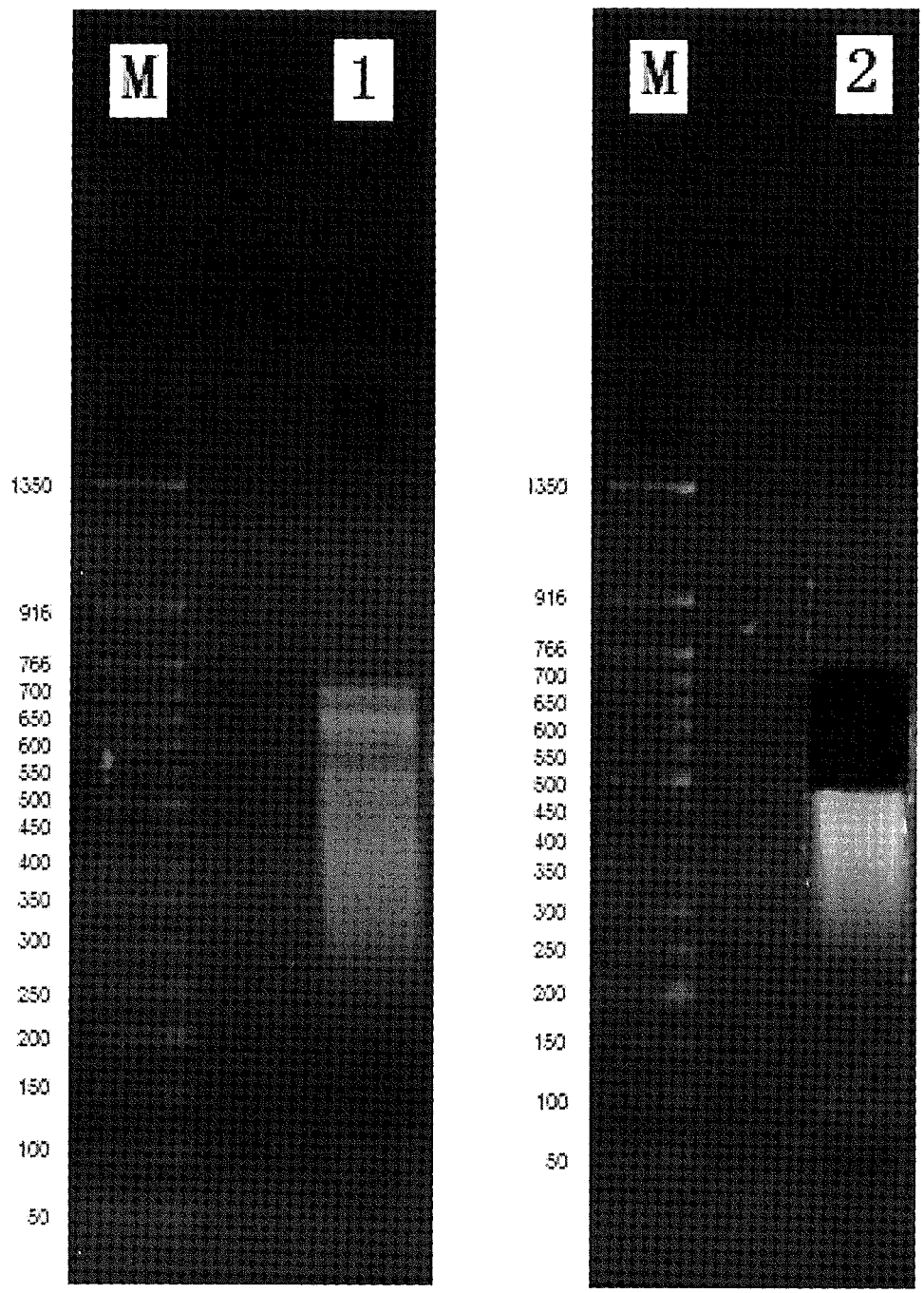
FIG. 7: A drawing illustrating results of DNA electrophoretic gel slicing after shearing HLA-Mix in Example 8, wherein the gel-slicing area is the area of 450-750 bp. Lane M is a marker of molecular weight (NEB-50 bp DNA Ladder), and Lane 1 is a drawing showing the gel of HLA-Mix before slicing, and Lane 2 is a drawing showing the gel of HLA-Mix after slicing.

30 μL HLA-Mix was subjected to 2% low melting point agarose gel electrophoresis. The electrophoretic condition was 100V, 100 min. DNA marker was the 50 bp DNA Ladder from NEB Co. The gel containing the DNA fragments ranging from 400 to 750 bp was sliced (FIG. 7). The products in the sliced gel were recovered and purified by QIAquick PCR Purification Kit (QIAGEN Co.), the volume after purification was 32 ul, and the DNA concentration measured by Fluorescence quantitative PCR (QPCR) was 17.16 nM.

5. Illumina GA Sequencing

According to the detection results of QPCR, 10 pmol DNA was taken and subjected to the sequencing by Illumina GA PE-100 program. For the specific operation procedure, please refer to the Illumina GA operation instruction (Illumina GA IIx).

6. Analysis of the Results

Figure 8:
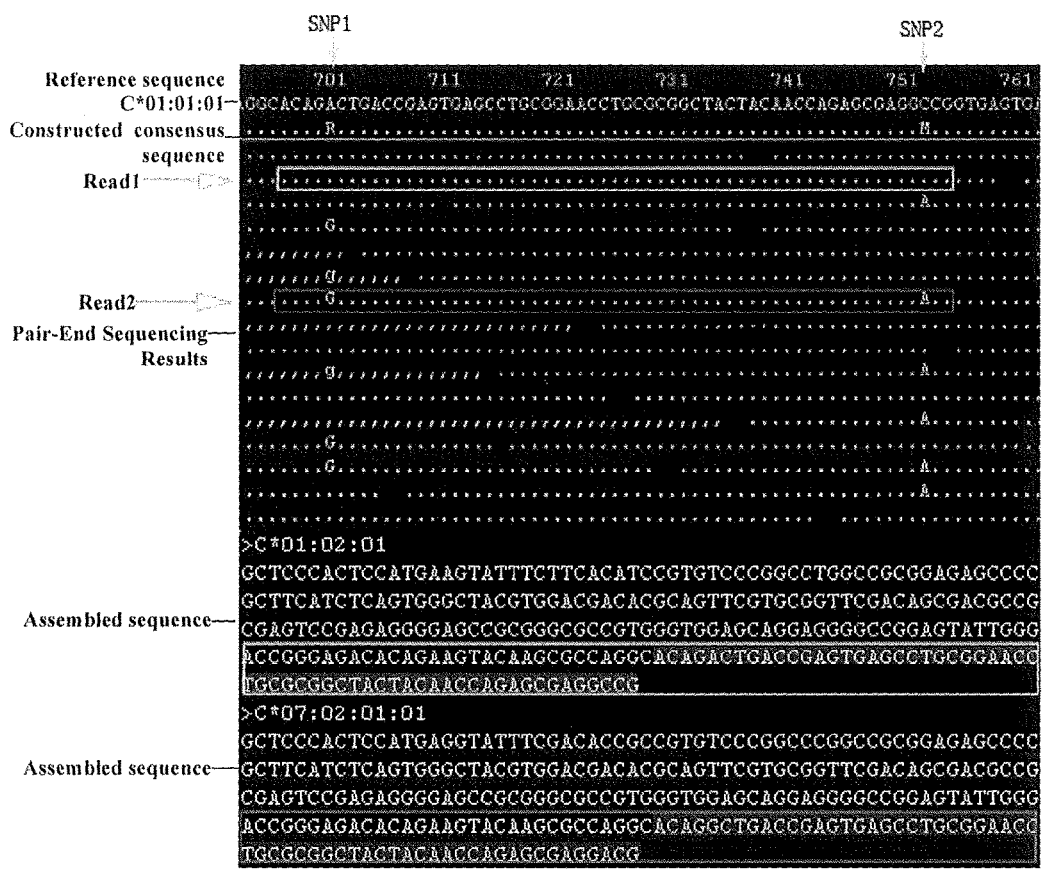
FIG. 8: A screen-capture of the program for construction of consensus sequence of Exon 2 of HLA-C site of Sample No. 2 in Example 8. Firstly, the sequence reads of C site of the sample are aligned with the reference sequence by BWA software, thereby constructing the consensus sequences of Exons 2, 3, 4 of C site of the sample; further, the haplotype sequence of each exon of C site is determined on the basis of the linkage relationship between SNPs; and finally the type of the sample is determined by the intersection of the haplotype sequences of the exons. As shown in the figure, two heterozygous SNP are comprised in 695-764 area of C gene sequence of sample No. 2, and it can be determined from read1 and read2 that the linkage relationship of SNP is A-C, G-A (" . . . " in the figure represents the bases identical to those of the reference sequence). The sequences correspond to the shaded parts of the sequences of the C*010201 and C*07020101 types, respectively. The judgment of the linkage relationship of other areas is similar. The Reference sequence C*01:01:01:01 is SEQ ID NO: 248. The upper Assembled Sequence C*01:02:01 is SEQ ID NO: 249. The lower Assembled Sequence C*07:02:01:01 is SEQ ID NO: 250.

The sequencing results from Iliumina GA were a series of DNA sequences, and by searching the forward and reverse primer index sequences and primer sequences in the sequencing results, databases comprising the sequencing results of the PCR products of various exons of HLA-C for each sample corresponding to respective primer index were constructed were constructed. The sequencing results of each exon was aligned to the reference sequence of the corresponding exon by BWA (Burrows-Wheeler Aligner), and consensus sequences of each database were constructed; and the sequence reads were selected and corrected based on the quality value of base sequencing, and difference between the sequence reads and consensus sequences. The corrected DNA sequences were assembled into the corresponding sequences of exons of HLA-C on the basis of sequence overlapping and linkage (Paired-End linkage) relationship. The screen-capture of FIG. 8 illustrates the procedure for construction of consensus sequence of Exon 2 of HLA-C site in Sample No. 2.

The resultant DNA sequence was aligned with the sequence database of the corresponding exon of HLA-C in IMGT HLA professional database. If the result of sequence alignment showed 100% match, the HLA-C genotype of the corresponding sample was determined. For all 95 samples, the typing results obtained by the above method were completely consistent with the known typing results, wherein the typing results of Samples No. 1-32 were as followed: (as shown in Table 9, all the obtained results were identical to the original known results),

TABLE 9

Comparison of the typing results obtained by the above method with the original known typing results of the samples

| Sample No. | Original known HLA-C genotype | | Results for HLA-C obtained at this time | | Identical or not |
|---|---|---|---|---|---|
| 1 | C*08:01 | C*15:05 | C*08:01 | C*15:05 | yes |
| 2 | C*01:02 | C*07:02 | C*01:02 | C*07:02 | yes |
| 3 | C*08:01 | C*16:02 | C*08:01 | C*16:02 | yes |
| 4 | C*01:02 | C*03:02 | C*01:02 | C*03:02 | yes |
| 5 | C*01:02 | C*02:02 | C*01:02 | C*02:02 | yes |
| 6 | C*01:02 | C*15:02 | C*01:02 | C*15:02 | yes |
| 7 | C*01:02 | C*03:04 | C*01:02 | C*03:04 | yes |
| 8 | C*03:02 | C*07:02 | C*03:02 | C*07:02 | yes |
| 9 | C*06:02 | C*16:02 | C*06:02 | C*16:02 | yes |
| 10 | C*01:02 | C*03:04 | C*01:02 | C*03:04 | yes |
| 11 | C*03:04 | C*07:02 | C*03:04 | C*07:02 | yes |
| 12 | C*07:02 | C*08:01 | C*07:02 | C*08:01 | yes |
| 13 | C*01:02 | C*15:02 | C*01:02 | C*15:02 | yes |
| 14 | C*01:02 | C*03:04 | C*01:02 | C*03:04 | yes |
| 15 | C*01:02 | C*03:04 | C*01:02 | C*03:04 | yes |
| 16 | C*07:02 | C*12:02 | C*07:02 | C*12:02 | yes |
| 17 | C*04:01 | C*08:01 | C*04:01 | C*08:01 | yes |
| 18 | C*08:01 | C*16:02 | C*08:01 | C*16:02 | yes |
| 19 | C*14:02 | C*15:02 | C*14:02 | C*15:02 | yes |
| 20 | C*01:02 | C*03:03 | C*01:02 | C*03:03 | yes |
| 21 | C*03:03 | C*08:01 | C*03:03 | C*08:01 | yes |
| 22 | C*03:04 | C*07:02 | C*03:04 | C*07:02 | yes |
| 23 | C*07:02 | C*08:01 | C*07:02 | C*08:01 | yes |
| 24 | C*07:02 | C*12:02 | C*07:02 | C*12:02 | yes |
| 25 | C*07:02 | C*12:03 | C*07:02 | C*12:03 | yes |
| 26 | C*03:04 | C*08:01 | C*03:04 | C*08:01 | yes |
| 27 | C*01:02 | C*03:04 | C*01:02 | C*03:04 | yes |
| 28 | C*07:02 | C*12:02 | C*07:02 | C*12:02 | yes |
| 29 | C*03:02 | C*07:02 | C*03:02 | C*07:02 | yes |
| 30 | C*01:02 | C*03:03 | C*01:02 | C*03:03 | yes |
| 31 | C*01:02 | C*07:02 | C*01:02 | C*07:02 | yes |
| 32 | C*01:02 | C*07:02 | C*01:02 | C*07:02 | yes |

Note:
among HLA-C types, C*0303 does not exclude the possibility of C*0320N, C*0401 does not exclude the possibility of C*0409N/0430, C*0702 does not exclude the possibility of C*0750, C*0801 does not exclude the possibility of C*0822, C*1505 does not exclude the possibility of C*1529, because said alleles were completely identical in the sequences of Exons 2, 3, 4 of HLA-C.

Example 9: HLA-C Genotyping by Using Sanger Sequencing Method

1. Sample DNA Extraction

As described in Example 1, DNAs were extracted by using KingFisher Automatic Extraction Instrument from 26 out of 95 samples with known HLA genotypes.

2. PCR Amplification

The above DNAs, extracted by using KingFisher Automatic Extraction Instrument, were used as templates, and PCR amplification was carried out in single tubes by using three pairs of PCR primers C-F2/C-R2, C-F3/C-R3, C-F4/C-R4 (Table 3), respectively. The PCR procedure for each pair of primers was as followed:

C2: 96° 2 min
95° 30 s→62° 30 s→72° 20 s (35 cycles)
15° ∞

C3: 96° 2 min
95° 30 s→56° 30 s→72° 20 s (35 cycles)
15° ∞

C4: 96° 2 min
95° 30 s→60° 30 s→72° 20 s (35 cycles)
15° ∞

PCR reaction system of HLA-C was as followed:

| | |
|---|---|
| Promega 5x buffer I (Mg2+ plus) | 5.0 μL |
| dNTP Mixture (2.5 mM each) | 2.0 μL |
| Primer mix (50 ng/μL) | 3.0 μL |
| Promega Taq (5 U/μL) | 0.2 μL |
| DNA (about 20 ng/μL) | 2.0 μL |
| ddH$_2$O | 12.8 μL |
| total | 25.0 μL |

Figure 9:
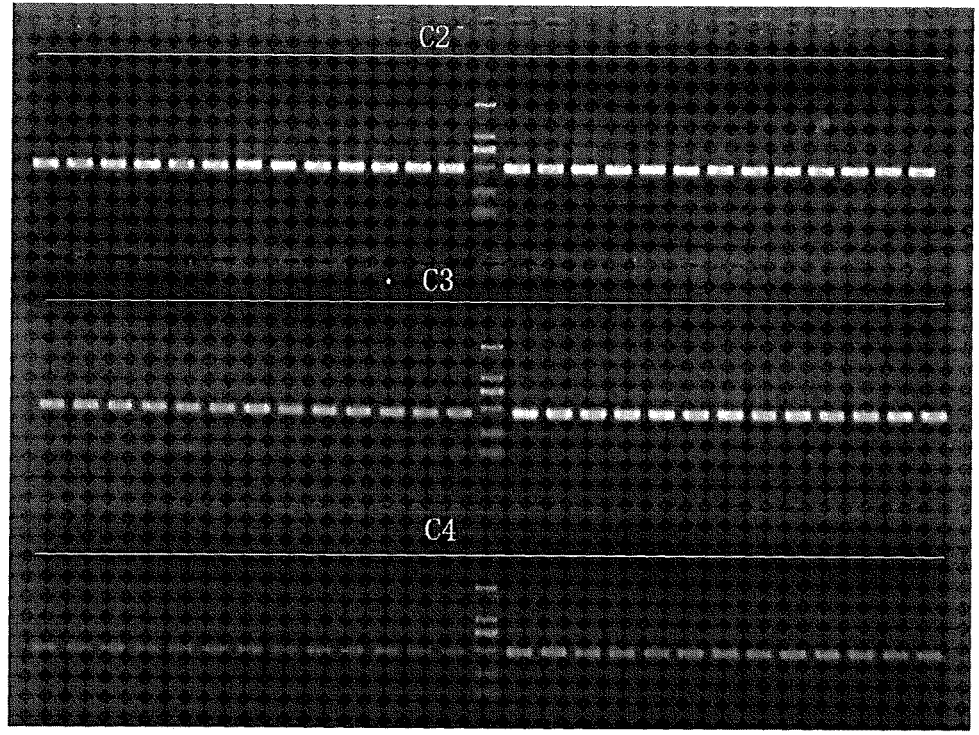
FIG. 9: A drawing illustrating electrophoresis results of PCR products of Exons 2, 3 and 4 of HLA-C site of 26 samples in Example 9. As shown in the figure, all the PCR products are of a length less than 500 bp; the electrophoretic band is single; there is no obvious non-specific band; and the amplification efficiency of the same pair of primers is the same in various samples.

PCR products were subjected to agarose gel electrophoresis (FIG. 9) before purification.

3. Purification of PCR Products

PCR products were purified by using Millipore purification plates. The main steps were as followed. The wells to be used were marked with a marker pen in the 96-well purification plate for PCR products, and 50 μl ultrapure water was added to each of the wells to be used. The rest wells were sealed by sealing film. The plate was stood for 15 min or was connected to a drawing and filtering system (−10 pa) for 5 min. When the purification plate was taken from the drawing and filtering system, liquid in the discharge port at the bottom of the purification plate was sipped up with absorbent paper.

PCR products to be purified were centrifugated at 4000 rpm for 1 min; the cover or silica gel pad for the PCR products to be purified was removed, and 100 μl ultrapure water was added to each PCR reaction system. Then, the purification plate, to which the PCR products to be purified were added, was connected to the drawing and filtering system, and the vacuum degree was adjusted to −10 pa as shown in barometer. The drawing and filtering were continued until no liquid was left on the microporous regeneratable cellulose film at the bottom of the purification plate, and no reflection gloss of intact liquid surface was found when observing under light.

In the wells containing PCR products to be purified, 50 μl ultrapure water or TE was added to the microporous regeneratable cellulose film; the purification plate was vibrated at room temperature in a trace vibrator for 5 min; and the whole liquids contained in the corresponding wells were transferred to the corresponding wells of a new 96-well PCR plate.

4. Performance of Sequencing Reaction and Purification of Products of the Sequencing Reaction The above purified PCR products were used as templates for sequencing reaction.

Conditions for Sequencing Reaction
96° 2 min
96° 10 s→55° 5 s→60° 2 min (25 cycles)
15° ∞

The System for Sequencing Reaction was

| | |
|---|---|
| Purified PCR products | 1 μL |
| primers (3.2 pmol/l) | 1 μL |
| 2.5 *Bigdye | 0.3 μL |
| 5*Buffer | 0.85 μL |
| water | 1.85 μL |
| Total volume | 5 μL |

The products of the sequencing reaction were purified by the following steps: the sequencing reaction plate was balanced, and centrifugated at 3000 g for 1 min. In the 96-well plate, to each 5 μl reaction system, 2 μL 0.125 mol/L EDTA-Na2 solution, 33 μL 85% ethanol were added, and the plate was covered by a silica gel pad and was sufficiently vibrated for 3 min. The plate was then centrifugated at 4°, 3000 g for 30 min. The sequencing plate was taken out after centrifugation, the silica gel pad was removed, and the sequencing plate was placed downwardly onto absorbent paper, and was then subjected to inverted centrifugation until the centrifugal force reached 185 g. To each well of the 96-well plate, 50 μl 70% ethanol was added. The plate was covered with a silica gel pad, and vibrated for 1.5 min, and centrifugated at 4°, 3000 g for 15 min. The sequencing reaction plate was then placed in a dark and ventilative place for 30 min so as to be air-dried until no ethanol odor was felt. To each well of the 96-well plate, 10 μL HI-DI formamide was added (alternatively, to each well of a 384-well plate, 8 μL was added), and then the plate was covered by sealing film, and was centrifugated to 1000 rpm after vibrating for 5 s.

5. Sequencing and Result Analysis

Figure 10:
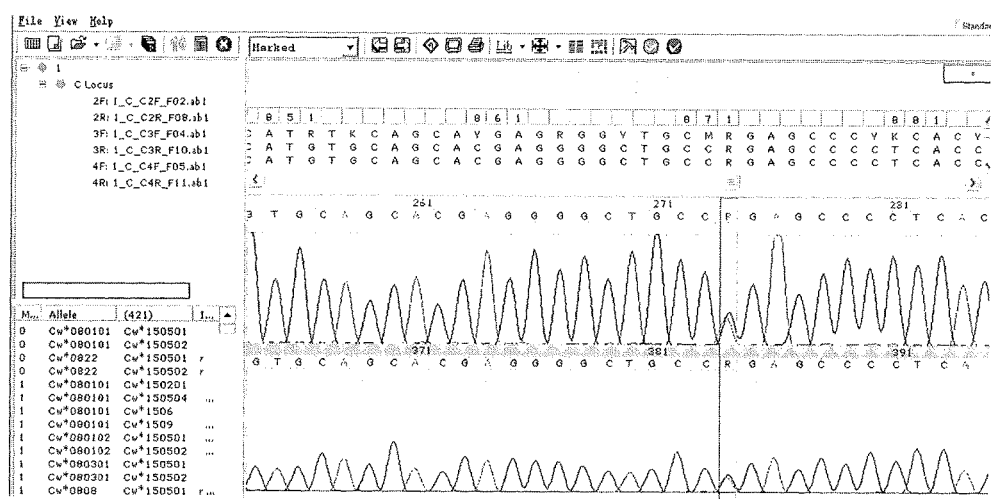
FIG. 10: A drawing illustrating the analytic results of the sequencing data of PCR amplification products of Template 1 by using uType software in Example 9. The result output column on the left shows the result, C*08:01:01 C*15:05:01, which are identical to the original known type of Template 1. The sequence depicted as "CATRTKCAGCAY-GAGRGGYTGCMR GAGCCCYKCACY" is SEQ ID NO: 251. The sequence depicted as "CATGTG CAGCAC-GAGGGGCTGCCRGAGCCCCTCACC" is SEQ ID NO: 252. The sequence depicted as "CATGTGCAGCAC-GAGGGGCTGCCRGAGCCCCTCACC" is SEQ ID NO: 253. The sequence depicted as "GTGCAGCAC- GAGGGGCTGCRGAGCCCCTCAG" is SEQ ID NO: 254. The sequence depicted as "GTGCAGCACGAGGGGCT-GCCRGAGCCCCTCA" is SEQ ID NO: 255.

Purified products of the sequencing reaction were subjected to capillary electrophoresis sequencing in ABI 3730XL. The sequencing peaks were analyzed by uType software (Invitrogen) to obtain HLA typing results (FIG. 10). All the results obtained by the above method were identical to the original known results, as shown in Table 10.

TABLE 10

Comparison of the typing results obtained by the above method with the original known typing results

| Sample No. | Original known HLA-C genotype | | Results for HLA-C obtained at this time | | Identical or not |
|---|---|---|---|---|---|
| 1 | C*08:01 | C*15:05 | C*08:01 | C*15:05 | yes |
| 2 | C*01:02 | C*07:02 | C*01:02 | C*07:02 | yes |
| 3 | C*08:01 | C*16:02 | C*08:01 | C*16:02 | yes |
| 4 | C*01:02 | C*03:02 | C*01:02 | C*03:02 | yes |
| 5 | C*01:02 | C*02:02 | C*01:02 | C*02:02 | yes |
| 6 | C*01:02 | C*15:02 | C*01:02 | C*15:02 | yes |
| 7 | C*01:02 | C*03:04 | C*01:02 | C*03:04 | yes |
| 8 | C*03:02 | C*07:02 | C*03:02 | C*07:02 | yes |
| 9 | C*06:02 | C*16:02 | C*06:02 | C*16:02 | yes |
| 10 | C*01:02 | C*03:04 | C*01:02 | C*03:04 | yes |
| 11 | C*03:04 | C*07:02 | C*03:04 | C*07:02 | yes |
| 12 | C*07:02 | C*08:01 | C*07:02 | C*08:01 | yes |
| 13 | C*01:02 | C*15:02 | C*01:02 | C*15:02 | yes |
| 14 | C*01:02 | C*03:04 | C*01:02 | C*03:04 | yes |
| 15 | C*01:02 | C*03:04 | C*01:02 | C*03:04 | yes |
| 16 | C*07:02 | C*12:02 | C*07:02 | C*12:02 | yes |
| 17 | C*04:01 | C*08:01 | C*04:01 | C*08:01 | yes |
| 18 | C*08:01 | C*16:02 | C*08:01 | C*16:02 | yes |
| 19 | C*14:02 | C*15:02 | C*14:02 | C*15:02 | yes |
| 20 | C*01:02 | C*03:03 | C*01:02 | C*03:03 | yes |
| 21 | C*03:03 | C*08:01 | C*03:03 | C*08:01 | yes |
| 22 | C*03:04 | C*07:02 | C*03:04 | C*07:02 | yes |
| 23 | C*07:02 | C*08:01 | C*07:02 | C*08:01 | yes |
| 24 | C*07:02 | C*12:02 | C*07:02 | C*12:02 | yes |
| 25 | C*07:02 | C*12:03 | C*07:02 | C*12:03 | yes |
| 26 | C*01:02 | C*07:02 | C*01:02 | C*07:02 | yes |

Example 10: HLA-DQB1 Genotyping by Using the Second Generation Sequencing Technique (Illumina Solexa)

94 blood samples with known HLA-SBT typing results were subjected to HLA-DQB1 genotyping, according to the methods as described in Example 8, except for the following items.

94 sets of PCR index primers were used to amplify 94 DNA samples, respectively, wherein each set of PCR index primers consisted of PCR primers for amplification of Exon 2 or 3 of HLA-DQB1 (Table 5) and a pair of bidirectional primer indexes (as described above), each forward PCR primer has the forward primer index of a pair of primer indexes linked at the 5' end, and the reverse PCR primer has the reverse primer index of a pair of primer indexes linked at the 5' end. During the synthesis of primers, the primer indexes were directly added to the 5' end of the PCR primers, wherein the primers were synthesized by Shanghai Invitrogen Co.

The 94 DNAs obtained in the sample extraction step, were designated as No. 1-94. PCR reaction was carried out in 96-well plates, Exons 2, 3 of DQB1 in each sample was amplified in the same well. Two negative controls without adding any template were set in each plate, and the primer indexes used in negative controls are PI-95 and PI-96. During experimentation, the numbering information of the sample corresponding to each pair of primer indexes was recorded.

The primer indexes used were the primer indexes PI-1 to PI-94 as listed in Table 6, and the following primer indexes PI-95 and PI-96 (Table 11) for negative controls.

TABLE 11

Relevant information on the primer indexes used for negative controls

| PI-95 | CGACGTAGAGTC (SEQ ID NO: 229) | CAGTAGCACTAC (SEQ ID NO: 230) | H11 Negative control |
|---|---|---|---|
| PI-96 | CACTGTATAGCT (SEQ ID NO: 239) | CGACTAGTACTA (SEQ ID NO: 240) | H12 Negative control |

PCR procedure for HLA-DQB1 was as followed:
96° 2 min
95° 30 s→60° 30 s→72° 20 s (32 cycles)
15° ∞
PCR reaction system for HLA-DQB1 was as followed:

| | |
|---|---|
| Promega 5x buffer I (Mg2+ plus) | 5.0 ul |
| dNTP mixture (2.5 mM each) | 2.0 ul |
| PInf-Q-F2 (2 pmol/ul) | 1.0 ul |
| PInf-Q-R2 (2 pmol/ul) | 1.0 ul |
| PInf-Q-F3 (2 pmol/ul) | 1.0 ul |
| PInf-Q-R3 (2 pmol/ul) | 1.0 ul |
| Promega Taq (5U/ul) | 0.2 ul |
| DNA (about 20 ng/ul) | 5.0 ul |
| ddH$_2$O | 8.8 ul |
| Total | 25.0 ul |

Wherein, PInf-Q-F2/3 represents the F primer of HLA-DQB1 having the forward primer index sequence No. n (Table 1) at 5' end; PInf-Q-R 2/3 represents the R primer of HLA-DQB1 having the reverse primer index sequence No. n at 5' end (here n≤96); and the rest may be deduced similarly. Moreover, each sample corresponds to a specific set of PCR primers.

Figure 11:
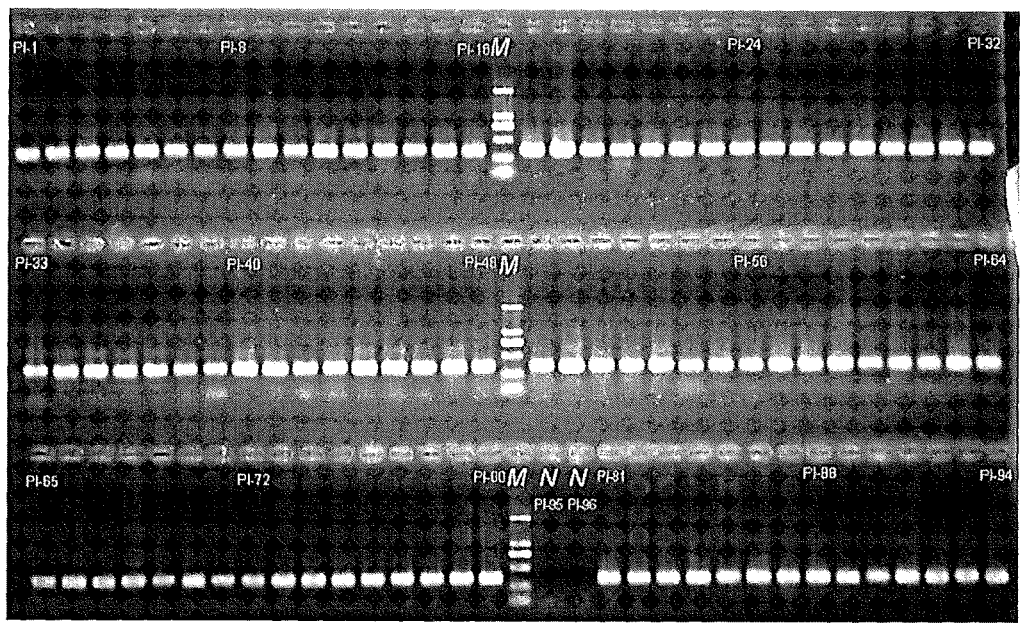
FIG. 11: A drawing illustrating the electrophoretic result of PCR products of Exon 2+3 of HLA-DQB1 in 94 samples of Example 10. It can be seen from electrophoretogram that PCR products are a series of single bands of 250 bp-500 bp, wherein Lane M is reference for standard DNA molecular weights (DL 2000, Takara Co.), Lanes PI-1 to PI-94 are the PCR amplification products of Exon 2+3 of HLA-DQB1 in 94 samples, and there is no amplification band in negative control (N).

PCR reaction was carried out in PTC-200 PCR apparatus from Bio-Rad Co. After PCR reaction, 2 ul PCR products were subjected to 1.5% agarose gel electrophoresis. FIG. 11 showed the electrophoretic result of the PCR products of Exons 2+3 of HLA-DQB1 of 94 samples, and the DNA molecular marker was DL 2000 (Takara Co.).

Pooling and Purification of PCR Products

20 μl of the rest PCR products was taken from each well of the 96-well plate HLA-P-DQB1 (except for the negative control), and was mixed homogeneously in a 3 ml EP tube (designated as HLA-Q-Mix). 500 ul DNA mixture from HLA-Q-Mix was subjected to column purification with Qiagen DNA Purification kit (QIAGEN Co.) (For the specific purification steps, please refer to the manufacturer's instruction). It was determined by Nanodrop 8000 (Thermo Fisher Scientific Co.) that the 200 ul DNA obtained by purification has a HLA-Q-Mix DNA concentration of 48 ng/ul.

Conditions for Shearing were as Followed:
Frequency Sweeping

| | |
|---|---|
| Duty Cycle | 10% |
| Intensity | 5 |
| Cycles/Burst | 200 |
| Time (s) | 300 |

The reaction products were subjected to terminal repairing reaction, and then were recovered and purified by QIAquick PCR Purification Kit, and were dissolved in 34 ul EB (QIAGEN Elution Buffer).

The reaction products were further subjected to the addition of A at 3' end, and then were recovered and purified by MiniElute PCR Purification Kit (QIAGEN Co.), and were dissolved in 13 μl EB solution (QIAGEN Elution Buffer).

After ligation of library adapters, the reaction products were purified by Ampure Beads (Beckman Coulter Genomics), and were dissolved in 50 μl deionized water, and the DNA concentration determined by Fluorescence quantitative PCR (QPCR) was as followed:

| | result determined by qPCR (nM) |
|---|---|
| HLA-Q-Mix | 115.3 |

Figure 12:
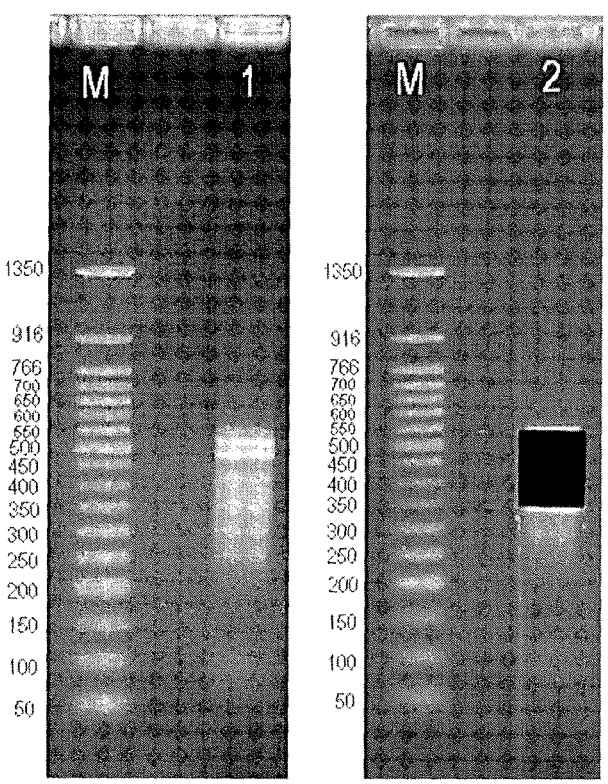
FIG. 12 shows the results of DNA electrophoretic gel slicing after shearing HLA-Q-Mix in Example 10, wherein the gel-slicing area is an area of 350-550 bp. Lane M is a marker of standard DNA molecular weights (NEB-50 bp DNA Ladder), and Lane 1 is a drawing showing the gel of HLA-Q-Mix before slicing, and Lane 2 is a drawing showing the gel of HLA-Q-Mix after slicing.

The gel containing the DNA fragments ranging from 350 to 550 bp was sliced (FIG. 12). After purification and recovery of the products from the gel, the DNA concentration, as determined by Fluorescence quantitative PCR (QPCR), was 18.83 nM.

Analysis of the Results

Figure 13:
FIG. 13 shows a screen-capture of the program for construction of consensus sequence of Sample No. 7 in Example 10, illustrating the main procedure of data analysis. Firstly, the sequence reads of the DQB1 site of the sample are aligned with the reference sequence by BWA software, thereby constructing the consensus sequences of Exons 2, 3 of DQB 1 of the sample; and haplotype sequences of Exons 2, 3 of DQB 1 are determined based on the linkage relationship between SNPs. As shown in the figure, six heterozygous SNPs are comprised in 2322-2412 area of DQB1 gene sequence of Sample No. 7, and it can be determined from read 1 that the linkage relationship of SNP1-SNP5 is T-G-T-C-C; it can be determined from read2 that the linkage relationship of another SNP1-SNP5 is C-C-A-G-T; it can be determined from read3 that the linkage relationship of SNP3-SNP6 is A-G-T-G; it can be determined from read4 that the linkage relationship of another SNP3-SNP6 is T-C-C-A; and it can be determined from the above linkage relationships of said SNPs that read 1 is linked to read4, read2 is linked to read3, the complete SNP combination in this area is T-G-T-C-C-A and C-C-A-G-T-G, and the sequences correspond to the shaded parts of the sequences of DQB1*0303 and DQB1*0602 type. The judgment of the linkage relationship of other areas is similar. The sequence labeled "reference consensus" is SEQ ID NO: 256. The sequence labeled as "DQB1*03:03" is SEQ ID NO: 257. The sequence labeled as "DQB1*06:02" is SEQ ID NO: 258.
Figure 14:
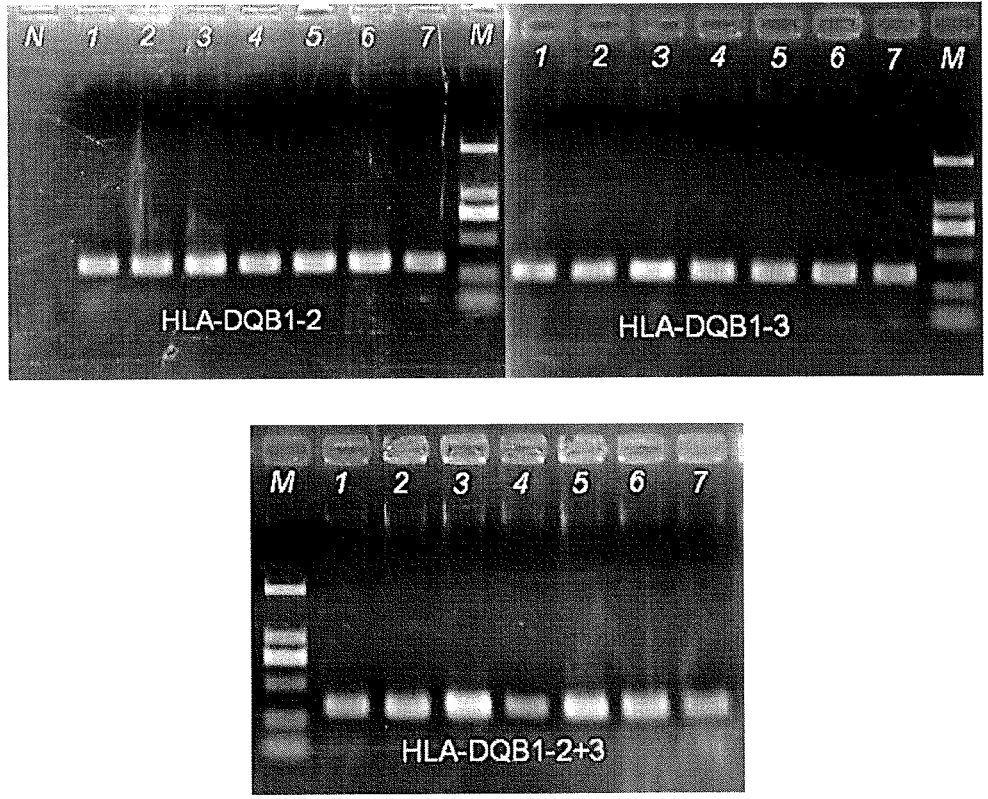
FIG. 14 shows the electrophoretogram of the products in Example 11, resulted from amplification of each of Exons 2 and 3 of HLA-DQB1 site and amplification of Exons 2 and 3 with two pairs of PCR primers, respectively. The electrophoretogram shows three sets of PCR products from seven DNA templates, wherein all the PCR products have a length less than 500 bp; electrophoretic bands are single; and there is no obvious non-specific band. There is no amplification band in negative control (N), and Lane M is reference for standard DNA molecular weights (DL 2000, Takara Co.).

The sequencing results from Illumina GA were a series of DNA sequences, and by searching the forward and reverse primer index sequences and primer sequences in the sequencing results, databases, comprising the sequencing results of the PCR products of various exons of HLA-DQB 1 for each sample corresponding to respective primer index were constructed. The sequencing results of each exon was aligned to the reference sequence of the corresponding exon by BWA (Burrows-Wheeler Aligner), and consensus sequences of each database were constructed, and the sequence reads were selected and corrected based on the quality value of base sequencing, and difference between the sequence reads and consensus sequences. The corrected DNA sequences were assembled into the corresponding sequences of Exons 2, 3 of HLA-DQB 1 on the basis of sequence overlapping and linkage (Paired-End linkage) relationship. The screen-capture of FIG. 13 illustrates the procedure for construction of consensus sequence of Exon 2 of HLA-DQB I site in Sample No. 7.

The resultant DNA sequence for Exons 2, 3 of HLA-DQB1 was aligned with the sequence database of the corresponding exon of HLA-DQB1 in IMGT HLA professional database. If the result of sequence alignment showed 100% match, the HLA-DQB1 genotype of the corresponding sample was determined.

For all 94 samples, the typing results obtained by the above method were completely consistent with the original known typing results, wherein the results of Samples No. 1-32 were shown in Table 12.

TABLE 12

The typing results of Samples No. 1-32

| Sample No. | Original known DQB1 genotype | | Results for DQB1 obtained at this time | | Identical or not |
|---|---|---|---|---|---|
| 1 | DQB1*02:02 | DQB1*03:01 | DQB1*02:02 | DQB1*03:01 | yes |
| 2 | DQB1*02:02 | DQB1*04:01 | DQB1*02:02 | DQB1*04:01 | yes |
| 3 | DQB1*05:02 | DQB1*02:02 | DQB1*05:02 | DQB1*02:02 | yes |
| 4 | DQB1*02:02 | DQB1*06:03 | DQB1*02:02 | DQB1*06:03 | yes |
| 5 | DQB1*03:03 | DQB1*04:02 | DQB1*03:03 | DQB1*04:02 | yes |
| 6 | DQB1*05:02 | DQB1*03:17 | DQB1*05:02 | DQB1*03:17 | yes |
| 7 | DQB1*03:03 | DQB1*06:02 | DQB1*03:03 | DQB1*06:02 | yes |
| 8 | DQB1*05:03 | DQB1*04:02 | DQB1*05:03 | DQB1*04:02 | yes |
| 9 | DQB1*04:02 | DQB1*06:01 | DQB1*04:02 | DQB1*06:01 | yes |
| 10 | DQB1*05:01 | DQB1*06:10 | DQB1*05:01 | DQB1*06:10 | yes |
| 11 | DQB1*03:01 | DQB1*03:03 | DQB1*03:01 | DQB1*03:03 | yes |
| 12 | DQB1*05:01 | DQB1*05:01 | DQB1*05:01 | DQB1*05:01 | yes |
| 13 | DQB1*02:02 | DQB1*04:02 | DQB1*02:02 | DQB1*04:02 | yes |

TABLE 12-continued

The typing results of Samples No. 1-32

| Sample No. | Original known DQB1 genotype | Results for DQB1 obtained at this time | Identical or not |
|---|---|---|---|
| 14 | DQB1*05:02 DQB1*02:01 | DQB1*05:02 DQB1*02:01 | yes |
| 15 | DQB1*02:01 DQB1*06:02 | DQB1*02:01 DQB1*06:02 | yes |
| 16 | DQB1*03:03 DQB1*04:01 | DQB1*03:03 DQB1*04:01 | yes |
| 17 | DQB1*05:01 DQB1*03:02 | DQB1*05:01 DQB1*03:02 | yes |
| 18 | DQB1*03:03 DQB1*06:01 | DQB1*03:03 DQB1*06:01 | yes |
| 19 | DQB1*03:03 DQB1*06:10 | DQB1*03:03 DQB1*06:10 | yes |
| 20 | DQB1*05:03 DQB1*04:01 | DQB1*05:03 DQB1*04:01 | yes |
| 21 | DQB1*05:02 DQB1*04:01 | DQB1*05:02 DQB1*04:01 | yes |
| 22 | DQB1*03:01 DQB1*03:03 | DQB1*03:01 DQB1*03:03 | yes |
| 23 | DQB1*05:02 DQB1*05:03 | DQB1*05:02 DQB1*05:03 | yes |
| 24 | DQB1*05:02 DQB1*03:02 | DQB1*05:02 DQB1*03:02 | yes |
| 25 | DQB1*03:03 DQB1*06:01 | DQB1*03:03 DQB1*06:01 | yes |
| 26 | DQB1*05:02 DQB1*06:09 | DQB1*05:02 DQB1*06:09 | yes |
| 27 | DQB1*02:02 DQB1*06:02 | DQB1*02:02 DQB1*06:02 | yes |
| 28 | DQB1*05:02 DQB1*03:01 | DQB1*05:02 DQB1*03:01 | yes |
| 29 | DQB1*02:01 DQB1*03:01 | DQB1*02:01 DQB1*03:01 | yes |
| 30 | DQB1*06:03 DQB1*06:09 | DQB1*06:03 DQB1*06:09 | yes |
| 31 | DQB1*05:02 DQB1*02:02 | DQB1*05:02 DQB1*02:02 | yes |
| 32 | DQB1*05:01 DQB1*06:01 | DQB1*05:01 DQB1*06:01 | yes |

Example 11: HLA-DQB1 Genotyping by Using Sanger Sequencing Method

1. Sample DNA Extraction

As described in Example 1, DNAs were extracted by using KingFisher Automatic Extraction Instrument from 20 out of 94 samples with known HLA genotypes.

2. PCR Amplification

The above DNAs, extracted by using KingFisher Automatic Extraction Instrument, were used as templates, and PCR amplification was carried out in single tubes by using two pairs of PCR primers (Q-F2 and Q-R2, Q-F3 and Q-R3) as listed in Table 5, respectively. The PCR procedure for each pair of primers was as followed:

96° 2 min
95° 30 s→56° 30 s→72° 20 s (35 cycles)
15° ∞

PCR Reaction System for HLA-Q was as Followed:

| Promega 5x buffer I (Mg2+ plus) | 5.0 μL |
|---|---|
| dNTP Mixture (2.5 mM each) | 2.0 μL |
| Primer mixture (25 ng/μL) | 3.0 μL |
| Promega Taq (5 U/μL) | 0.2 μL |
| DNA (about 20 ng/μL) | 2.0 μL |
| ddH2O | 12.8 μL |
| total | 25.0 μL |

PCR products were subjected to agarose gel electrophoresis before purification.

3. Purification of PCR Products

The method and steps were the same as those described in Example 9.

4. Performance of Sequencing Reaction and Purification of Products of the Sequencing Reaction The method and steps were the same as those described in Example 9.

5. Sequencing and Result Analysis

Figure 15:
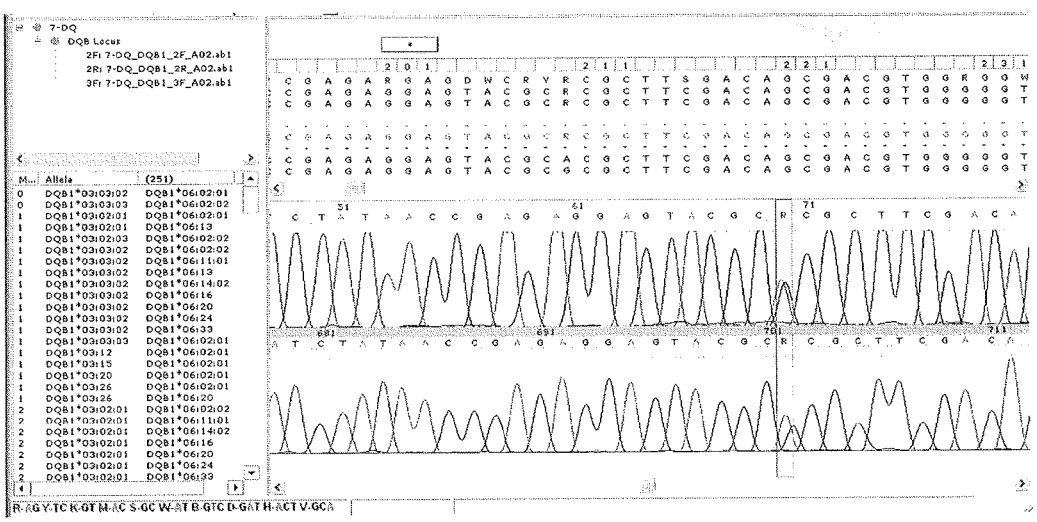
FIG. 15 illustrates the analytic results of the sequencing data of PCR products resulted from amplification of Exons 2 and 3 of HLA-DQB 1 of Template 7, by using uType software in Example 11. The result output column on the left shows the result, DQB 1*03:03 DQB 1*06:02, which is identical to the original known result of Template 7. The sequence depicted as "CGAGARGAGDWCRYRCGCTTS-GACAGCGACGTGGRGGW" is SEQ ID NO: 259. The sequence depicted as "CGAGAGGAGTACGCRCGCTTC-GACAGCGACGTGGGGGT" is SEQ ID NO: 260. The sequence depicted as "CGAGAGGAGTACGCRCGCTTC-GACAGC GACGTGGGGGT" is SEQ ID NO: 261. The sequence depicted as "CGAGAGGAGTAC GCRCGCTTC-GACAGCGACGTGGGGGT" is SEQ ID NO: 262. The sequence depicted as "CGAGAGGAGTACGCACGCTTC-GACAGCGACGTGGGGGT" is SEQ ID NO: 263.

Purified products of the sequencing reaction were subjected to capillary electrophoresis sequencing in ABI 3730XL. The sequencing peaks were analyzed by uType software (Invitrogen) to obtain HLA typing results (FIG. 15). All the results obtained by the above method were identical to the original known results, as shown in Table 13.

TABLE 13

Comparison of the typing results obtained by the above method with the original known typing results

| Sample No. | Original known DQB1 genotype | Results for DQB1 obtained at this time | Identical or not |
|---|---|---|---|
| 1 | DQB1*02:02 DQB1*03:01 | DQB1*02:02 DQB1*03:01 | yes |
| 2 | DQB1*02:02 DQB1*04:01 | DQB1*02:02 DQB1*04:01 | yes |
| 3 | DQB1*05:02 DQB1*02:02 | DQB1*05:02 DQB1*02:02 | yes |
| 4 | DQB1*02:02 DQB1*06:03 | DQB1*02:02 DQB1*06:03 | yes |
| 5 | DQB1*03:03 DQB1*04:02 | DQB1*03:03 DQB1*04:02 | yes |
| 6 | DQB1*05:02 DQB1*03:17 | DQB1*05:02 DQB1*03:17 | yes |
| 7 | DQB1*03:03 DQB1*06:02 | DQB1*03:03 DQB1*06:02 | yes |
| 8 | DQB1*05:03 DQB1*04:02 | DQB1*05:03 DQB1*04:02 | yes |
| 9 | DQB1*04:02 DQB1*06:01 | DQB1*04:02 DQB1*06:01 | yes |
| 10 | DQB1*05:01 DQB1*06:10 | DQB1*05:01 DQB1*06:10 | yes |
| 11 | DQB1*03:01 DQB1*03:03 | DQB1*03:01 DQB1*03:03 | yes |
| 12 | DQB1*05:01 DQB1*05:01 | DQB1*05:01 DQB1*05:01 | yes |
| 13 | DQB1*02:02 DQB1*04:02 | DQB1*02:02 DQB1*04:02 | yes |
| 14 | DQB1*05:02 DQB1*02:01 | DQB1*05:02 DQB1*02:01 | yes |
| 15 | DQB1*02:01 DQB1*06:02 | DQB1*02:01 DQB1*06:02 | yes |
| 16 | DQB1*03:03 DQB1*04:01 | DQB1*03;03 DQB1*04:01 | yes |
| 17 | DQB1*05:01 DQB1*03:02 | DQB1*05:01 DQB1*03:02 | yes |
| 18 | DQB1*03:03 DQB1*06:01 | DQB1*03:03 DQB1*06:01 | yes |
| 19 | DQB1*03:03 DQB1*06:10 | DQB1*03:03 DQB1*06:10 | yes |
| 20 | DQB1*05:03 DQB1*04:01 | DQB1*05:03 DQB1*04:01 | yes |

Example 12: Genotyping of Exons 2, 3, 4 of HLA-A/B/C and Exons 2, 3 of HLA-DQB1 in 950 Samples In the present example, Exons 2, 3, 4 of HLA-A/B/C and Exons 2, 3 of HLA-DQB1 in 950 samples were genotyped by using the combination of primer indexes, DNA incomplete shearing strategy, library indexes, PCR-Free libraries preparation, and Illumia GA Paired-End 100 sequencing technique (PCR products having a length ranging from 300 bp to 500 bp), demonstrating that the method of the present invention could accomplish the genotyping of gene fragments of a length exceeding the maximum read length of sequencer, and also demonstrating that the present invention could accomplish HLA genotyping with low cost, high throughput, high accuracy and high resolution.

Principle: the samples to be analyzed were divided into 10 groups; for samples of each group, primer indexes were introduced to the two termini of the PCR products of Exons 2, 3, 4 of HLA-A/B/C and Exons 2, 3 of HLA-DQB1 by PCR reaction so as to specifically label the sample information of the PCR products. The products of PCR amplification of four sites (HLA-A/B/C/DQB1) in each group of samples were mixed together to obtain a library of PCR products; after incomplete ultrasonic shearing of the libraries of PCR products, indexed PCR-free sequencing libraries were constructed (wherein for the PCR product library of each sample group, a different adapter was used, thereby constructing 10 indexed sequencing libraries). The 10 indexed sequencing libraries were pooled together at an equal mole to construct a mixed index sequencing library. The mixed index sequencing library was subjected to 2% low melting point agarose gel electrophoresis, and all the DNA bands of a length ranging from 450 bp to 750 bp were recovered and purified by gel slicing. The recovered DNA was sequenced by the Illumina GA PE-100 method. The sequence information of all the tested samples can be traced by primer index sequences and library index sequences, and the sequence of the whole PCR product can be assembled on the basis of the known reference sequences and the overlapping and linkage relationship between the sequences of DNA fragments, The complete sequence of the original PCR product can be aligned with the standard database of the corresponding exons of HLA-A/B/C/DQB1, thereby accomplishing HLA-A/B/C/DQB1 genotyping.

1. Sample Extraction

DNAs were extracted from 950 blood samples with known HLA-SBT typing results (China Marrow Donor Program cited hereafter as (CMDP)) by using KingFisher Automatic Extraction Instrument (US Thermo Co.). The process was the same as that described in Example 1.

2. PCR Amplification

The 950 DNAs obtained from the sample extraction step were designated as No. 1-950, and were divided into 10 groups (95 DNAs for each group), which were designated as HLA-1, HLA-2, HLA-3, HLA-4, HLA-5, HLA-6, HLA-7, HLA-8, HLA-9, HLA-10. For each group of samples, 95 DNA samples were amplified by 95 sets of PCR primers carrying bidirectional primer indexes (Table 6) for amplification of Exons 2, 3, 4 of HLA-A/B (Table 2), for amplification of Exons 2, 3, 4 of HLA-C (Table 4), and for amplification of Exons 2, 3 of HLA-DQB1 (Table 5), respectively. PCR reaction took place in 96-well plates, using 100 plates in total, designated as HLA-X-P-A2, HLA-X-P-A3, HLA-X-P-A4, HLA-X-P-B2, HLA-X-P-B3, HLA-X-P-B4, HLA-X-P-C2, HLA-X-P-C3, HLA-X-P-C4 and HLA-X-P-DQB1 ("X" represents the information of the group number 1/2/3/4/5/6/7/8/9/10, "A2/3/4", "B2/3/4", "C2/3/4", "DQB1" represent the amplification sites), wherein a negative control without adding any template was set in each plate, and the primers used for the negative control were primers labeled by PI-1 (Table 6). During experimentation, the information of each sample on the group number and primer indexes was recorded. For example, the relevant information on primer indexes PI-1 and PI-2 was as followed, and the rest may be deduced similarly.

described in Example 10, and the PCR primers for amplification of the corresponding exons of HLA-DQB1 were as shown in Table 5.

Wherein, $PI_{nf}$-A/B/C-$F_{2/3/4}$ and $PI_{nf}$-Q-F2/F3 represent the F primers of HLA-A/B/C/DQB1 having the forward primer index sequence No. n (Table 6) at 5' end, $PI_{nr}$-A/B/C-$R_{2/3/4}$ and $PI_{nr}$-Q-R2/R3 represent the R primers of HLA-A/B/C/DQB1 having the reverse primer index sequence No. n at 5' end (here n≤95), and the rest may be deduced similarly. Moreover, each sample corresponds to a specific set of PCR primers ($PI_{nf}$-A/B/C-$F_{2/3/4}$, $PI_{nr}$-A/B/C-$R_{2/3/4}$, $PI_{nr}$-Q-R2/R3).

Figure 16:
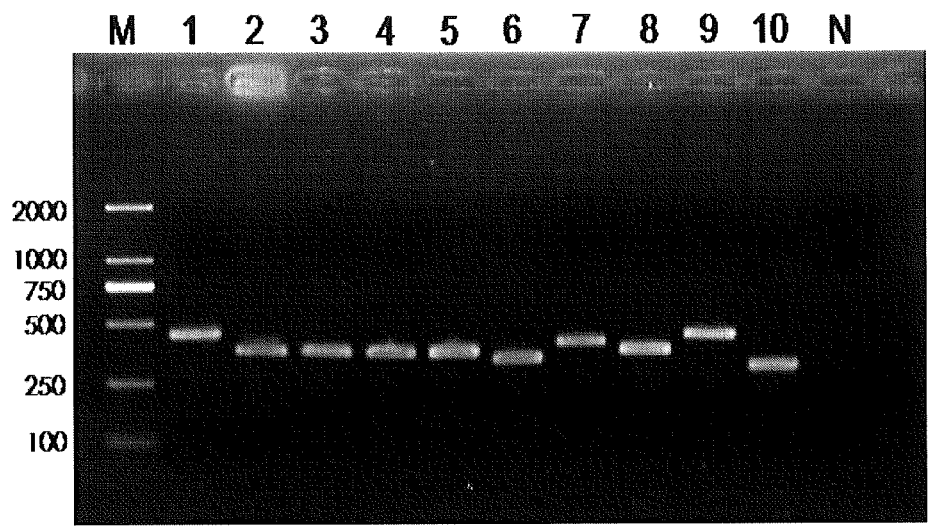

PCR reaction was carried out in PTC-200 PCR apparatus from Bio-Rad Co. After PCR reaction, 3 ul PCR products were subjected to 2% agarose gel electrophoresis. FIG. 16 showed the electrophoretic result of the PCR products of the corresponding exons of HLA-A/B/C/DQB1 of Sample No. 1, and the DNA molecular marker was DL 2000 (Takara Co.). There were a series of single bands of a length ranging from 300 bp to 500 bp in the electrophorogram, indicating successful PCR amplification of exons (A2, A3, A4, B2, B3, B4, C2, C3, C4, DRB1) of HLA-A/B/C/DQB1 of Sample No. 1. There was no amplification band in negative control (N). The results of other samples were similar.

3. Pooling and Purification of PCR Products

For samples of Group X ("X" is 1/2/3/4/5/6/7/8/9/10), 20 µl of the rest PCR products was taken from each well of the 96-well plate HLA-X-P-A2 (except for the negative control), and was mixed homogeneously under shaking in a 3 ml EP tube (designated as HLA-X-A2-Mix). The same operation was applied to the other 9 96-well plates of the samples of Group X, designated as HLA-X-A3-Mix, HLA-X-A4-Mix, HLA-X-B2-Mix, HLA-X-B3-Mix, HLA-X-B4-Mix, HLA-X-C2-Mix, HLA-X-C3-Mix, HLA-X-C4-Mix, and HLA-X-DQB1-Mix. 200 ul was taken from each of HLA-X-A2-Mix, HLA-X-A3-Mix, HLA-X-A4-Mix, HLA-X-B2-

| primer index No. | forward primer index | reverse primer index | Corresponding position in 96-well plate | Corresponding template (Group 1) | Corresponding template (Group n + 1, wherein 1 ≤ n < 10, n was an integer) |
|---|---|---|---|---|---|
| PI-1 | TCGCAGACATCA | TGACACGATGCT | A1 | 1 | 1 + 95*n |
| PI-2 | TACATCGCACTA | TACAGATGCTGA | A2 | 2 | 2 + 95*n |

The PCR procedure and PCR reaction system for HLA-A/B/C were the same as those described in Example 2. The PCR primers for amplification of the corresponding exons of HLA-A/B were shown in Table 2, and the PCR primers for amplification of the corresponding exons of HLA-C were shown in Table 4.

PCR procedure for HLA-DQB1 was as followed.

96° 2 min

95° 30 s→55° 30 s→72° 20 s (32 cycles)

15° ∞

Multiple PCR reaction system for HLA-DQB1 (amplification of Exons 2, 3 simultaneously) is the same as the one Mix, HLA-X-B3-Mix, HLA-X-B4-Mix, HLA-X-C2-Mix, HLA-X-C3-Mix, HLA-X-C4-Mix, and HLA-X-DQB1-Mix, and was mixed in a 3 ml EP tube, designated as HLA-X-Mix. 500 ul DNA mixture from HLA-X-Mix was subjected to column purification with Qiagen DNA Purification kit (QIAGEN Co.) (For the specific purification steps, please refer to the manufacturer's instruction) to obtain 200 ul purified DNA, of which the DNA concentration were determined by Nanodrop 8000 (Thermo Fisher Scientific Co.). The same operation was also applied to the other 9 groups of samples. The finally determined DNA concentrations of the 10 groups of samples were as followed.

|  | HLA-1-Mix | HLA-2-Mix | HLA-3-Mix | HLA-4-Mix | HLA-5-Mix | HLA-6-Mix | HLA-7-Mix | HLA-8-Mix | HLA-9-Mix | HLA-10-Mix |
|---|---|---|---|---|---|---|---|---|---|---|
| Conc. (ng/ul) | 53.1 | 52.3 | 56.1 | 57.2 | 50.5 | 55.7 | 54.2 | 58.6 | 53.9 | 54.8 |

4. Construction of Illumina GA Sequencing Libraries

As described in Example 4, a total amount of 5 ug DNA, taken from the purified HLA-X-Mix, was subjected to DNA shearing, purification after shearing, terminal repairing reaction, addition of A at 3' end, and ligation of Illumina GA PCR-Free library adapter.

The corresponding relationship between the sample groups and library adapters was as followed.

| | Sample group No. | | | | | | | | | |
|---|---|---|---|---|---|---|---|---|---|---|
| | HLA-1 | HLA-2 | HLA-3 | HLA-4 | HLA-5 | HLA-6 | HLA-7 | HLA-8 | HLA-9 | HLA-10 |
| Library adapter No. | 1 | 2 | 3 | 4 | 5 | 6 | 7 | 8 | 9 | 10 |

The obtained reaction products were purified by Ampure Beads (Beckman Coulter Genomics), and were dissolved in 50 ul deionized water, and the DNA concentrations determined by Fluorescence quantitative PCR (QPCR) were as followed:

|  | HLA-1-Mix | HLA-2-Mix | HLA-3-Mix | HLA-4-Mix | HLA-5-Mix | HLA-6-Mix | HLA-7-Mix | HLA-8-Mix | HLA-9-Mix | HLA-10-Mix |
|---|---|---|---|---|---|---|---|---|---|---|
| Conc./nM | 86.60 | 78.21 | 54.56 | 87.35 | 84.37 | 85.09 | 96.21 | 85.81 | 88.14 | 88.26 |

6. Recovery by Gel Slicing

Figure 17:
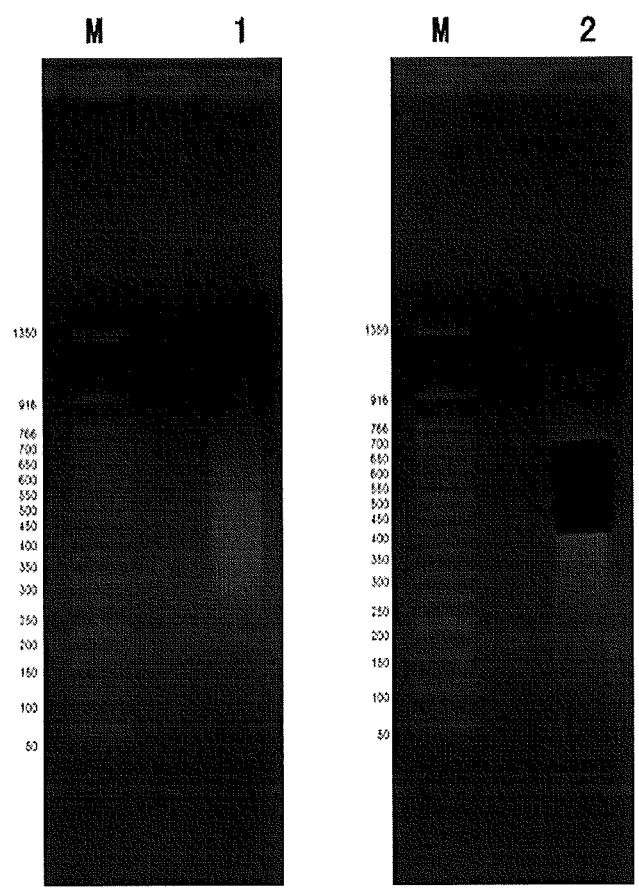
FIG. 17 illustrates the result of recovery from agarose gel after pooling HLA-1-Mix, HLA-2-Mix, HLA-3-Mix, HLA-4-Mix, HLA-5-Mix, HLA-6-Mix, HLA-7-Mix, HLA-8-Mix, HLA-9-Mix and HLA-10-Mix in equal mole in Example 12. Lane M is a marker of molecular weights, and Lane 1 is the electrophoretic result of the pool, and Lane 2 is the electrophoretogram after gel slicing containing the DNA fragments of a length ranging from 450 to 750 bp.

HLA-1-Mix, HLA-2-Mix, HLA-3-Mix, HLA-4-Mix, HLA-5-Mix, HLA-6-Mix, HLA-7-Mix, HLA-8-Mix, HLA-9-Mix and HLA-10-Mix were mixed at an equal mole (final concentration was 70.86 nM/ul), designated as HLA-Mix-10. 30 μL HLA-Mix-10 was subjected to 2% low melting point agarose gel electrophoresis. The electrophoretic condition was 100V, 100 min, DNA marker was the 50 bp DNA marker from NEB Co. The gel containing the DNA fragments ranging from 450 to 750 bp was sliced (FIG. 17). The products in the sliced gel were recovered and purified by QIAquick PCR Purification Kit (QIAGEN Co.), the volume after purification was 32 ul, the DNA concentration measured by Fluorescence quantitative PCR (QPCR) was 10.25 nM.

5. Illumina GA Sequencing and Result Analysis

Sequencing and result analysis were carried out according to the methods as described in Examples 5 and 6.

Figure 18:
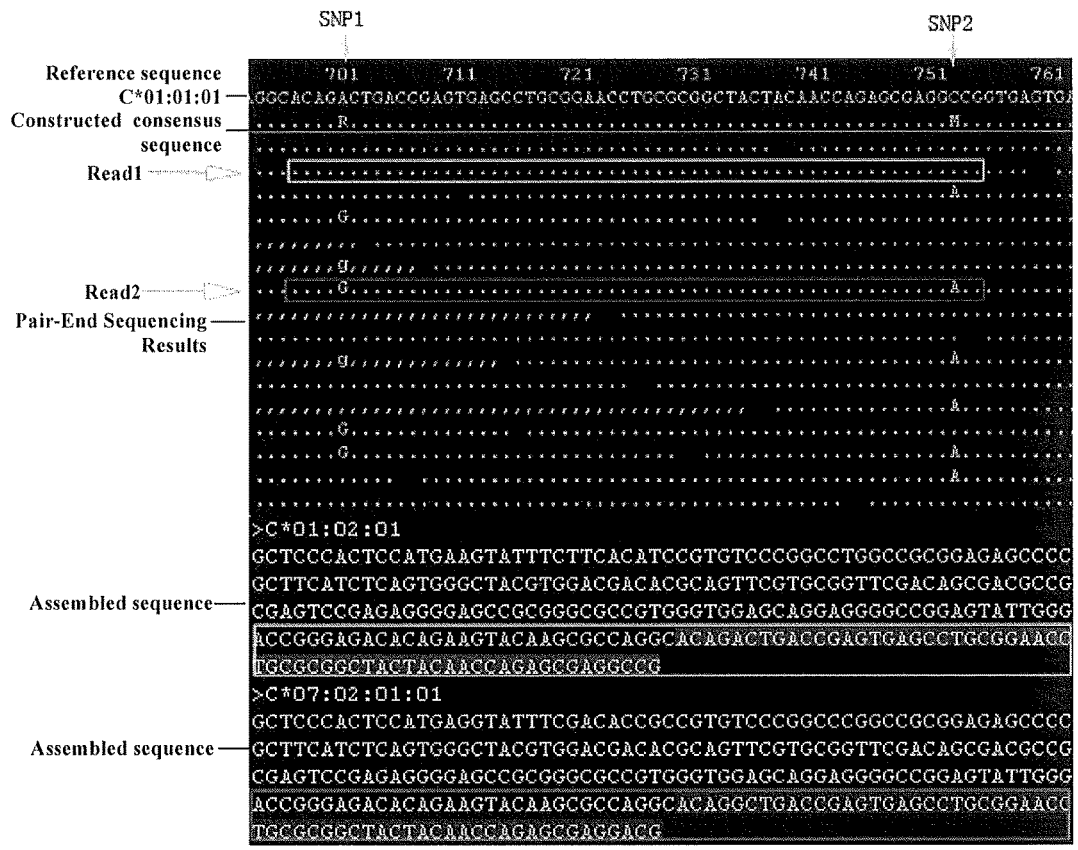
FIG. 18 shows a screen-capture of the program for construction of consensus sequence of Exon 2 of HLA-C site of Sample No. I in Example 12. Firstly, the sequence reads of C site of the sample are aligned with the reference sequence by BWA software, thereby constructing the consensus sequences of Exons 2, 3, 4 of C site of the sample; further, the haplotype sequences of the exons of C site are determined on the basis of the linkage relationship between SNPs; and finally the type of the sample is determined by the intersection of the haplotype sequences of the exons. As shown in the figure, two heterozygous SNPs are comprised in 695-764 area of C gene sequence of Sample No. 1, and it can be determined from read1 and read2 that the linkage relationship of SNPs is A-C, G-A (" . . . " in the figure represents the bases identical to those of the reference sequence). The sequences correspond to the shaded parts of the sequences of the C*010201 and C*07020101 type, respectively. The judgment of linkage relationship of other areas is similar. The Reference sequence C*01:01:01 is SEQ ID NO: 267. The upper Assembled Sequence C*01:02:01 is SEQ ID NO: 268. The lower Assembled Sequence C*07:02:01:01 is SEQ ID NO: 269.

Databases, comprising the sequencing results of the PCR products of various exons of HLA-A/B/C/DQB1 for each sample corresponding to respective primer index were constructed. The resultant DNA sequence was aligned with the sequence database of the corresponding exon of HLA-A/B/C/DQB1 in IMGT HLA professional database. If the result of sequence alignment showed 100% match, the HLA-A/B/C/DQB1 genotype of the corresponding sample was determined. Please refer to the screen-capture of the program for construction of consensus sequence of Exon 2 of HLA-C site in Sample No. 1, as illustrated in FIG. 18. For all 950 samples, the typing results obtained by the above method were completely consistent with the original known typing results, wherein the results of Samples No. 1-32 were as followed:

| No. | Original known HLA-A/B/C/DQB1 type | | | | | | | |
|---|---|---|---|---|---|---|---|---|
| 1 | A*02:07 | A*03:01 | B*07:02 | B*46:01 | C*01:02 | C*07:02 | DQB1*03:03 | DQB1*06:02 |
| 2 | A*11:01 | A*31:01 | B*15:11 | B*38:02 | C*03:03 | C*07:02 | DQB1*03:03 | DQB1*04:01 |
| 3 | A*02:07 | A*24:02 | B*13:01 | B*46:01 | C*01:02 | C*03:04 | DQB1*03:02 | DQB1*06:01 |
| 4 | A*24:02 | A*33:03 | B*40:01 | B*51:01 | C*01:02 | C*14:02 | DQB1*03:03 | DQB1*03:03 |
| 5 | A*31:01 | A*31:01 | B*15:01 | B*35:01 | C*04:01 | C*04:01 | DQB1*03:02 | DQB1*06:02 |
| 6 | A*02:07 | A*03:01 | B*44:02 | B*46:01 | C*01:02 | C*05:01 | DQB1*03:01 | DQB1*06:02 |

-continued

| No. | Original known HLA-A/B/C/DQB1 type | | | | | | | |
|---|---|---|---|---|---|---|---|---|
| 7 | A*02:01 | A*30:01 | B*07:02 | B*13:02 | C*06:02 | C*07:02 | DQB1*02:02 | DQB1*06:01 |
| 8 | A*02:07 | A*02:07 | B*46:01 | B*46:01 | C*01:02 | C*01:02 | DQB1*05:02 | DQB1*03:03 |
| 9 | A*01:01 | A*33:03 | B*49:01 | B*58:01 | C*03:02 | C*07:01 | DQB1*06:04 | DQB1*06:09 |
| 10 | A*02:07 | A*11:01 | B*46:01 | B*48:01 | C*01:03 | C*08:01 | DQB1*05:03 | DQB1*03:02 |
| 11 | A*02:06 | A*30:01 | B*13:02 | B*15:02 | C*06:02 | C*08:01 | DQB1*03:01 | DQB1*03:01 |
| 12 | A*24:02 | A*31:01 | B*35:01 | B*51:01 | C*03:03 | C*14:02 | DQB1*03:03 | DQB1*06:01 |
| 13 | A*11:01 | A*33:03 | B*46:01 | B*46:01 | C*01:02 | C*01:02 | DQB1*03:02 | DQB1*03:03 |
| 14 | A*01:01 | A*02:03 | B*38:02 | B*57:01 | C*06:02 | C*07:02 | DQB1*05:02 | DQB1*03:03 |
| 15 | A*02:06 | A*24:02 | B*13:01 | B*15:25 | C*03:04 | C*07:02 | DQB1*03:01 | DQB1*06:01 |
| 16 | A*11:01 | A*24:02 | B*15:02 | B*15:27 | C*04:01 | C*08:01 | DQB1*03:03 | DQB1*03:03 |
| 17 | A*24:02 | A*24:02 | B*40:01 | B*46:01 | C*01:02 | C*03:04 | DQB1*03:03 | DQB1*06:02 |
| 18 | A*24:02 | A*24:02 | B*40:01 | B*46:01 | C*01:02 | C*03:04 | DQB1*03:03 | DQB1*06:02 |
| 19 | A*11:01 | A*33:03 | B*40:02 | B*58:01 | C*03:02 | C*03:04 | DQB1*02:01 | DQB1*03:02 |
| 20 | A*24:02 | A*30:01 | B*13:02 | B*40:01 | C*03:04 | C*06:02 | DQB1*06:03 | DQB1*06:03 |
| 21 | A*02:01 | A*24:02 | B*40:01 | B*40:01 | C*07:02 | C*14:02 | DQB1*04:02 | DQB1*06:02 |
| 22 | A*02:01 | A*33:03 | B*15:01 | B*44:03 | C*01:02 | C*14:03 | DQB1*03:01 | DQB1*06:04 |
| 23 | A*26:01 | A*33:03 | B*15:01 | B*58:01 | C*03:02 | C*08:01 | DQB1*02:01 | DQB1*03:01 |
| 24 | A*02:01 | A*11:01 | B*13:01 | B*55:02 | C*01:06 | C*03:04 | DQB1*03:01 | DQB1*03:03 |
| 25 | A*02:01 | A*32:01 | B*40:01 | B*52:01 | C*03:04 | C*12:02 | DQB1*05:02 | DQB1*06:01 |
| 26 | A*02:03 | A*02:07 | B*40:01 | B*46:01 | C*01:02 | C*07:02 | DQB1*03:02 | DQB1*06:01 |
| 27 | A*02:07 | A*02:07 | B*46:01 | B*46:01 | C*01:02 | C*01:02 | DQB1*03:03 | DQB1*06:01 |
| 28 | A*24:02 | A*30:01 | B*13:02 | B*39:05 | C*06:02 | C*07:02 | DQB1*02:02 | DQB1*06:01 |
| 29 | A*31:01 | A*33:03 | B*15:18 | B*58:01 | C*03:02 | C*07:04 | DQB1*04:01 | DQB1*06:09 |
| 30 | A*02:06 | A*03:01 | B*27:05 | B*40:02 | C*02:02 | C*03:04 | DQB1*03:01 | DQB1*03:01 |
| 31 | A*02:06 | A*33:03 | B*15:02 | B*58:01 | C*03:02 | C*08:01 | DQB1*05:01 | DQB1*06:01 |
| 32 | A*03:01 | A*30:01 | B*13:02 | B*51:01 | C*06:02 | C*15:02 | DQB1*02:02 | DQB1*03:01 |

| No. | HLA-A/B/C/DQB1 type determined by the method of the invention | | | | | | | |
|---|---|---|---|---|---|---|---|---|
| 1 | A*02:07 | A*03:01 | B*07:02 | B*46:01 | C*01:02 | C*07:02 | DQB1*03:03 | DQB1*06:02 |
| 2 | A*11:01 | A*31:01 | B*15:11 | B*38:02 | C*03:03 | C*07:02 | DQB1*03:03 | DQB1*04:01 |
| 3 | A*02:07 | A*24:02 | B*13:01 | B*46:01 | C*01:02 | C*03:04 | DQB1*03:02 | DQB1*06:01 |
| 4 | A*24:02 | A*33:03 | B*40:01 | B*51:01 | C*01:02 | C*14:02 | DQB1*03:03 | DQB1*03:03 |
| 5 | A*31:01 | A*31:01 | B*15:01 | B*35:01 | C*04:01 | C*04:01 | DQB1*03:02 | DQB1*06:02 |
| 6 | A*02:07 | A*03:01 | B*44:02 | B*46:01 | C*01:02 | C*05:01 | DQB1*03:01 | DQB1*06:02 |
| 7 | A*02:01 | A*30:01 | B*07:02 | B*13:02 | C*06:02 | C*07:02 | DQB1*02:02 | DQB1*06:01 |
| 8 | A*02:07 | A*02:07 | B*46:01 | B*46:01 | C*01:02 | C*01:02 | DQB1*05:02 | DQB1*03:03 |
| 9 | A*01:01 | A*33:03 | B*49:01 | B*58:01 | C*03:02 | C*07:01 | DQB1*06:04 | DQB1*06:09 |

| No. | HLA-A/B/C/DQB1 type determined by the method of the invention | | | | | | | |
|---|---|---|---|---|---|---|---|---|
| 10 | A*02:07 | A*11:01 | B*46:01 | B*48:01 | C*01:03 | C*08:01 | DQB1*05:03 | DQB1*03:02 |
| 11 | A*02:06 | A*30:01 | B*13:02 | B*15:02 | C*06:02 | C*08:01 | DQB1*03:01 | DQB1*03:01 |
| 12 | A*24:02 | A*31:01 | B*35:01 | B*51:01 | C*03:03 | C*14:02 | DQB1*03:03 | DQB1*06:01 |
| 13 | A*11:01 | A*33:03 | B*46:01 | B*46:01 | C*01:02 | C*01:02 | DQB1*03:02 | DQB1*03:03 |
| 14 | A*01:01 | A*02:03 | B*38:02 | B*57:01 | C*06:02 | C*07:02 | DQB1*05:02 | DQB1*03:03 |
| 15 | A*02:06 | A*24:02 | B*13:01 | B*15:25 | C*03:04 | C*07:02 | DQB1*03:01 | DQB1*06:01 |
| 16 | A*11:01 | A*24:02 | B*15:02 | B*15:27 | C*04:01 | C*08:01 | DQB1*03:01 | DQB1*03:03 |
| 17 | A*24:02 | A*24:02 | B*40:01 | B*46:01 | C*01:02 | C*03:04 | DQB1*03:03 | DQB1*06:02 |
| 18 | A*24:02 | A*24:02 | B*40:01 | B*46:01 | C*01:02 | C*03:04 | DQB1*03:03 | DQB1*06:02 |
| 19 | A*11:01 | A*33:03 | B*40:02 | B*58:01 | C*03:02 | C*03:04 | DQB1*02:01 | DQB1*03:02 |
| 20 | A*24:02 | A*30:01 | B*13:02 | B*40:01 | C*03:04 | C*06:02 | DQB1*06:02 | DQB1*06:03 |
| 21 | A*02:01 | A*24:02 | B*40:01 | B*40:01 | C*07:02 | C*14:02 | DQB1*04:02 | DQB1*06:02 |
| 22 | A*02:01 | A*33:03 | B*15:01 | B*44:03 | C*01:02 | C*14:03 | DQB1*03:01 | DQB1*06:04 |
| 23 | A*26:01 | A*33:03 | B*15:01 | B*58:01 | C*03:02 | C*08:01 | DQB1*02:01 | DQB1*03:01 |
| 24 | A*02:01 | A*11:01 | B*13:01 | B*55:02 | C*01:06 | C*03:04 | DQB1*03:01 | DQB1*03:03 |
| 25 | A*02:01 | A*32:01 | B*40:01 | B*52:01 | C*03:04 | C*12:02 | DQB1*05:02 | DQB1*06:01 |
| 26 | A*02:03 | A*02:07 | B*40:01 | B*46:01 | C*01:02 | C*07:02 | DQB1*03:02 | DQB1*06:01 |
| 27 | A*02:07 | A*02:07 | B*46:01 | B*46:01 | C*01:02 | C*01:02 | DQB1*03:03 | DQB1*06:01 |
| 28 | A*24:02 | A*30:01 | B*13:02 | B*39:05 | C*06:02 | C*07:02 | DQB1*02:02 | DQB1*06:01 |
| 29 | A*31:01 | A*33:03 | B*15:18 | B*58:01 | C*03:02 | C*07:04 | DQB1*04:01 | DQB1*06:09 |
| 30 | A*02:06 | A*03:01 | B*27:05 | B*40:02 | C*02:02 | C*03:04 | DQB1*03:01 | DQB1*03:01 |
| 31 | A*02:06 | A*33:03 | B*15:02 | B*58:01 | C*03:02 | C*08:01 | DQB1*05:01 | DQB1*06:01 |
| 32 | A*03:01 | A*30:01 | B*13:02 | B*51:01 | C*06:02 | C*15:02 | DQB1*02:02 | DQB1*03:01 |

Notice:
In case that the sequences of Exons 2, 3, 4 of HLA-A/B/C were completely identical, a common type was selected.

950 samples with known HLA-SBT typing results were subjected to genotyping of HLA-A/B/C/DQB1 sites by the technical strategy of the present invention, and the results showed that the typing results obtained by the technical strategy of the present invention were completely consistent with the original known results.

Although the embodiments of the present invention have been already described in detail, a person skilled in the art would understand that based on all the teaching as disclosed, various modification and substitution may be made to the embodiments without departing from the spirit and scope of the present invention. The scope of the present invention is defined by the claims appended and any equivalent thereof.

REFERENCES

[2]. Tiercy J M. Molecular basis of HLA polymorphism: implications in clinical transplantation. [J]. Transpl Immunol, 2002, 9: 173-180.

[3]. C. Antoine, S. Müller, A. Cant, et al. Long-term survival and transplantation of haemopoietic stem cells for immunodeficiencies: report of the European experience. 1968-99. [J]. The Lancet, 2003, 9357:553-560.

[4]. H. A. Erlich, G. Opelz, J. Hansen, et al. HLA DNA Typing and Transplantation. [J]. Immunity, 2001, 14:347-356.

[5]. Lillo R, Balas A, Vicario J L, et al. Two new HLA class allele, DPB1*02014, by sequence-based typing. [J]. Tissue Antigens, 2002, 59: 47-48.

[6], A. Dormoy, N. Froelich. Leisenbach, et al. Mono-allelic amplification of exons 2-4 using allele group-specific primers for sequence-based typing (SBT) of the HLA-A, -B and -C genes: Preparation and validation of ready-to-use pre-SBT mini-kits, [J]. Tissue Antigens, 2003, 62: 201-216.

[7]. Elaine R. Mardis. The impact of next-generation sequencing technology on genetics. [J]. Trends in Genetics. 2008, 24:133-141.

[8]. Christian Hoffmannl, Nana Minkahl, Jeremy Leipzig. DNA barcoding and pyrosequencing to identify rare HIV drug resistance mutations. [J]. Nucleic Acids Research, 2007, 1-8.

[9]. Shannon J. Odelberg, Robert B. Weiss, Akira Hata. Template-switching during DNA synthesis by *Thermus aquaticus* DNA polymerase I. [J]. Nucleic Acids Research. 1995, 23:2049-2057.

[10]. Sayer D, Whidborne R, Brestovac B. HLA-DRB1 DNA sequencing based typing: an approach suitable for high throughput typing including unrelated bone marrow registry donors. [J]. Tissue Antigens. 2001, 57(1):46-54.

[11]. Iwanka Kozarewa, Zemin Ning, Michael A Quail. Amplification-free Illumina sequencing-library preparation facilitates improved mapping and assembly of (G+C)-biased genomes. [J]. Nature Methods. 2009, 6: 291-295.

[12] Marsh, S. G. E., Parham, P. & Barber, L. D. The HLA Facts Book 3-91 (Academic Press, London, 2000).

[13] Campbell, K. J. et al. Characterization of 47 MHC class I sequences in Filipino cynomolgus macaques. Immunogenetics 61, 177-187 (2009).

[14] Goulder, P. J. R. & Watkins, D. I. Impact of MHC class I diversity on immune control of immunodeficiency virus replication. Nat. Rev. Immunol. 8, 619-630 (2008).

[15] O'Leary, C. E. et al. Identification of novel MHC class I sequences in pig-tailed macaques by amplicon pyrosequencing and full-length cDNA cloning and sequencing. Immunogenetics 61, 689-701 (2009).

[16] Robinson J, Malik A, Parham P, Bodmer J G, Marsh S G E. IMGT/HLA database-a sequence database for the human major histocompatibility complex. Tissue Antigens 55, 80-7 (2000).

[17] Hoffmann C, Minkah N, Leipzig J, Wang G, Arens M Q, Tebas P, Bushman F D. DNA bar coding and pyrosequencing to identify rare HIV drug resistance mutations. Nucleic Acids Res. 2007; 35(13):e91.

[18]. WU, D. L. et al. Comparative analysis of serologic typing and HLA-II typing by micro-PCR-SSP. Di Yi Jun Yi Da Xue Xue Bao, 2002, 22:247-249.

[19]. Al-Hussein K A, Rama N R, Butt A I, et al. HLA class II sequence based typing in normal Saudi individuals. Tissue Antigens, 2002, 60: 259-261.

[20]. D. C. Sayer, D. M. Goodridge. Pilot study: assessment of interlaboratory variability of sequencing-based typing DNA sequence data quality. Tissue Antigens, 2007, 69 Suppl: 66-68.

[21]. Horton V, Stratton I, Bottazzo G. F. et al. Genetic heterogeneity of autoimmune diabetes: age of presentation in adults is influenced by HLA DRB1 and DQB1 genotypes. Diabetologia, 1999, 42:608-616.

[22]. C. E. M. Voorter, M. C. Kikl, E. M. van den Berg-Loonen et al. High-resolution HLA typing for the DQB1 gene by sequence-based typing. Tissue Antigens, 2008, 51:80-87.

[23]. G. Bentley, R. Higuchi, B. Hoglund et al. High-resolution, high-throughput HLA genotyping by next-generation sequencing. Tissue Antigens, 2009, 74: 393-403.

The invention claimed is:

1. A method for determining the nucleotide sequence of a nucleic acid of interest, comprising:

a) providing n samples, wherein n is an integer of ≥1;

b) optionally dividing the n samples into m groups, wherein m is an integer and n≥m≥1;

c) performing PCR amplification on the samples under conditions suitable for amplifying the nucleic acid of interest when templates from the samples are available, wherein a pair or multiple pairs of index primers are used for each sample, each pair of index primers consists of a forward index primer and a reverse index primer, and each index primer consists of a PCR primer and a primer index added to the 5'-end of the PCR primer, wherein the primer index of the forward index primer and the primer index of the reverse index primer in each pair of index primers are identical or different, and wherein the primer indexes in the pair of index primers used for different samples are different;

d) pooling products of the PCR amplification from each of the samples together;

e) subjecting the amplified products to incomplete shearing to obtain a mixture of intact un-sheared PCR products and partially sheared PCR products, and purifying and recovering said mixture of intact un-sheared PCR products and partially sheared PCR products;

f) constructing a PCR-free sequencing library based on the mixture of intact un-sheared PCR products and partially sheared PCR products recovered in e), wherein different library adapters are added to distinguish different PCR-Free sequencing libraries;

g) purifying and recovering DNA bands between the maximum read length and the maximum applicable DNA length of a sequencer using the second generation sequencing technique;

h) subjecting the recovered DNA mixture to the sequencer to obtain sequences of the sheared DNA; and i) matching obtained sequencing data to corresponding samples based on a unique primer index for each sample, aligning obtained sequences of the sheared DNA against DNA reference sequences corresponding to the PCR products, and assembling a complete sequence of the nucleic acid of interest from the obtained sequences of the sheared DNA based on sequence overlap and linkage relationship, whereby a length of the complete sequence of the nucleic acid of interest exceeds a maximum read length of a sequencer used for said sequencing.

2. The method of claim 1, wherein:

a) said PCR primers are PCR primers for amplification of HLA gene, HLA-A/B gene, Exons 2, 3 and 4 of HLA-A/B, or Exon 2 of HLA-DRB1;

b) said PCR primers are PCR primers for amplification of Exons 2, 3 and 4 of HLA-A/B as shown in SEQ ID NO: 1, 2, 3, 4, 5, 6, 7, 8, 9, 10, 11 and 12;

c) said PCR primers are PCR primers for amplification of Exons 2, 3 and 4 of HLA-A/B as shown in SEQ ID NO: 13, 14, 15, 16, 17, 18, 19, 20, 21, 22, 23 and 24;

d) said PCR primers are PCR primers for amplification of Exon 2 of HLA-DRB1 as shown in SEQ ID NO: 231, 232, 233, 234, 235, 236, 237 and 238;

e) said PCR primers are PCR primers for amplification of HLA gene, HLA-C gene, or Exons 2, 3 and/or 4 of HLA-C;

f) said PCR primers are PCR primers for amplification of Exons 2, 3 and/or 4 of HLA-C as shown in SEQ ID NO: 25, 26, 27, 28, 29 and 30;

g) said PCR primers are PCR primers for amplification of Exons 2, 3 and/or 4 of HLA-C as shown in SEQ ID NO: 31, 32, 33, 34, 35 and 36;

h) said PCR primers are PCR primers for amplification of HLA gene, HLA-DQB1 gene, or Exon 2 and/3 of HLA-DQB1 gene; or i) said PCR primers are PCR primers for amplification of Exon 2 and/3 of HLA-DQB1 gene as shown in SEQ ID NO: 37, 38, 39 and 40.

3. The method of claim 1, wherein said primer indexes are designed for:

a) PCR primers for amplification of a specific gene of HLA;

b) PCR primers for amplification of Exons 2, 3 and 4 of HLA-A/B and Exon 2 of HLA-DRB1;

c) PCR primers shown in SEQ ID NO: 1, 2, 3, 4, 5, 6, 7, 8, 9, 10, 11 and 12;

d) PCR primers shown in SEQ ID NO: 13, 14, 15, 16, 17, 18, 19, 20, 21, 22, 23 and 24; or e) PCR primers shown in SEQ ID NO: 231, 232, 233, 234, 235, 236, 237 and 238.

4. The method of claim 1, wherein at least 10 pairs of primer indexes selected from the group consisting of primer index Nos. PI-1 to PI-95 as set forth in the table below are used

| Primer index No. | Forward primer index | Reverse primer index |
|---|---|---|
| PI-1 | SEQ ID NO: 41 | SEQ ID NO: 42 |
| PI-2 | SEQ ID NO: 43 | SEQ ID NO: 44 |
| PI-3 | SEQ ID NO: 45 | SEQ ID NO: 46 |

-continued

| Primer index No. | Forward primer index | Reverse primer index |
|---|---|---|
| PI-4 | SEQ ID NO: 47 | SEQ ID NO: 48 |
| PI-5 | SEQ ID NO: 49 | SEQ ID NO: 50 |
| PI-6 | SEQ ID NO: 51 | SEQ ID NO: 52 |
| PI-7 | SEQ ID NO: 53 | SEQ ID NO: 54 |
| PI-8 | SEQ ID NO: 55 | SEQ ID NO: 56 |
| PI-9 | SEQ ID NO: 57 | SEQ ID NO: 58 |
| PI-10 | SEQ ID NO: 59 | SEQ ID NO: 60 |
| PI-11 | SEQ ID NO: 61 | SEQ ID NO: 62 |
| PI-12 | SEQ ID NO: 63 | SEQ ID NO: 64 |
| PI-13 | SEQ ID NO: 65 | SEQ ID NO: 66 |
| PI-14 | SEQ ID NO: 67 | SEQ ID NO: 68 |
| PI-15 | SEQ ID NO: 69 | SEQ ID NO: 70 |
| PI-16 | SEQ ID NO: 71 | SEQ ID NO: 72 |
| PI-17 | SEQ ID NO: 73 | SEQ ID NO: 74 |
| PI-18 | SEQ ID NO: 75 | SEQ ID NO: 76 |
| PI-19 | SEQ ID NO: 77 | SEQ ID NO: 78 |
| PI-20 | SEQ ID NO: 79 | SEQ ID NO: 80 |
| PI-21 | SEQ ID NO: 81) | SEQ ID NO: 82 |
| PI-22 | SEQ ID NO: 83 | SEQ ID NO: 84 |
| PI-23 | SEQ ID NO: 85 | SEQ ID NO: 86 |
| PI-24 | SEP ID NO: 87 | SEQ ID NO: 88 |
| PI-25 | SEQ ID NO: 89 | SEQ ID NO: 90 |
| PI-26 | SEQ ID NO: 91 | SEQ ID NO: 92 |
| PI-27 | SEQ ID NO: 93 | SEQ ID NO: 94 |
| PI-28 | SEQ ID NO: 95 | SEQ ID NO: 96 |
| PI-29 | SEQ ID NO: 97 | SEQ ID NO: 98 |
| PI-30 | SEQ ID NO: 99 | SEQ ID NO: 100 |
| PI-31 | SEQ ID NO: 101 | SEQ ID NO: 102 |
| PI-32 | SEQ ID NO: 103 | SEQ ID NO: 104 |
| PI-33 | SEQ ID NO: 105 | SEQ ID NO: 106 |
| PI-34 | SEQ ID NO: 107 | SEQ ID NO: 108 |
| PI-35 | SEQ ID NO: 109 | SEQ ID NO: 110 |
| PI-36 | SEQ ID NO: 111 | SEQ ID NO: 112 |
| PI-37 | SEQ ID NO: 113 | SEQ ID NO: 114 |
| PI-38 | SEQ ID NO: 115 | SEQ ID NO: 116 |
| PI-39 | SEQ ID NO: 117 | SEQ ID NO: 118 |
| PI-40 | SEQ ID NO: 119 | SEQ ID NO: 120 |
| PI-41 | SEQ ID NO: 121 | SEQ ID NO: 122 |
| PI-42 | SEQ ID NO: 123 | SEQ ID NO: 124 |
| PI-43 | SEQ ID NO: 125 | SEQ ID NO: 126 |
| PI-44 | SEQ ID NO: 127 | SEQ ID NO: 128 |
| PI-45 | SEQ ID NO: 129 | SEQ ID NO: 130 |
| PI-46 | SEQ ID NO: 131 | SEQ ID NO: 132 |
| PI-47 | SEQ ID NO: 133 | SEQ ID NO: 134 |
| PI-48 | SEQ ID NO: 135 | SEQ ID NO: 136 |
| PI-49 | SEQ ID NO: 137 | SEQ ID NO: 138 |
| PI-50 | SEQ ID NO: 139 | SEQ ID NO: 140 |
| PI-51 | SEQ ID NO: 141 | SEQ ID NO: 142 |
| PI-52 | SEQ ID NO: 143 | SEQ ID NO: 144 |
| PI-53 | SEQ ID NO: 145 | SEQ ID NO: 146 |
| PI-54 | SEQ ID NO: 147 | SEQ ID NO: 148 |
| PI-55 | SEQ ID NO: 149 | SEQ ID NO: 150 |
| PI-56 | SEQ ID NO: 151 | SEQ ID NO: 152 |
| PI-57 | SEQ ID NO: 153 | SEQ ID NO: 154 |
| PI-58 | SEQ ID NO: 155 | SEQ ID NO: 156 |
| PI-59 | SEQ ID NO: 157 | SEQ ID NO: 158 |
| PI-60 | SEQ ID NO: 159 | SEQ ID NO: 160 |
| PI-61 | SEQ ID NO: 161 | SEQ ID NO: 162 |
| PI-62 | SEQ ID NO: 163 | SEQ ID NO: 164 |
| PI-63 | SEQ ID NO: 165 | SEQ ID NO: 166 |
| PI-64 | SEQ ID NO: 167 | SEQ ID NO: 168 |
| PI-65 | SEQ ID NO: 169 | SEQ ID NO: 170 |
| PI-66 | SEQ ID NO: 171 | SEQ ID NO: 172 |
| PI-67 | SEQ ID NO: 173 | SEQ ID NO: 174 |
| PI-68 | SEQ ID NO: 175 | SEQ ID NO: 176 |
| PI-69 | SEQ ID NO: 177 | SEQ ID NO: 178 |
| PI-70 | SEQ ID NO: 179 | SEQ ID NO: 180 |
| PI-71 | SEQ ID NO: 181 | SEQ ID NO: 182 |
| PI-72 | SEQ ID NO: 183 | SEQ ID NO: 184 |
| PI-73 | SEQ ID NO: 185 | SEQ ID NO: 186 |
| PI-74 | SEQ ID NO: 187 | SEQ ID NO: 188 |
| PI-75 | SEQ ID NO: 189 | SEQ ID NO: 190 |
| PI-76 | SEQ ID NO: 191 | SEQ ID NO: 192 |
| PI-77 | SEQ ID NO: 193 | SEQ ID NO: 194 |
| PI-78 | SEQ ID NO: 195 | SEQ ID NO: 196 |
| PI-79 | SEQ ID NO: 197 | SEQ ID NO: 198 |

-continued

| Primer index No. | Forward primer index | Reverse primer index |
|---|---|---|
| PI-80 | SEQ ID NO: 199 | SEQ ID NO: 200 |
| PI-81 | SEQ ID NO: 201 | SEQ ID NO: 202 |
| PI-82 | SEQ ID NO: 203 | SEQ ID NO: 204 |
| PI-83 | SEQ ID NO: 205 | SEQ ID NO: 206 |
| PI-84 | SEQ ID NO: 207 | SEQ ID NO: 208 |
| PI-85 | SEQ ID NO: 209 | SEQ ID NO: 210 |
| PI-86 | SEQ ID NO: 211 | SEQ ID NO: 212 |
| PI-87 | SEQ ID NO: 213 | SEQ ID NO: 214 |
| PI-88 | SEQ ID NO: 215 | SEQ ID NO: 216 |
| PI-89 | SEQ ID NO: 217 | SEQ ID NO: 218 |
| PI-90 | (SEQ ID NO: 219 | SEQ ID NO: 220 |
| PI-91 | (SEQ ID NO: 221 | SEQ ID NO: 222 |
| PI-92 | SEQ ID NO: 223 | SEQ ID NO: 224 |
| PI-93 | SEQ ID NO: 225 | SEQ ID NO: 226 |
| PI-94 | SEQ ID NO: 227 | SEQ ID NO: 228 |
| PI-95 | SEQ ID NO: 229 | SEQ ID NO: 230. |

5. The method of claim 1, wherein said DNA shearing is performed by chemical shearing and/or physical shearing.

6. The method of claim 5, wherein said chemical shearing comprises enzymatic digestion.

7. The method of claim 5, wherein said physical shearing comprises ultrasonic shearing or mechanical shearing.

8. The method of claim 1, wherein, in step g), the DNA bands between the maximum read length and the maximum applicable DNA length of the second generation sequencer are purified and recovered by electrophoresis and gel slicing, or by magnetic beads.

9. The method of claim 1, wherein the sample is from human.

10. The method of claim 9, wherein the sample is human blood.

11. The method of claim 1, wherein the sequencer uses Paired-End technique.

12. The method of claim 1, wherein the sequencer is a Hiseq 2000 sequencer, an Illumina GA sequencer, an Illumina Solexa sequencer, or a Roche454 sequencer.

13. The method of claim 1, wherein the DNA bands purified and recovered in step g) have a length ranging from 450 bp to 700 bp, and wherein the sequencer is an Illumina GA sequencer.

14. A method of determining HLA genotype of a sample, comprising:
   a) sequencing a sample from a patient by the method of claim 2;
   b) aligning the sequencing results against sequence data of Exons of HLA, Exons 2, 3 and 4 of HLA-A/B, Exons 2, 3 and/or Exon 4 of HLA-C, Exon 2 and/or 3 of HLA-DQB1 gene and/or Exon 2 of HLA-DRB1 in HLA database; and
   c) determine the HLA genotype of the sample if the result of sequence alignment shows 100% match.

15. The method of claim 14, wherein said primer indexes are designed for:
   a) PCR primers for amplification of a specific gene of HLA;
   b) PCR primers for amplification of Exons 2, 3 and 4 of HLA-A/B and Exon 2 of HLA-DRB1;
   c) PCR primers shown in SEQ ID NO: 1, 2, 3, 4, 5, 6, 7, 8, 9, 10, 11 and 12;
   d) PCR primers shown in SEQ ID NO: 13, 14, 15, 16, 17, 18, 19, 20, 21, 22, 23 and 24; or
   e) PCR primers shown in SEQ ID NO: 231, 232, 233, 234, 235, 236, 237 and 238.

16. The method of claim 14, wherein at least 10 pairs of primer indexes selected from the group consisting of primer index Nos. PI-1 to PI-95 as set forth in the table below are used

| Primer index No. | Forward primer index | Reverse primer index |
|---|---|---|
| PI-1 | SEQ ID NO: 41 | SEQ ID NO: 42 |
| PI-2 | SEQ ID NO: 43 | SEQ ID NO: 44 |
| PI-3 | SEQ ID NO: 45 | SEQ ID NO: 46 |
| PI-4 | SEQ ID NO: 47 | SEQ ID NO: 48 |
| PI-5 | SEQ ID NO: 49 | SEQ ID NO: 50 |
| PI-6 | SEQ ID NO: 51 | SEQ ID NO: 52 |
| PI-7 | SEQ ID NO: 53 | SEQ ID NO: 54 |
| PI-8 | SEQ ID NO: 55 | SEQ ID NO: 56 |
| PI-9 | SEQ ID NO: 57 | SEQ ID NO: 58 |
| PI-10 | SEQ ID NO: 59 | SEQ ID NO: 60 |
| PI-11 | SEQ ID NO: 61 | SEQ ID NO: 62 |
| PI-12 | SEQ ID NO: 63 | SEQ ID NO: 64 |
| PI-13 | SEQ ID NO: 65 | SEQ ID NO: 66 |
| PI-14 | SEQ ID NO: 67 | SEQ ID NO: 68 |
| PI-15 | SEQ ID NO: 69 | SEQ ID NO: 70 |
| PI-16 | SEQ ID NO: 71 | SEQ ID NO: 72 |
| PI-17 | SEQ ID NO: 73 | SEQ ID NO: 74 |
| PI-18 | SEQ ID NO: 75 | SEQ ID NO: 76 |
| PI-19 | SEQ ID NO: 77 | SEQ ID NO: 78 |
| PI-20 | SEQ ID NO: 79 | SEQ ID NO: 80 |
| PI-21 | SEQ ID NO: 81) | SEQ ID NO: 82 |
| PI-22 | SEQ ID NO: 83 | SEQ ID NO: 84 |
| PI-23 | SEQ ID NO: 85 | SEQ ID NO: 86 |
| PI-24 | SEQ ID NO: 87 | SEQ ID NO: 88 |
| PI-25 | SEQ ID NO: 89 | SEQ ID NO: 90 |
| PI-26 | SEQ ID NO: 91 | SEQ ID NO: 92 |
| PI-27 | SEQ ID NO: 93 | SEQ ID NO: 94 |
| PI-28 | SEQ ID NO: 95 | SEQ ID NO: 96 |
| PI-29 | SEQ ID NO: 97 | SEQ ID NO: 98 |
| PI-30 | SEQ ID NO: 99 | SEQ ID NO: 100 |
| PI-31 | SEQ ID NO: 101 | SEQ ID NO: 102 |
| PI-32 | SEQ ID NO: 103 | SEQ ID NO: 104 |
| PI-33 | SEQ ID NO: 105 | SEQ ID NO: 106 |
| PI-34 | SEQ ID NO: 107 | SEQ ID NO: 108 |
| PI-35 | SEQ ID NO: 109 | SEQ ID NO: 110 |
| PI-36 | SEQ ID NO: 111 | SEQ ID NO: 112 |
| PI-37 | SEQ ID NO: 113 | SEQ ID NO: 114 |
| PI-38 | SEQ ID NO: 115 | SEQ ID NO: 116 |
| PI-39 | SEQ ID NO: 117 | SEQ ID NO: 118 |
| PI-40 | SEQ ID NO: 119 | SEQ ID NO: 120 |
| PI-41 | SEQ ID NO: 121 | SEQ ID NO: 122 |
| PI-42 | SEQ ID NO: 123 | SEQ ID NO: 124 |
| PI-43 | SEQ ID NO: 125 | SEQ ID NO: 126 |
| PI-44 | SEQ ID NO: 127 | SEQ ID NO: 128 |
| PI-45 | SEQ ID NO: 129 | SEQ ID NO: 130 |
| PI-46 | SEQ ID NO: 131 | SEQ ID NO: 132 |
| PI-47 | SEQ ID NO: 133 | SEQ ID NO: 134 |
| PI-48 | SEQ ID NO: 135 | SEQ ID NO: 136 |
| PI-49 | SEQ ID NO: 137 | SEQ ID NO: 138 |
| PI-50 | SEQ ID NO: 139 | SEQ ID NO: 140 |
| PI-51 | SEQ ID NO: 141 | SEQ ID NO: 142 |
| PI-52 | SEQ ID NO: 143 | SEQ ID NO: 144 |
| PI-53 | SEQ ID NO: 145 | SEQ ID NO: 146 |
| PI-54 | SEQ ID NO: 147 | SEQ ID NO: 148 |
| PI-55 | SEQ ID NO: 149 | SEQ ID NO: 150 |
| PI-56 | SEQ ID NO: 151 | SEQ ID NO: 152 |
| PI-57 | SEQ ID NO: 153 | SEQ ID NO: 154 |
| PI-58 | SEQ ID NO: 155 | SEQ ID NO: 156 |
| PI-59 | SEQ ID NO: 157 | SEQ ID NO: 158 |
| PI-60 | SEQ ID NO: 159 | SEQ ID NO: 160 |
| PI-61 | SEQ ID NO: 161 | SEQ ID NO: 162 |
| PI-62 | SEQ ID NO: 163 | SEQ ID NO: 164 |
| PI-63 | SEQ ID NO: 165 | SEQ ID NO: 166 |
| PI-64 | SEQ ID NO: 167 | SEQ ID NO: 168 |
| PI-65 | SEQ ID NO: 169 | SEQ ID NO: 170 |
| PI-66 | SEQ ID NO: 171 | SEQ ID NO: 172 |
| PI-67 | SEQ ID NO: 173 | SEQ ID NO: 174 |
| PI-68 | SEQ ID NO: 175 | SEQ ID NO: 176 |
| PI-69 | SEQ ID NO: 177 | SEQ ID NO: 178 |
| PI-70 | SEQ ID NO: 179 | SEQ ID NO: 180 |
| PI-71 | SEQ ID NO: 181 | SEQ ID NO: 182 |
| PI-72 | SEQ ID NO: 183 | SEQ ID NO: 184 |

-continued

| Primer index No. | Forward primer index | Reverse primer index |
|---|---|---|
| PI-73 | SEQ ID NO: 185 | SEQ ID NO: 186 |
| PI-74 | SEQ ID NO: 187 | SEQ ID NO: 188 |
| PI-75 | SEQ ID NO: 189 | SEQ ID NO: 190 |
| PI-76 | SEQ ID NO: 191 | SEQ ID NO: 192 |
| PI-77 | SEQ ID NO: 193 | SEQ ID NO: 194 |
| PI-78 | SEQ ID NO: 195 | SEQ ID NO: 196 |
| PI-79 | SEQ ID NO: 197 | SEQ ID NO: 198 |
| PI-80 | SEQ ID NO: 199 | SEQ ID NO: 200 |
| PI-81 | SEQ ID NO: 201 | SEQ ID NO: 202 |
| PI-82 | SEQ ID NO: 203 | SEQ ID NO: 204 |
| PI-83 | SEQ ID NO: 205 | SEQ ID NO: 206 |
| PI-84 | SEQ ID NO: 207 | SEQ ID NO: 208 |
| PI-85 | SEQ ID NO: 209 | SEQ ID NO: 210 |
| PI-86 | SEQ ID NO: 211 | SEQ ID NO: 212 |
| PI-87 | SEQ ID NO: 213 | SEQ ID NO: 214 |
| PI-88 | SEQ ID NO: 215 | SEQ ID NO: 216 |
| PI-89 | SEQ ID NO: 217 | SEQ ID NO: 218 |
| PI-90 | (SEQ ID NO: 219 | SEQ ID NO: 220 |
| PI-91 | (SEQ ID NO: 221 | SEQ ID NO: 222 |
| PI-92 | SEQ ID NO: 223 | SEQ ID NO: 224 |
| PI-93 | SEQ ID NO: 225 | SEQ ID NO: 226 |
| PI-94 | SEQ ID NO: 227 | SEQ ID NO: 228 |
| PI-95 | SEQ ID NO: 229 | SEQ ID NO: 230. |

17. The method of claim 14, wherein said DNA shearing is performed by chemical shearing and/or physical shearing, wherein said chemical shearing comprises enzymatic digestion, and wherein said physical shearing comprises ultrasonic shearing or mechanical shearing.

18. The method of claim 14, wherein the sample is from human.

19. The method of claim 18, wherein the sample is human blood.

20. The method of claim 14, wherein the DNA bands purified and recovered for sequencing have a length ranging from 450 bp to 700 bp, and wherein the second generation sequencer is an Illumina GA sequencer.

* * * * *

```
                       SEQUENCE LISTING

<160> NUMBER OF SEQ ID NOS: 269

<210> SEQ ID NO 1
<211> LENGTH: 19
<212> TYPE: DNA
<213> ORGANISM: Artificial Sequence
<220> FEATURE:
<223> OTHER INFORMATION: Synthetic PCR Primer for Amplifying Exon 2 of
      HLA-A gene.

<400> SEQUENCE: 1
cctctgyggg gagaagcaa                                                  19

<210> SEQ ID NO 2
<211> LENGTH: 19
<212> TYPE: DNA
<213> ORGANISM: Artificial Sequence
<220> FEATURE:
<223> OTHER INFORMATION: Synthetic PCR Primer for Amplifying Exon 2 of
      HLA-A gene.

<400> SEQUENCE: 2
atctcggacc cggagactg                                                  19

<210> SEQ ID NO 3
<211> LENGTH: 19
<212> TYPE: DNA
<213> ORGANISM: Artificial Sequence
<220> FEATURE:
<223> OTHER INFORMATION: Synthetic PCR Primer for Amplifying Exon 3 of
      HLA-A gene.

<400> SEQUENCE: 3
cggggccagg ttctcacac                                                  19

<210> SEQ ID NO 4
<211> LENGTH: 25
<212> TYPE: DNA
<213> ORGANISM: Artificial Sequence
```

```
<220> FEATURE:
<223> OTHER INFORMATION: Synthetic PCR Primer for Amplifying Exon 3 of
      HLA-A gene.

<400> SEQUENCE: 4
ggygatattc tagtgttggt cccaa                                              25

<210> SEQ ID NO 5
<211> LENGTH: 22
<212> TYPE: DNA
<213> ORGANISM: Artificial Sequence
<220> FEATURE:
<223> OTHER INFORMATION: Synthetic PCR Primer for Amplifying Exon 4 of
      HLA-A gene.

<400> SEQUENCE: 5
gtgtcccatg acagatgcaa aa                                                 22

<210> SEQ ID NO 6
<211> LENGTH: 20
<212> TYPE: DNA
<213> ORGANISM: Artificial Sequence
<220> FEATURE:
<223> OTHER INFORMATION: Synthetic PCR Primer for Amplifying Exon 4 of
      HLA-A gene.

<400> SEQUENCE: 6
ggccctgacc ctgctaaagg                                                    20

<210> SEQ ID NO 7
<211> LENGTH: 18
<212> TYPE: DNA
<213> ORGANISM: Artificial Sequence
<220> FEATURE:
<223> OTHER INFORMATION: Synthetic PCR Primer for Amplifying Exon 2 of
      HLA-B gene.

<400> SEQUENCE: 7
aggagcgagg ggaccgca                                                      18

<210> SEQ ID NO 8
<211> LENGTH: 18
<212> TYPE: DNA
<213> ORGANISM: Artificial Sequence
<220> FEATURE:
<223> OTHER INFORMATION: Synthetic PCR Primer for Amplifying Exon 2 of
      HLA-B gene.

<400> SEQUENCE: 8
cgggccgggg tcactcac                                                      18

<210> SEQ ID NO 9
<211> LENGTH: 18
<212> TYPE: DNA
<213> ORGANISM: Artificial Sequence
<220> FEATURE:
<223> OTHER INFORMATION: Synthetic PCR Primer for Amplifying Exon 3 of
      HLA-B gene.

<400> SEQUENCE: 9
cggggccagg gtctcaca                                                      18

<210> SEQ ID NO 10
<211> LENGTH: 18
<212> TYPE: DNA
<213> ORGANISM: Artificial Sequence
<220> FEATURE:
```

```
<223> OTHER INFORMATION: Synthetic PCR Primer for Amplifying Exon 3 of
      HLA-B gene.

<400> SEQUENCE: 10
gaggccatcc ccggcgac                                                   18

<210> SEQ ID NO 11
<211> LENGTH: 22
<212> TYPE: DNA
<213> ORGANISM: Artificial Sequence
<220> FEATURE:
<223> OTHER INFORMATION: Synthetic PCR Primer for Amplifying Exon 4 of
      HLA-B gene.

<400> SEQUENCE: 11
gctggtcaca tgggtggtcc ta                                              22

<210> SEQ ID NO 12
<211> LENGTH: 22
<212> TYPE: DNA
<213> ORGANISM: Artificial Sequence
<220> FEATURE:
<223> OTHER INFORMATION: Synthetic PCR Primer for Amplifying Exon 4 of
      HLA-B gene.

<400> SEQUENCE: 12
ctccttaccc catctcaggg tg                                              22

<210> SEQ ID NO 13
<211> LENGTH: 19
<212> TYPE: DNA
<213> ORGANISM: Artificial Sequence
<220> FEATURE:
<223> OTHER INFORMATION: Synthetic PCR Primer for Amplifying Exon 2 of
      HLA-A gene.

<400> SEQUENCE: 13
cctctgyggg gagaagcaa                                                  19

<210> SEQ ID NO 14
<211> LENGTH: 22
<212> TYPE: DNA
<213> ORGANISM: Artificial Sequence
<220> FEATURE:
<223> OTHER INFORMATION: Synthetic PCR Primer for Amplifying Exon 2 of
      HLA-A gene.

<400> SEQUENCE: 14
ggatctcgga cccggagact gt                                              22

<210> SEQ ID NO 15
<211> LENGTH: 18
<212> TYPE: DNA
<213> ORGANISM: Artificial Sequence
<220> FEATURE:
<223> OTHER INFORMATION: Synthetic PCR Primer for Amplifying Exon 3 of
      HLA-A gene.

<400> SEQUENCE: 15
tgggctgacc gyggggtc                                                   18

<210> SEQ ID NO 16
<211> LENGTH: 25
<212> TYPE: DNA
<213> ORGANISM: Artificial Sequence
<220> FEATURE:
<223> OTHER INFORMATION: Synthetic PCR Primer for Amplifying Exon 3 of
```

HLA-A gene.

<400> SEQUENCE: 16
ggygatattc tagtgttggt cccaa                                              25

<210> SEQ ID NO 17
<211> LENGTH: 22
<212> TYPE: DNA
<213> ORGANISM: Artificial Sequence
<220> FEATURE:
<223> OTHER INFORMATION: Synthetic PCR Primer for Amplifying Exon 4 of
      HLA-A gene.

<400> SEQUENCE: 17
gtgtcccatk acagatgcaa aa                                                 22

<210> SEQ ID NO 18
<211> LENGTH: 20
<212> TYPE: DNA
<213> ORGANISM: Artificial Sequence
<220> FEATURE:
<223> OTHER INFORMATION: Synthetic PCR Primer for Amplifying Exon 4 of
      HLA-A gene.

<400> SEQUENCE: 18
ggccctgacc ctgctaaagg                                                    20

<210> SEQ ID NO 19
<211> LENGTH: 18
<212> TYPE: DNA
<213> ORGANISM: Artificial Sequence
<220> FEATURE:
<223> OTHER INFORMATION: Synthetic PCR Primer for Amplifying Exon 2 of
      HLA-B gene.

<400> SEQUENCE: 19
aggagcgagg ggaccgca                                                      18

<210> SEQ ID NO 20
<211> LENGTH: 18
<212> TYPE: DNA
<213> ORGANISM: Artificial Sequence
<220> FEATURE:
<223> OTHER INFORMATION: Synthetic PCR Primer for Amplifying Exon 2 of
      HLA-B gene.

<400> SEQUENCE: 20
cgggccgggg tcactcac                                                      18

<210> SEQ ID NO 21
<211> LENGTH: 18
<212> TYPE: DNA
<213> ORGANISM: Artificial Sequence
<220> FEATURE:
<223> OTHER INFORMATION: Synthetic PCR Primer for Amplifying Exon 3 of
      HLA-B gene.

<400> SEQUENCE: 21
ccaaaatccc cgcgggtt                                                      18

<210> SEQ ID NO 22
<211> LENGTH: 18
<212> TYPE: DNA
<213> ORGANISM: Artificial Sequence
<220> FEATURE:
<223> OTHER INFORMATION: Synthetic PCR Primer for Amplifying Exon 2 of
      HLA-B gene.

```
<400> SEQUENCE: 22
gaggccatcc ccggcgac                                                 18

<210> SEQ ID NO 23
<211> LENGTH: 22
<212> TYPE: DNA
<213> ORGANISM: Artificial Sequence
<220> FEATURE:
<223> OTHER INFORMATION: Synthetic PCR Primer for Amplifying Exon 4 of
      HLA-B gene.

<400> SEQUENCE: 23
gctggtcaca tgggtggtcc ta                                            22

<210> SEQ ID NO 24
<211> LENGTH: 20
<212> TYPE: DNA
<213> ORGANISM: Artificial Sequence
<220> FEATURE:
<223> OTHER INFORMATION: Synthetic PCR Primer for Amplifying Exon 4 of
      HLA-B gene.

<400> SEQUENCE: 24
tgacccctca tccccctcct                                               20

<210> SEQ ID NO 25
<211> LENGTH: 18
<212> TYPE: DNA
<213> ORGANISM: Artificial Sequence
<220> FEATURE:
<223> OTHER INFORMATION: Synthetic PCR Primer for Amplifying Exon 2 of
      HLA-C gene.

<400> SEQUENCE: 25
gacccgggga gccgcgca                                                 18

<210> SEQ ID NO 26
<211> LENGTH: 19
<212> TYPE: DNA
<213> ORGANISM: Artificial Sequence
<220> FEATURE:
<223> OTHER INFORMATION: Synthetic PCR Primer for Amplifying Exon 2 of
      HLA-C gene.

<400> SEQUENCE: 26
tcgagggtct gggcgggtt                                                19

<210> SEQ ID NO 27
<211> LENGTH: 26
<212> TYPE: DNA
<213> ORGANISM: Artificial Sequence
<220> FEATURE:
<223> OTHER INFORMATION: Synthetic PCR Primer for Amplifying Exon 3 of
      HLA-C gene.

<400> SEQUENCE: 27
cctttacccg gtttcatttt crgttt                                        26

<210> SEQ ID NO 28
<211> LENGTH: 21
<212> TYPE: DNA
<213> ORGANISM: Artificial Sequence
<220> FEATURE:
<223> OTHER INFORMATION: Synthetic PCR Primer for Amplifying Exon 3 of
      HLA-C gene.
```

<400> SEQUENCE: 28
ctacgggaga tggggaaggc t                                          21

<210> SEQ ID NO 29
<211> LENGTH: 25
<212> TYPE: DNA
<213> ORGANISM: Artificial Sequence
<220> FEATURE:
<223> OTHER INFORMATION: Synthetic PCR Primer for Amplifying Exon 4 of
      HLA-C gene.

<400> SEQUENCE: 29
gtgtcgcaag agagatrcaa agtgt                                      25

<210> SEQ ID NO 30
<211> LENGTH: 22
<212> TYPE: DNA
<213> ORGANISM: Artificial Sequence
<220> FEATURE:
<223> OTHER INFORMATION: Synthetic PCR Primer for Amplifying Exon 4 of
      HLA-C gene.

<400> SEQUENCE: 30
gctctgggaa aggaggrgaa gg                                         22

<210> SEQ ID NO 31
<211> LENGTH: 18
<212> TYPE: DNA
<213> ORGANISM: Artificial Sequence
<220> FEATURE:
<223> OTHER INFORMATION: Synthetic PCR Primer for Amplifying Exon 2 of
      HLA-C gene.

<400> SEQUENCE: 31
gacccgggga gccgcgca                                              18

<210> SEQ ID NO 32
<211> LENGTH: 19
<212> TYPE: DNA
<213> ORGANISM: Artificial Sequence
<220> FEATURE:
<223> OTHER INFORMATION: Synthetic PCR Primer for Amplifying Exon 2 of
      HLA-C gene.

<400> SEQUENCE: 32
tcgagggtct gggcgggtt                                             19

<210> SEQ ID NO 33
<211> LENGTH: 19
<212> TYPE: DNA
<213> ORGANISM: Artificial Sequence
<220> FEATURE:
<223> OTHER INFORMATION: Synthetic PCR Primer for Amplifying Exon 3 of
      HLA-C gene.

<400> SEQUENCE: 33
gcccagaccc tcgrccgga                                             19

<210> SEQ ID NO 34
<211> LENGTH: 21
<212> TYPE: DNA
<213> ORGANISM: Artificial Sequence
<220> FEATURE:
<223> OTHER INFORMATION: Synthetic PCR Primer for Amplifying Exon 3 of
      HLA-C gene.

<400> SEQUENCE: 34
agatrgggaa ggctccccac t                     21

<210> SEQ ID NO 35
<211> LENGTH: 21
<212> TYPE: DNA
<213> ORGANISM: Artificial Sequence
<220> FEATURE:
<223> OTHER INFORMATION: Synthetic PCR Primer for Amplifying Exon 4 of
      HLA-C gene.

<400> SEQUENCE: 35
tctcaggatr gtcacatggg c                     21

<210> SEQ ID NO 36
<211> LENGTH: 22
<212> TYPE: DNA
<213> ORGANISM: Artificial Sequence
<220> FEATURE:
<223> OTHER INFORMATION: Synthetic PCR Primer for Amplifying Exon 4 of
      HLA-C gene.

<400> SEQUENCE: 36
gctctgggaa argaggrgaa gg                    22

<210> SEQ ID NO 37
<211> LENGTH: 21
<212> TYPE: DNA
<213> ORGANISM: Artificial Sequence
<220> FEATURE:
<223> OTHER INFORMATION: Synthetic PCR Primer for Amplifying Exon 2 of
      HLA-DQB1.

<400> SEQUENCE: 37
gattccycgc agaggatttc g                     21

<210> SEQ ID NO 38
<211> LENGTH: 21
<212> TYPE: DNA
<213> ORGANISM: Artificial Sequence
<220> FEATURE:
<223> OTHER INFORMATION: Synthetic PCR Primer for Amplifying Exon 2 of
      HLA-DQB1.

<400> SEQUENCE: 38
aggggcracs acgctcacct c                     21

<210> SEQ ID NO 39
<211> LENGTH: 22
<212> TYPE: DNA
<213> ORGANISM: Artificial Sequence
<220> FEATURE:
<223> OTHER INFORMATION: Synthetic PCR Primer for Amplifying Exon 3 of
      HLA-DQB1.

<400> SEQUENCE: 39
cctgtctgtt actgccctca gt                    22

<210> SEQ ID NO 40
<211> LENGTH: 25
<212> TYPE: DNA
<213> ORGANISM: Artificial Sequence
<220> FEATURE:
<223> OTHER INFORMATION: Synthetic PCR Primer.

<400> SEQUENCE: 40
ggcccatagt aacagaaact caata                 25

<210> SEQ ID NO 41
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 41
tcgcagacat ca                                                              12

<210> SEQ ID NO 42
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 42
tgacacgatg ct                                                              12

<210> SEQ ID NO 43
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 43
tacatcgcac ta                                                              12

<210> SEQ ID NO 44
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 44
tacagatgct ga                                                              12

<210> SEQ ID NO 45
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 45
ctcgatgagt ac                                                              12

<210> SEQ ID NO 46
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 46
acgtctagac ac                                                              12

<210> SEQ ID NO 47
<211> LENGTH: 12
<212> TYPE: DNA
<213> ORGANISM: Artificial Sequence
<220> FEATURE:

<223> OTHER INFORMATION: Synthetic PCR Primer.

<400> SEQUENCE: 47
tctgtatact ca                                                              12

<210> SEQ ID NO 48
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 48
tgctgtagtg ac                                                              12

<210> SEQ ID NO 49
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 49
tatctgctca ta                                                              12

<210> SEQ ID NO 50
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 50
agatatcgag ct                                                              12

<210> SEQ ID NO 51
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 51
tacatgctga gc                                                              12

<210> SEQ ID NO 52
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 52
acgtgtctat ca                                                              12

<210> SEQ ID NO 53
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 53
tcatatcgcg at                                                              12

```
<210> SEQ ID NO 54
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 54
agatcgtata gc                                                              12

<210> SEQ ID NO 55
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 55
acagatgcac gc                                                              12

<210> SEQ ID NO 56
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 56
atctcgtgac ag                                                              12

<210> SEQ ID NO 57
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 57
tagatcgtac at                                                              12

<210> SEQ ID NO 58
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 58
actagtacac gc                                                              12

<210> SEQ ID NO 59
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 59
actacacgtc tc                                                              12

<210> SEQ ID NO 60
<211> LENGTH: 12
<212> TYPE: DNA
<213> ORGANISM: Artificial Sequence
<220> FEATURE:
<223> OTHER INFORMATION: Synthetic PCR Primer.
```

```
<400> SEQUENCE: 60
atagtcacgc gt                                                            12

<210> SEQ ID NO 61
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 61
agactcgcgt at                                                            12

<210> SEQ ID NO 62
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 62
tactagctga cg                                                            12

<210> SEQ ID NO 63
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 63
atactagtgc tc                                                            12

<210> SEQ ID NO 64
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 64
tgtatcgtgc tc                                                            12

<210> SEQ ID NO 65
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 65
cacgatgaca tc                                                            12

<210> SEQ ID NO 66
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 66
tagtgagcgc ac                                                            12

<210> SEQ ID NO 67
<211> LENGTH: 12
```

```
<212> TYPE: DNA
<213> ORGANISM: Artificial Sequence
<220> FEATURE:
<223> OTHER INFORMATION: Synthetic PCR Primer.

<400> SEQUENCE: 67
tgctgtctcg ag                                                          12

<210> SEQ ID NO 68
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 68
catagcagtg tc                                                          12

<210> SEQ ID NO 69
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 69
tgtgctcgag tc                                                          12

<210> SEQ ID NO 70
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 70
tctgatcgag ca                                                          12

<210> SEQ ID NO 71
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 71
cactcgtaca tc                                                          12

<210> SEQ ID NO 72
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 72
agcgatgctc at                                                          12

<210> SEQ ID NO 73
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 73
```

-continued cgacgtgctc gc                                                    12

<210> SEQ ID NO 74
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 74
cgcgtactgc ag                                                    12

<210> SEQ ID NO 75
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 75
acgcatctat ac                                                    12

<210> SEQ ID NO 76
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 76
ctagtatcgc ag                                                    12

<210> SEQ ID NO 77
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 77
cgagatgact ct                                                    12

<210> SEQ ID NO 78
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 78
tgtatacacg at                                                    12

<210> SEQ ID NO 79
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 79
actgtctcga gc                                                    12

<210> SEQ ID NO 80
<211> LENGTH: 12
<212> TYPE: DNA
<213> ORGANISM: Artificial Sequence

```
<220> FEATURE:
<223> OTHER INFORMATION: Synthetic PCR Primer.

<400> SEQUENCE: 80
acgtagcgca ca                                                          12

<210> SEQ ID NO 81
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 81
catctgctat ag                                                          12

<210> SEQ ID NO 82
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 82
tctagctcat ga                                                          12

<210> SEQ ID NO 83
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 83
acgcactcta ga                                                          12

<210> SEQ ID NO 84
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 84
ctatgcactg at                                                          12

<210> SEQ ID NO 85
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 85
tgagatacag ta                                                          12

<210> SEQ ID NO 86
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 86
atctgctatg ac                                                          12
```

<210> SEQ ID NO 87
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 87
actcatcgtg ct                                                         12

<210> SEQ ID NO 88
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 88
tagagctgtc ac                                                         12

<210> SEQ ID NO 89
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 89
tacactgtct at                                                         12

<210> SEQ ID NO 90
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 90
cagcacatag at                                                         12

<210> SEQ ID NO 91
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 91
cacagtactc gc                                                         12

<210> SEQ ID NO 92
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 92
ctgctagtgt at                                                         12

<210> SEQ ID NO 93
<211> LENGTH: 12
<212> TYPE: DNA
<213> ORGANISM: Artificial Sequence
<220> FEATURE:
<223> OTHER INFORMATION: Synthetic PCR Primer.

```
<400> SEQUENCE: 93
tgtactatca ta                                                           12

<210> SEQ ID NO 94
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 94
tgtgatagac ac                                                           12

<210> SEQ ID NO 95
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 95
ctagtactga cg                                                           12

<210> SEQ ID NO 96
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 96
agcgagtcta ct                                                           12

<210> SEQ ID NO 97
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 97
tagactgagc ta                                                           12

<210> SEQ ID NO 98
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 98
acatactgag ac                                                           12

<210> SEQ ID NO 99
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 99
cagacgcgtg ag                                                           12

<210> SEQ ID NO 100
```

```
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 100
tacatctcgt at                                                           12

<210> SEQ ID NO 101
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 101
cgcgacatca cg                                                           12

<210> SEQ ID NO 102
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 102
tagcgatgag ac                                                           12

<210> SEQ ID NO 103
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 103
acactcatag at                                                           12

<210> SEQ ID NO 104
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 104
ctatcatgac ac                                                           12

<210> SEQ ID NO 105
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 105
agcgtatact ag                                                           12

<210> SEQ ID NO 106
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 106
```

-continued catactcacg ta                                                          12

<210> SEQ ID NO 107
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 107
tgtcgtgcta tc                                                          12

<210> SEQ ID NO 108
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 108
acatgactca cg                                                          12

<210> SEQ ID NO 109
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 109
cgctagactg ta                                                          12

<210> SEQ ID NO 110
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 110
tactatagtc ga                                                          12

<210> SEQ ID NO 111
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 111
acagtgtagc gc                                                          12

<210> SEQ ID NO 112
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 112
tgatatgcta ca                                                          12

<210> SEQ ID NO 113
<211> LENGTH: 12
<212> TYPE: DNA

```
<213> ORGANISM: Artificial Sequence
<220> FEATURE:
<223> OTHER INFORMATION: Synthetic PCR Primer.

<400> SEQUENCE: 113
cactctatcg ac                                                          12

<210> SEQ ID NO 114
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 114
tcacgcgatg ag                                                          12

<210> SEQ ID NO 115
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 115
acactctagt ca                                                          12

<210> SEQ ID NO 116
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 116
acgtagatct at                                                          12

<210> SEQ ID NO 117
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 117
catatgagat cg                                                          12

<210> SEQ ID NO 118
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 118
agcagagtgc tc                                                          12

<210> SEQ ID NO 119
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 119
cagctatcat ac                                                          12
```

<210> SEQ ID NO 120
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 120
cactgcagac ga                                                            12

<210> SEQ ID NO 121
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 121
tatactctag at                                                            12

<210> SEQ ID NO 122
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 122
tgcatagagc gc                                                            12

<210> SEQ ID NO 123
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 123
tgtatgctcg tc                                                            12

<210> SEQ ID NO 124
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 124
tcgtgacaga tc                                                            12

<210> SEQ ID NO 125
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 125
tagtgatgct ct                                                            12

<210> SEQ ID NO 126
<211> LENGTH: 12
<212> TYPE: DNA
<213> ORGANISM: Artificial Sequence
<220> FEATURE:

<223> OTHER INFORMATION: Synthetic PCR Primer.

<400> SEQUENCE: 126
acgagctgat at                                                           12

<210> SEQ ID NO 127
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 127
agactctgag tc                                                           12

<210> SEQ ID NO 128
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 128
ctgatagtat ca                                                           12

<210> SEQ ID NO 129
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 129
ctcatagact ac                                                           12

<210> SEQ ID NO 130
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 130
atcgcgagtg ac                                                           12

<210> SEQ ID NO 131
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 131
tcgctcacta ca                                                           12

<210> SEQ ID NO 132
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 132
tgtctcgaca tc                                                           12

```
<210> SEQ ID NO 133
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 133
atagagtctc at                                                            12

<210> SEQ ID NO 134
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 134
cgcatagcgt at                                                            12

<210> SEQ ID NO 135
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 135
cgagacactc gc                                                            12

<210> SEQ ID NO 136
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 136
tcgtagtcta ca                                                            12

<210> SEQ ID NO 137
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 137
cagcatacta tc                                                            12

<210> SEQ ID NO 138
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 138
tcgtgataca ga                                                            12

<210> SEQ ID NO 139
<211> LENGTH: 12
<212> TYPE: DNA
<213> ORGANISM: Artificial Sequence
<220> FEATURE:
<223> OTHER INFORMATION: Synthetic PCR Primer.
```

<400> SEQUENCE: 139
cagctatagt ct                                                    12

<210> SEQ ID NO 140
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 140
atgcagatat ct                                                    12

<210> SEQ ID NO 141
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 141
tctatcgatg ca                                                    12

<210> SEQ ID NO 142
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 142
acacgcagat cg                                                    12

<210> SEQ ID NO 143
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 143
catgagtata gc                                                    12

<210> SEQ ID NO 144
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 144
ctagctgacg ta                                                    12

<210> SEQ ID NO 145
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 145
tagcatatcg ag                                                    12

<210> SEQ ID NO 146
<211> LENGTH: 12

```
<212> TYPE: DNA
<213> ORGANISM: Artificial Sequence
<220> FEATURE:
<223> OTHER INFORMATION: Synthetic PCR Primer.

<400> SEQUENCE: 146
tacacgtatg ag                                                          12

<210> SEQ ID NO 147
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 147
acgactcgct ac                                                          12

<210> SEQ ID NO 148
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 148
tcatgactag ta                                                          12

<210> SEQ ID NO 149
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 149
tagcatacac gc                                                          12

<210> SEQ ID NO 150
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 150
tgacgcgtat ac                                                          12

<210> SEQ ID NO 151
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 151
cgtcatatgc ag                                                          12

<210> SEQ ID NO 152
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 152
```
tatagcgatg ac				12

<210> SEQ ID NO 153
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 153
tgcagcgagt ac				12

<210> SEQ ID NO 154
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 154
tcgacgctag cg				12

<210> SEQ ID NO 155
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 155
cgtgtcgaca ga				12

<210> SEQ ID NO 156
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 156
cagtcgtgag ca				12

<210> SEQ ID NO 157
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 157
actcgacgtg ag				12

<210> SEQ ID NO 158
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 158
acgcgagtga ta				12

<210> SEQ ID NO 159
<211> LENGTH: 12
<212> TYPE: DNA
<213> ORGANISM: Artificial Sequence -continued

```
<220> FEATURE:
<223> OTHER INFORMATION: Synthetic PCR Primer.

<400> SEQUENCE: 159
actcgtctga cg                                                           12

<210> SEQ ID NO 160
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 160
tgctatcact ga                                                           12

<210> SEQ ID NO 161
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 161
catactgtat ct                                                           12

<210> SEQ ID NO 162
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 162
tacatagatg tc                                                           12

<210> SEQ ID NO 163
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 163
tctactcgtg ac                                                           12

<210> SEQ ID NO 164
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 164
cacgtatagt ga                                                           12

<210> SEQ ID NO 165
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 165
ctgcactaga ca                                                           12
```

<210> SEQ ID NO 166
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 166
actcatatcg ca                                                           12

<210> SEQ ID NO 167
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 167
acacgagctc at                                                           12

<210> SEQ ID NO 168
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 168
cactcatatc ga                                                           12

<210> SEQ ID NO 169
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 169
tacagatagt ct                                                           12

<210> SEQ ID NO 170
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 170
tcgtctgtga ta                                                           12

<210> SEQ ID NO 171
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 171
tacactcgtg ct                                                           12

<210> SEQ ID NO 172
<211> LENGTH: 12
<212> TYPE: DNA
<213> ORGANISM: Artificial Sequence
<220> FEATURE:
<223> OTHER INFORMATION: Synthetic PCR Primer.

```
<400> SEQUENCE: 172
tgacgctcat ct                                                            12

<210> SEQ ID NO 173
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 173
tacatgtgac ga                                                            12

<210> SEQ ID NO 174
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 174
tcgtacatgc tc                                                            12

<210> SEQ ID NO 175
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 175
tgtatgatct cg                                                            12

<210> SEQ ID NO 176
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 176
cactgtgctc at                                                            12

<210> SEQ ID NO 177
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 177
cagtacactc ta                                                            12

<210> SEQ ID NO 178
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 178
actgcatgat cg                                                            12

<210> SEQ ID NO 179
```

-continued

```
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 179
catactatca cg                                                         12

<210> SEQ ID NO 180
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 180
tcgtgtcact ac                                                         12

<210> SEQ ID NO 181
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 181
cactatacag at                                                         12

<210> SEQ ID NO 182
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 182
cgacacgtac ta                                                         12

<210> SEQ ID NO 183
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 183
atatcgtagc at                                                         12

<210> SEQ ID NO 184
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 184
tcgtgatcac ta                                                         12

<210> SEQ ID NO 185
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 185
```

-continued tagtctatac at                                              12

<210> SEQ ID NO 186
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 186
agacgctgtc ga                                              12

<210> SEQ ID NO 187
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 187
tgtcacagtg ac                                              12

<210> SEQ ID NO 188
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 188
tcatatgatc ga                                              12

<210> SEQ ID NO 189
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 189
atcgactatg ct                                              12

<210> SEQ ID NO 190
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 190
cgatcatatg ag                                              12

<210> SEQ ID NO 191
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 191
atactagcat ca                                              12

<210> SEQ ID NO 192
<211> LENGTH: 12
<212> TYPE: DNA

```
<213> ORGANISM: Artificial Sequence
<220> FEATURE:
<223> OTHER INFORMATION: Synthetic PCR Primer.

<400> SEQUENCE: 192
tcatgctgac ga                                                              12

<210> SEQ ID NO 193
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 193
cactgacgct ca                                                              12

<210> SEQ ID NO 194
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 194
cactacatcg ct                                                              12

<210> SEQ ID NO 195
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 195
tcgctcatct at                                                              12

<210> SEQ ID NO 196
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 196
tagtacagag ct                                                              12

<210> SEQ ID NO 197
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 197
tgtatcacga gc                                                              12

<210> SEQ ID NO 198
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 198
atgatcgtat ac                                                              12
```

```
<210> SEQ ID NO 199
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 199
tactgctatc tc                                                            12

<210> SEQ ID NO 200
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 200
cgctgcatag cg                                                            12

<210> SEQ ID NO 201
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 201
cgcgagctcg tc                                                            12

<210> SEQ ID NO 202
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 202
actcgatgag ct                                                            12

<210> SEQ ID NO 203
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 203
tagagtctgt at                                                            12

<210> SEQ ID NO 204
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 204
tgtctatcac at                                                            12

<210> SEQ ID NO 205
<211> LENGTH: 12
<212> TYPE: DNA
<213> ORGANISM: Artificial Sequence
<220> FEATURE:
```

<223> OTHER INFORMATION: Synthetic PCR Primer.

<400> SEQUENCE: 205
tactatcgct ct                                                        12

<210> SEQ ID NO 206
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 206
tatgtgacat ac                                                        12

<210> SEQ ID NO 207
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 207
tagatgacgc tc                                                        12

<210> SEQ ID NO 208
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 208
tactcgtagc gc                                                        12

<210> SEQ ID NO 209
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 209
tcgcgtgaca tc                                                        12

<210> SEQ ID NO 210
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 210
atctactgac gt                                                        12

<210> SEQ ID NO 211
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 211
acacgctcta ct                                                        12

```
<210> SEQ ID NO 212
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 212
acagtagcgc ac                                                         12

<210> SEQ ID NO 213
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 213
tacatagtct cg                                                         12

<210> SEQ ID NO 214
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 214
ctagtatcat ga                                                         12

<210> SEQ ID NO 215
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 215
tgagtagcac gc                                                         12

<210> SEQ ID NO 216
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 216
tcgatcatgc ag                                                         12

<210> SEQ ID NO 217
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 217
tagatgctat ac                                                         12

<210> SEQ ID NO 218
<211> LENGTH: 12
<212> TYPE: DNA
<213> ORGANISM: Artificial Sequence
<220> FEATURE:
<223> OTHER INFORMATION: Synthetic PCR Primer.
```

```
<400> SEQUENCE: 218
tacatgcact ca                                                         12

<210> SEQ ID NO 219
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 219
atcgatgtca cg                                                         12

<210> SEQ ID NO 220
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 220
cagctcgact ac                                                         12

<210> SEQ ID NO 221
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 221
atcatatgta gc                                                         12

<210> SEQ ID NO 222
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 222
ctctacagtc ac                                                         12

<210> SEQ ID NO 223
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 223
tagcatcgat at                                                         12

<210> SEQ ID NO 224
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 224
agatagcaca tc                                                         12

<210> SEQ ID NO 225
<211> LENGTH: 12
```

```
<212> TYPE: DNA
<213> ORGANISM: Artificial Sequence
<220> FEATURE:
<223> OTHER INFORMATION: Synthetic PCR Primer.

<400> SEQUENCE: 225
tgatcgacgc tc                                                          12

<210> SEQ ID NO 226
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 226
ctagatatcg tc                                                          12

<210> SEQ ID NO 227
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 227
tgcagctcat ag                                                          12

<210> SEQ ID NO 228
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 228
tacagactgc ac                                                          12

<210> SEQ ID NO 229
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 229
cgacgtagag tc                                                          12

<210> SEQ ID NO 230
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 230
cagtagcact ac                                                          12

<210> SEQ ID NO 231
<211> LENGTH: 21
<212> TYPE: DNA
<213> ORGANISM: Artificial Sequence
<220> FEATURE:
<223> OTHER INFORMATION: Synthetic PCR Primer for amplification of Exon
      2 of HLA-DRB1
      gene.
```

<400> SEQUENCE: 231
cacgtttctt ggagtactct a                                              21

<210> SEQ ID NO 232
<211> LENGTH: 22
<212> TYPE: DNA
<213> ORGANISM: Artificial Sequence
<220> FEATURE:
<223> OTHER INFORMATION: Synthetic PCR Primer for amplification of Exon
      2 of HLA-DRB1
      gene.

<400> SEQUENCE: 232
gtttcttgtg gcagcttaag tt                                             22

<210> SEQ ID NO 233
<211> LENGTH: 20
<212> TYPE: DNA
<213> ORGANISM: Artificial Sequence
<220> FEATURE:
<223> OTHER INFORMATION: Synthetic PCR Primer for amplification of Exon
      2 of HLA-DRB1
      gene.

<400> SEQUENCE: 233
cctgtggcag ggtaagtata                                                20

<210> SEQ ID NO 234
<211> LENGTH: 22
<212> TYPE: DNA
<213> ORGANISM: Artificial Sequence
<220> FEATURE:
<223> OTHER INFORMATION: Synthetic PCR Primer for amplification of Exon
      2 of HLA-DRB1
      gene.

<400> SEQUENCE: 234
gtttcttgaa gcaggataag tt                                             22

<210> SEQ ID NO 235
<211> LENGTH: 19
<212> TYPE: DNA
<213> ORGANISM: Artificial Sequence
<220> FEATURE:
<223> OTHER INFORMATION: Synthetic PCR Primer for amplification of Exon
      2 of HLA-DRB1
      gene.

<400> SEQUENCE: 235
gcacgtttct tggaggagg                                                 19

<210> SEQ ID NO 236
<211> LENGTH: 20
<212> TYPE: DNA
<213> ORGANISM: Artificial Sequence
<220> FEATURE:
<223> OTHER INFORMATION: Synthetic PCR Primer for amplification of Exon
      2 of HLA-DRB1
      gene.

<400> SEQUENCE: 236
tttcctgtgg cagcctaaga                                                20

<210> SEQ ID NO 237
<211> LENGTH: 21
<212> TYPE: DNA
<213> ORGANISM: Artificial Sequence

```
<220> FEATURE:
<223> OTHER INFORMATION: Synthetic PCR Primer for amplification of Exon
      2 of HLA-DRB1
      gene.

<400> SEQUENCE: 237
gtttcttgga gcaggttaaa c                                              21

<210> SEQ ID NO 238
<211> LENGTH: 19
<212> TYPE: DNA
<213> ORGANISM: Artificial Sequence
<220> FEATURE:
<223> OTHER INFORMATION: Synthetic PCR Primer for amplification of Exon
      2 of HLA-DRB1
      gene.

<400> SEQUENCE: 238
cctcacctcg ccgctgcac                                                 19

<210> SEQ ID NO 239
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 239
cactgtatag ct                                                        12

<210> SEQ ID NO 240
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 240
cgactagtac ta                                                        12

<210> SEQ ID NO 241
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 241
cgacgtagag tc                                                        12

<210> SEQ ID NO 242
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 242
cagtagcact ac                                                        12

<210> SEQ ID NO 243
<211> LENGTH: 12
<212> TYPE: DNA
<213> ORGANISM: Artificial Sequence
<220> FEATURE:
<223> OTHER INFORMATION: Synthetic PCR Primer.
```

```
<400> SEQUENCE: 243
cactgtatag ct                                                         12

<210> SEQ ID NO 244
<211> LENGTH: 12
<212> TYPE: DNA
<213> ORGANISM: Artificial Sequence
<220> FEATURE:
<223> OTHER INFORMATION: Synthetic PCR Primer.

<400> SEQUENCE: 244
cgactagtac ta                                                         12

<210> SEQ ID NO 245
<211> LENGTH: 91
<212> TYPE: DNA
<213> ORGANISM: Homo sapiens

<400> SEQUENCE: 245
accaggagac acggaatatg aaggcccact cacagactga ccgagcgaac ctggggaccc      60
tgcgcgccta ctacaaccag agcgaggacg g                                    91

<210> SEQ ID NO 246
<211> LENGTH: 267
<212> TYPE: DNA
<213> ORGANISM: Homo sapiens

<400> SEQUENCE: 246
gctctcactc catgaggtat ttcttcacat ccgtgtcccg gcccggccgc ggggagcccc      60
gcttcatcgc agtgggctac gtggacgaca cgcagttcgt gcggttcgac agcgacgccg     120
cgagccagac gatggacccg cggccgccgt ggatagagca ggagggtccg gagtattggg     180
acgggcagac acggaaagtg aaccccact cacagactca ccgagtggac ctggggaccc     240
tgcgcggcta caaccagagc gaggccg                                        267

<210> SEQ ID NO 247
<211> LENGTH: 270
<212> TYPE: DNA
<213> ORGANISM: Homo sapiens

<400> SEQUENCE: 247
gctcccactc catgaggtat ttctacacct ccgtgtcccg gcccggccgc ggggagcccc      60
gcttcatcgc cgtgggctac gtggacgaca cgcagttcgt gcggttcgac agcgacgccg     120
cgagccagag gatggagccg cgggcgccgt gcatagagca ggaggggccg gagtattggg     180
accaggagac acggaatgtg aaggcccagt cacagactga ccgagtggac ctggggaccc     240
tgcgcggcta ctacaaccag agcgaggacg                                     270

<210> SEQ ID NO 248
<211> LENGTH: 71
<212> TYPE: DNA
<213> ORGANISM: Homo sapeins

<400> SEQUENCE: 248
aggcacagac tgaccgagtg agcctgccga acctgcgcgg ctactacaac cagagcgagg      60
ccggtgagtc a                                                          71

<210> SEQ ID NO 249
<211> LENGTH: 270
```

<212> TYPE: DNA
<213> ORGANISM: Homo sapeins

<400> SEQUENCE: 249

```
gctcccactc catgaagtat ttcttcacat ccgtgtcccg gcctggccgc ggagagcccc    60
gcttcatctc agtgggctac gtggacgaca cgcagttcgt gcggttcgac agcgacgccg   120
cgagtccgag aggggagccg cgggcgccgt gggtggagca ggaggggccg gagtattggg   180
accgggagac acagaagtac aagcgccagg cacagactga ccgagtgagc ctgcggaacc   240
tgcgcggcta ctacaaccag agcgaggccg                                    270
```

<210> SEQ ID NO 250
<211> LENGTH: 270
<212> TYPE: DNA
<213> ORGANISM: Homo sapiens

<400> SEQUENCE: 250

```
gctcccactc catgaggtat ttcgacaccg ccgtgtcccg gccgggccgc ggagagcccc    60
gcttcatctc agtgggctac gtggacgaca cgcagttcgt gcggttcgac agcgacgccg   120
cgagtccgag aggggagccg cgggcgccgt gggtggagca ggaggggccg gagtattggg   180
accgggagac acagaagtac aagcgccagg cacaggctga ccgagtgagc ctgcggaacc   240
tgcgcggcta ctacaaccag agcgaggacg                                    270
```

<210> SEQ ID NO 251
<211> LENGTH: 36
<212> TYPE: DNA
<213> ORGANISM: Artificial sequence
<220> FEATURE:
<223> OTHER INFORMATION: Homo sapiens

<400> SEQUENCE: 251

```
catrtkcagc aygagrggyt gcmrgagccc ykcacy                              36
```

<210> SEQ ID NO 252
<211> LENGTH: 36
<212> TYPE: DNA
<213> ORGANISM: Artificial sequence
<220> FEATURE:
<223> OTHER INFORMATION: Homo sapiens

<400> SEQUENCE: 252

```
catgtgcagc acgaggggct gccrgagccc ctcacc                              36
```

<210> SEQ ID NO 253
<211> LENGTH: 36
<212> TYPE: DNA
<213> ORGANISM: Homo sapiens

<400> SEQUENCE: 253

```
catgtgcagc acgaggggct gccrgagccc ctcacc                              36
```

<210> SEQ ID NO 254
<211> LENGTH: 31
<212> TYPE: DNA
<213> ORGANISM: Artificial sequence
<220> FEATURE:
<223> OTHER INFORMATION: Homo sapiens

<400> SEQUENCE: 254

```
gtgcagcacg aggggctgcr gagcccctca g                                   31
```

<210> SEQ ID NO 255
<211> LENGTH: 31
<212> TYPE: DNA
<213> ORGANISM: Artificial sequence
<220> FEATURE:
<223> OTHER INFORMATION: Homo sapiens

<400> SEQUENCE: 255
gtgcagcacg aggggctgcc rgagccctc a                            31

<210> SEQ ID NO 256
<211> LENGTH: 91
<212> TYPE: DNA
<213> ORGANISM: Artificial sequence
<220> FEATURE:
<223> OTHER INFORMATION: Homo sapiens

<400> SEQUENCE: 256
ggagttccgg gcggtgacgc tgcgggggct gcctgcggcc gagtactgga acagccagaa    60
ggacatcctg gagaggaaac gggcggcgct g                            91

<210> SEQ ID NO 257
<211> LENGTH: 271
<212> TYPE: DNA
<213> ORGANISM: Artificial sequence
<220> FEATURE:
<223> OTHER INFORMATION: Homo sapiens

<400> SEQUENCE: 257
aggatttcgt gtaccagttt aagggcatgt gctacttcac caacgggacg gagcgccgtg    60
cgtcttgtga ccagatacat ctataaccga gaggagtacg cacgcttcga cagcgacgtg   120
ggggtgtatc gggcggtgac gccgctgggg ccgcctgacg ccgagtactg gaacagccag   180
aaggaagtcc tggagaggac ccgggcggag ttggacacgg tgtgcagaca caactaccag   240
ttggagctcc gcacgacctt gcagcggcga g                           271

<210> SEQ ID NO 258
<211> LENGTH: 270
<212> TYPE: DNA
<213> ORGANISM: Artificial sequence
<220> FEATURE:
<223> OTHER INFORMATION: Homo sapiens

<400> SEQUENCE: 258
aggatttcgt gttccagttt aagggcatgt gctacttcac caacgggacg gagcgcgtgc    60
gtcttgtgac cagatacatc tataaccgag aggagtacgc gcgcttcgac agcgacgtgg   120
gggtgtaccg cgcggtgacg ccgcaggggc ggcctgatgc cgagtactgg aacagccaga   180
aggaagtcct ggaggggacc cgggcggagt tgcacacggt gtgcagacac aactacgagg   240
tggcgttccg cgggatcttg cagaggagag                             270

<210> SEQ ID NO 259
<211> LENGTH: 38
<212> TYPE: DNA
<213> ORGANISM: Artificial sequence
<220> FEATURE:
<223> OTHER INFORMATION: Homo sapiens

<400> SEQUENCE: 259
cgagargagd wcryrcgctt sgacagcgac gtggrggw                     38

```
<210> SEQ ID NO 260
<211> LENGTH: 38
<212> TYPE: DNA
<213> ORGANISM: Artificial sequence
<220> FEATURE:
<223> OTHER INFORMATION: Homo sapiens

<400> SEQUENCE: 260
cgagaggagt acgcrcgctt cgacagcgac gtgggggt                              38

<210> SEQ ID NO 261
<211> LENGTH: 38
<212> TYPE: DNA
<213> ORGANISM: Artificial sequence
<220> FEATURE:
<223> OTHER INFORMATION: Homo sapiens

<400> SEQUENCE: 261
cgagaggagt acgcrcgctt cgacagcgac gtgggggt                              38

<210> SEQ ID NO 262
<211> LENGTH: 38
<212> TYPE: DNA
<213> ORGANISM: Artificial sequence
<220> FEATURE:
<223> OTHER INFORMATION: Homo sapiens

<400> SEQUENCE: 262
cgagaggagt acgcrcgctt cgacagcgac gtgggggt                              38

<210> SEQ ID NO 263
<211> LENGTH: 38
<212> TYPE: DNA
<213> ORGANISM: Artificial sequence
<220> FEATURE:
<223> OTHER INFORMATION: Homo sapiens

<400> SEQUENCE: 263
cgagaggagt acgcacgctt cgacagcgac gtgggggt                              38

<210> SEQ ID NO 264
<211> LENGTH: 38
<212> TYPE: DNA
<213> ORGANISM: Artificial sequence
<220> FEATURE:
<223> OTHER INFORMATION: Homo sapiens

<400> SEQUENCE: 264
cgagaggagt acgcgcgctt cgacagcgac gtgggggt                              38

<210> SEQ ID NO 265
<211> LENGTH: 38
<212> TYPE: DNA
<213> ORGANISM: Artificial sequence
<220> FEATURE:
<223> OTHER INFORMATION: Homo sapiens

<400> SEQUENCE: 265
cgagaggagt acgcacgctt cgacagcgac gtgggggt                              38

<210> SEQ ID NO 266
<211> LENGTH: 34
<212> TYPE: DNA
<213> ORGANISM: Artificial sequence
<220> FEATURE:
<223> OTHER INFORMATION: Homo sapiens
```

```
<400> SEQUENCE: 266
atctataacc gagaggagta cgcrcgcttc gaca                              34

<210> SEQ ID NO 267
<211> LENGTH: 91
<212> TYPE: DNA
<213> ORGANISM: Artificial sequence
<220> FEATURE:
<223> OTHER INFORMATION: Homo sapiens

<400> SEQUENCE: 267
ggagttccgg gcggtgacgc tgcgggggct gcctgcggcc gagtactgga acagccagaa   60
ggacatcctg gagaggaaac gggcggcggt g                                 91

<210> SEQ ID NO 268
<211> LENGTH: 270
<212> TYPE: DNA
<213> ORGANISM: Artificial sequence
<220> FEATURE:
<223> OTHER INFORMATION: Homo sapiens

<400> SEQUENCE: 268
aggatttcgt gtaccagttt aagggcatgt gctacttcac caacgggacg gagcgcgtgc   60
gtcttgtgac cagatacatc tataaccgag aggagtacgc acgcttcgac agcgacgtgg  120
gggtgtatcg ggcggtgacg ccgctggggc cgcctgacgc cgagtactgg aacagccaga  180
aggaagtcct ggagaggacc cgggcggagt tggacacggt gtgcagacac aactaccagt  240
tggagctccg cacgaccttg cagcggcgag                                  270

<210> SEQ ID NO 269
<211> LENGTH: 273
<212> TYPE: DNA
<213> ORGANISM: Artificial sequence
<220> FEATURE:
<223> OTHER INFORMATION: Homo sapiens

<400> SEQUENCE: 269
aggatttcgt gttccagttt aagggcatgt gctacttcac caacgggacg gagcgcgtgc   60
gtcgtcttgt gaccagatac atctataacc gagaggagta cgcgcgcttc gacagcgacc  120
tgggggtgta ccgcgcggtg acgccgcagg ggcggcctga tgccgagtac tggaacagcc  180
agaaggaagt cctggagggg acccgggcgg agttggacac ggtgtgcaga cacaactacg  240
aggtggcgtt ccgcgggatc ttgcagagga gag                              273
```